(12) United States Patent
Binggeli et al.

(10) Patent No.: US 8,026,255 B2
(45) Date of Patent: *Sep. 27, 2011

(54) SUBSTITUTED PIPERIDINES AS SOMATOSTATIN RECEPTOR SUBTYPE 5 (SSTR5) ANTAGONISTS

(75) Inventors: Alfred Binggeli, Binningen (CH); Andreas D. Christ, Arlesheim (CH); Hans P. Maerki, Basel (CH); Rainer E. Martin, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/776,748

(22) Filed: May 10, 2010

(65) Prior Publication Data

US 2010/0222350 A1   Sep. 2, 2010

Related U.S. Application Data

(62) Division of application No. 11/834,184, filed on Aug. 6, 2007, now Pat. No. 7,754,744.

(30) Foreign Application Priority Data

Aug. 15, 2006 (EP) .................................. 06118923

(51) Int. Cl.
*A61K 31/445* (2006.01)
(52) U.S. Cl. ........ 514/317; 544/129; 544/336; 544/360; 546/122; 546/139; 546/176; 546/244; 546/268.1; 548/247; 548/254; 548/306.1; 548/518; 548/561; 549/49; 549/407
(58) Field of Classification Search .................. 514/317; 544/129, 336, 360; 546/122, 139, 176, 244, 546/268.1; 548/247, 254, 306.1, 518, 561; 549/49, 407
See application file for complete search history.

(56) References Cited

FOREIGN PATENT DOCUMENTS
EP   1 256 574 A   11/2002
EP   1 571 146 A    9/2005
WO   03/106452    12/2003

OTHER PUBLICATIONS

J. Moragues et al Farmaco, Edizione Scientifica, vol. 35, No. 11, 1980, pp. 951-964, XP009032424.

*Primary Examiner* — James O Wilson
*Assistant Examiner* — Douglas M Willis
(74) *Attorney, Agent, or Firm* — George W. Johnston; Dennis P. Tramaloni; Samuel H. Megerditchian

(57) ABSTRACT

This invention is concerned with compounds of the formula

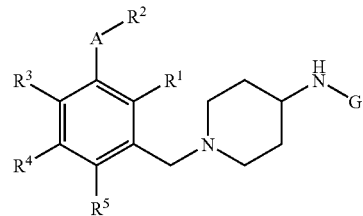

and pharmaceutically acceptable salts thereof. The invention further relates to pharmaceutical compositions containing such compounds, to a process for their preparation and to their use for the treatment and/or prevention of diseases which are associated with the modulation of SST receptors subtype 5.

22 Claims, No Drawings ns have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration (C. J. Bailey et al., vide supra). The sulfonylureas, though having good hypoglycemic activity, require great care during use because they frequently cause serious hypoglycemia and are most effective over a period of circa ten years. The thiazolidinediones may cause weight gain following chronic administration (G. L. Plosker and D. Faulds, vide supra) and troglitazone has been associated with the occurrence of serious hepatic dysfunction.

SUBSTITUTED PIPERIDINES AS SOMATOSTATIN RECEPTOR SUBTYPE 5 (SSTR5) ANTAGONISTS

PRIORITY TO RELATED APPLICATION(S)

This application is a division of U.S. application Ser. No. 11/834,184, filed Aug. 6, 2007 now pending, which claims the benefit of European Patent Application No. 06118923.9, filed Aug. 15, 2006, which is hereby incorporated by reference in its entirety.

FIELD OF THE INVENTION

The present invention is concerned with novel phenyl, pyridine, quinoline, isoquinoline, naphthyridine and pyrazine derivatives, their manufacture, pharmaceutical compositions containing them and their use as medicaments. The active compounds of the present invention are useful in the prevention and/or treatment of diabetes mellitus and other disorders.

In particular, the present invention is concerned with compounds of the general formula I

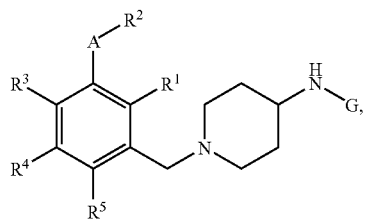

and pharmaceutically acceptable salts thereof.

The compounds of formula I possess pharmaceutical activity, in particular they are modulators of somatostatine receptor activity. More particularly, the compounds are antagonists of the somatostatine receptor subtype 5 (SSTR5).

All documents cited or relied upon below are expressly incorporated herein by reference.

BACKGROUND OF THE INVENTION

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g., cardiovascular disease (G. C. Weir and J. L. Leahy, Pathogenesis of non-insulin dependent (Type II) diabetes mellitus, in *Joslin's Diabetes Mellitus* (Eds. C. R. Kahn and G. C. Weir), 13$^{th}$ Edition, 1994, Lea & Febiger, Malvern, Pa., pp. 240-264). NIDDM is characterized by both fasting and post-prandial hyperglycemia resulting from abnormalities in insulin secretion and insulin action (G. C. Weir et al., vide supra).

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. Currently, the most widely used oral antidiabetic agents are the sulfonylureas, which act by increasing the secretion of insulin from the pancreas (H. E. Lebovitz, Oral antidiabetic agents, in *Joslin's Diabetes Mellitus* (Eds. C. R. Kahn and G. C. Weir), 13$^{th}$ Edition, 1994, Lea & Febiger, Malvern, Pa., pp. 508-529), the biguanides (e.g., metformin) which act on the liver and periphery by unknown mechanisms (C. J. Bailey, M. R. C. Path and R. C. Turner N. *Engl. J. Med.* 1996, 334, 574-579) and the thiazolidinediones (e.g., rosiglitazone/Avandia®), which enhance the effects of insulin at peripheral target sites (G. L. Plosker and D. Faulds *Drugs* 1999, 57, 409-438). These existing therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration (C. J. Bailey et al., vide supra). The sulfonylureas, though having good hypoglycemic activity, require great care during use because they frequently cause serious hypoglycemia and are most effective over a period of circa ten years. The thiazolidinediones may cause weight gain following chronic administration (G. L. Plosker and D. Faulds, vide supra) and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells. GLP-1 in turn is one of the most potent stimulators of insulin production and secretion and is a trophic factor for β cells. β and L cells express SST receptor subtype 5 (SSTR5) and agonizing this receptor suppresses insulin and GLP-1 secretion in humans and in animal models (e.g., Y. Zambre, Z. Ling, M.-C. Chen, X. Hou, C.-W. Woon, M. Culler, J. E. Taylor, D. H. Coy, C. van Schravendijk, F. Schuit, D. G. Pipeleers and D. L. Eizirik *Biochem. Pharmacol.* 1999, 57, 1159-1164; S. P. Fagan, A. Azizzadeh, S. Moldovan, M. K. Ray, T. E. Adrian, X. Ding, D. H. Coy and F. C. Brunicardi *Surgery* 1998, 124, 254-258; M. Norman, S. Moldovan, V. Seghers, X.-P. Wang, F. J. DeMayo and F. C. Brunicardi *Ann. Surg.* 2002, 235, 767-774; T. A. Tirone, M. A. Norman, S. Moldovan, F. J. DeMayo, X.-P. Wang and F. C.

Brunicardi *Pancreas* 2003, 26, e67-73; M. Z. Strowski, M. Köhler, H. Y. Chen, M. E. Trumbauer, Z. Li, D. Szalkowski, S. Gopal-Truter, J. K. Fisher, J. M. Schaeffer, A. D. Blake, B. B. Zhang and H. A. Wilkinson *Mol. Endocrinol.* 2003, 17, 93-106).

Consequently, antagonizing the effect of SST would lead to higher plasma insulin concentrations. In patients suffering from impaired glucose tolerance and NIDDM, a higher plasma insulin concentration would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy and S. Efendic *Diabetes* 2003, 52, 1176-1181; M. Z. Strowski, R. M. Parmar, A. D. Blake and J. M. Schaeffer *Endocrinology* 2000, 141, 111-117). Advantageous over established therapies is the dual mechanism of action to increase insulin secretion: directly on pancreatic β cells and indirectly through GLP-1 release from L cells. Additionally, SSTR5 knockout mice demonstrated higher insulin sensitivity than littermates (M. Z. Strowski, M. Köhler et al., vide supra). Therefore, SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

GLP-1 is known as an endogenous regulator of gastrointestinal motility and of food intake reducing appetite as shown in laboratory animals, healthy volunteers and patients with NIDDM (E. Näslund, B. Barkeling, N. King, M. Gutniak, J. E. Blundell, J. J. Holst, S. Rössner and P. M. Hellström *Int. J. Obes.* 1999, 23, 304-311; J.-P. Gutzwiller, B. Göke, J. Drewe, P. Hildebrand, S. Ketterer, D. Handschin, R. Winterhalder, D. Conen and C. Beglinger *Gut* 1999, 44, 81-88; J.-P. Gutzwiller, J. Drewe, B. Göke, H. Schmidt, B. Rohrer, J. Lareida and C. Beglinger *Am. J. Physiol.* 1999, 276, R1541-1544; M. D. Turton, D. O'Shea, I. Gunn, S. A. Beak, C. M. Edwards, K. Meeran, S. J. Choi, G. M. Taylor, M. M. Heath, P. D. Lambert, J. P. Wilding, D. M. Smith, M. A. Ghatei, J. Herbert and S. R. Bloom *Nature* 1996, 379, 69-72; A. Flint, A. Raben, A. Astrup and J. J. Holst *J. Clin. Invest.* 1998, 101, 515-520; M. B. Toft-Nielsen, S. Madsbad and J. J. Holst *Diabetes Care* 1999, 22, 1137-1143; P. K. Cheikani, A. C. Haver and R. D. Reidelberger *Am. J. Physiol.* 2005, 288, R1695-R1706; T. Miki, K. Minami, H. Shinozaki, K. Matsumura, A. Saraya, H. Ikeda, Y. Yamada, J. J. Hoist and S. Seino *Diabetes* 2005, 54, 1056-1063); thus, elevated GLP-1 will also counteract obesity, a typical condition associated with and leading to NIDDM.

GLP-1 is co-secreted with GLP-2 that is, consequently, also regulated by SST through SSTR5 (L. Hansen, B. Hartmann, T. Bisgaard, H. Mineo, P. N. Jørgensen and J. J. Hoist *Am. J. Phys.* 2000, 278, E1010-1018). GLP-2 is enterotrophic and beneficial in patients with malabsorption of certain origins, such as short bowel syndrome (D. G. Burrin, B. Stoll and X. Guan *Domest. Anim. Endocrinol.* 2003, 24, 103-122; K. V. Haderslev, P. B. Jeppesen, B. Hartmann, J. Thulesen, H. A. Sorensen, J. Graff, B. S. Hansen, F. Tofteng, S. S. Poulsen, J. L. Madsen, J. J. Hoist, M. Staun and P. B. Mortensen *Scand. J. Gastroenterol.* 2002, 37, 392-398; P. B. Jeppesen *J. Nutr.* 2003, 133, 3721-3724).

Moreover, there is increasing evidence for a role of SST on immune cells and expression of SSTR5 on activated T lymphocytes (T. Talme, J. Ivanoff, M. Hägglund, R. J. J. van Neerven, A. Ivanoff and K. G. Sundqvist *Clin. Exp. Immunol.* 2001, 125, 71-79; D. Ferone, P. M. van Hagen, C. Semino, V. A. Dalm, A. Barreca, A. Colao, S. W. J. Lamberts, F. Minuto and L. J. Hofland *Dig. Liver Dis.* 2004, 36, S68-77; C. E. Ghamrawy, C. Rabourdin-Combe and S. Krantic *Peptides* 1999, 20, 305-311). Consequently, SSTR5 antagonists could also prove valuable in treating diseases characterized by a disturbed immune system, such as inflammatory bowel disease.

SUMMARY OF THE INVENTION

In an embodiment of the present invention, provided is a compound of formula (I):

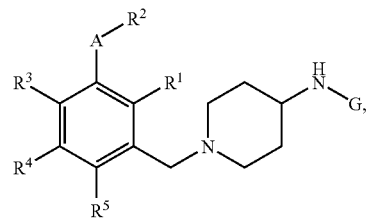

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, halogen-$C_{1-7}$-alkoxy, —C(O)OR$^6$, wherein R$^6$ is $C_{1-7}$-alkyl, amino, pyrrolyl, unsubstituted phenyl or phenyl substituted by one to three groups independently selected from $C_{1-7}$-alkyl, halogen and $C_{1-7}$-alkoxy;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—C(CH$_3$)$_2$—CH=CH—;

$R^5$ is selected from the group consisting of hydrogen, halogen and $C_{1-7}$-alkoxy;

G is selected from the groups

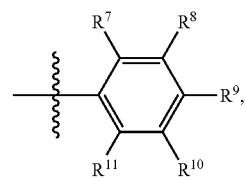

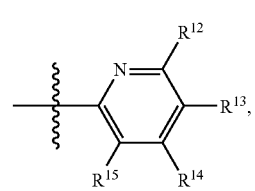

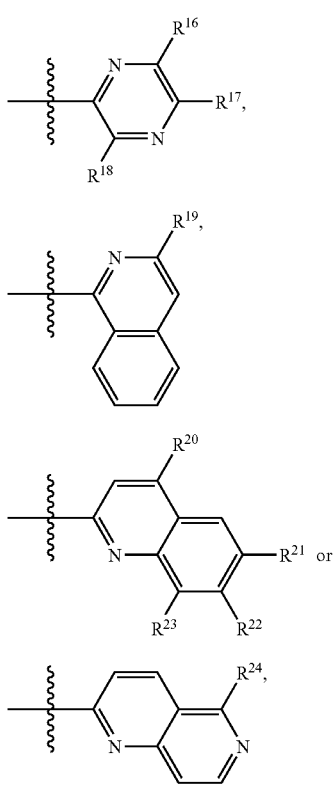

wherein
R$^7$ and R$^{11}$ are hydrogen;
R$^8$ and R$^{10}$ independently from each other are hydrogen or —NH—C(O)—R$^{25}$, wherein R$^{25}$ is C$_{1-7}$-alkyl;
R$^9$ is selected from the group consisting of hydrogen, C$_{1-7}$-alkyl, halogen, halogen-C$_{1-7}$-alkyl, cyano, —C(O)OR$^{26}$, wherein R$^{26}$ is hydrogen or C$_{1-7}$-alkyl, —(CH$_2$)$_m$—S(O)$_2$—NH—R$^{27}$, wherein m is 0 or 1 and R$^{27}$ is selected from C$_{1-7}$-alkyl, unsubstituted heteroaryl and heteroaryl substituted by C$_{1-7}$-alkyl; and —NH—S(O)$_2$—R$^{28}$, wherein R$^{28}$ is C$_{1-7}$-alkyl; or
or R$^8$ and R$^9$ are bonded to each other to form a ring together with the carbon atoms they are attached to and R$^8$ and R$^9$ together are —CH$_2$—S(O)$_2$—CH$_2$—;
R$^{12}$ is selected from the group consisting of hydrogen, C$_{1-7}$-alkyl, halogen and amino;
R$^{13}$ is selected from the group consisting of hydrogen, C$_{1-7}$-alkyl, halogen, halogen-C$_{1-7}$-alkyl, cyano, nitro, phenyl, tetrazolyl, benzoimidazolyl, —COOR$^{29}$, wherein R$^{29}$ is hydrogen or C$_{1-7}$-alkyl, hydroxy-C$_{1-7}$-alkoxy, cyano-C$_{1-7}$-alkoxy, —CONHR$^{30}$, wherein R$^{30}$ is selected from the group consisting of hydrogen, C$_{1-7}$-alkyl, C$_{3-7}$-cycloalkyl, hydroxy-C$_{1-7}$-alkyl, C$_{1-7}$-alkoxy-C$_{1-7}$-alkyl, halogen-C$_{1-7}$-alkyl, carboxy-C$_{1-7}$-alkyl, —(CH$_2$)$_n$—NH—C(O)—R$^{31}$, wherein n is 1 or 2 and R$^{31}$ is C$_{1-7}$-alkyl, —S(O)$_2$—R$^{33}$, wherein R$^{33}$ is C$_{1-7}$-alkyl, —O—S(O)$_2$—R$^{34}$, wherein R$^{34}$ is C$_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and C$_{1-7}$-alkanoyl;
R$^{14}$ is selected from the group consisting of hydrogen, C$_{1-7}$-alkyl, C$_{1-7}$-alkoxy, C$_{1-7}$-alkoxy-C$_{1-7}$-alkyl, cyano, carbamoyl, —COOR$^{35}$, wherein R$^{35}$ is hydrogen or C$_{1-7}$-alkyl, halogen and halogen-C$_{1-7}$-alkyl;
R$^{15}$ is selected from the group consisting of hydrogen, cyano, halogen and halogen-C$_{1-7}$-alkyl;
R$^{16}$ and R$^{18}$ are hydrogen;
R$^{17}$ is carbamoyl or —COOR$^{32}$, wherein R$^{32}$ is hydrogen or C$_{1-7}$-alkyl;
R$^{19}$ is hydrogen or halogen;
R$^{20}$ is selected from the group consisting of hydrogen, C$_{1-7}$-alkyl, C$_{1-7}$-alkoxy, C$_{1-7}$-alkoxy-C$_{1-7}$-alkyl and halogen;
R$^{21}$, R$^{22}$ and R$^{23}$ independently from each other are hydrogen or halogen;
R$^{24}$ is hydrogen or C$_{1-7}$-alkyl;
and pharmaceutically acceptable salts thereof.

In another embodiment of the present invention, provided is a process for the manufacture of compounds according to formula I, comprising the steps of:
a) reacting a compound of the general formula

G-X      II wherein G is as defined above and G is a leaving group,
with a compound of the formula

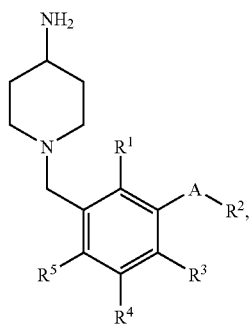
III wherein A and R$^1$ to R$^5$ are as defined above,
to obtain a compound of the formula

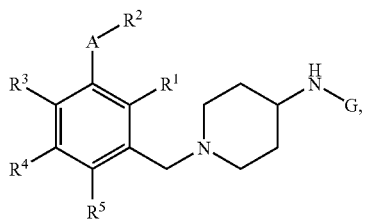
I and, if desired, converting the compound of formula I into a pharmaceutically acceptable salt; or, alternatively,
b) reacting a compound of the general formula

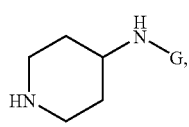
IV wherein G is as defined above, with an aldehyde of the formula

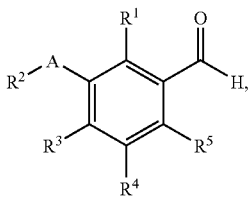

wherein A and $R^1$ to $R^5$ are as defined above,
by employing a reducing agent to obtain a compound of the formula

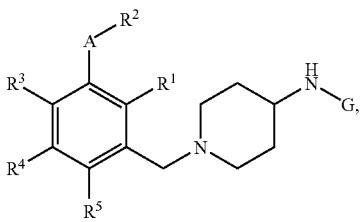

and, if desired, converting the compound of formula I into a pharmaceutically acceptable salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment of diseases which are associated with the modulation of SST receptors subtype 5, comprising the step of administering a therapeutically effective amount of a compound according to formula I to a human being or animal in need thereof.

DETAILED DESCRIPTION

Provided herein are selective, directly acting SSTR5 antagonists. Such antagonists are useful as therapeutically active substances, particularly in the treatment and/or prevention of diseases which are associated with the modulation of SST receptors subtype 5.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched $C_1$-$C_7$-alkyl groups are methyl, ethyl, propyl, isopropyl, butyl, isobutyl, tert-butyl, the isomeric pentyls, the isomeric hexyls and the isomeric heptyls, preferably methyl, ethyl and isopropyl, and most preferred the groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl(allyl).

The term "cycloalkyl" or "$C_{3-7}$-cycloalkyl" refers to a monovalent carbocyclic radical of three to seven, preferably three to five carbon atoms. This term is further exemplified by radicals such as cyclopropyl, cyclobutyl, cyclopentyl, cyclohexyl and cycloheptyl, with cyclobutyl being especially preferred.

The term "alkoxy" refers to the group R'—O—, wherein R' is alkyl. The term "lower alkoxy" or "$C_{1-7}$-alkoxy" refers to the group R'—O—, wherein R' is lower alkyl and the term "lower alkyl" has the previously given significance. Examples of lower alkoxy groups are e.g., methoxy, ethoxy, n-propoxy, isopropoxy, n-butoxy, iso-butoxy, sec-butoxy and tert-butoxy, preferably methoxy and ethoxy and most preferred the groups specifically exemplified herein.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, difluoroethyl, fluoromethyl and chloromethyl, with trifluoromethyl and difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl, but also groups having two hydroxy groups such as 1,3-dihydroxy-2-propyl.

The term "lower hydroxyalkoxy" or "hydroxy-$C_{1-7}$-alkoxy" refers to lower alkoxy groups as defined above wherein at least one of the hydrogen atoms of the lower alkoxy group is replaced by a hydroxy group. Examples of lower hydroxyalkoxy groups are hydroxymethoxy or hydroxyethoxy, but also dihydroxyalkoxy groups such as 2,3-dihydroxy-propyl-1-oxy.

The term "heteroaryl" refers to an aromatic 5- or 6-membered ring which can comprise one, two or three atoms selected from nitrogen, oxygen and/or sulphur. Examples of heteroaryl groups are furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, or pyrrolyl. The heteroaryl group can optionally be mono- or disubstituted by lower alkyl. The term "heteroaryl" also includes bicyclic aromatic moieties having 9 to 10 ring atoms with 1 to 3 heteroatoms such as benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, tetrazolyl and benzoimidazolyl which groups can optionally be mono- or disubstituted by lower alkyl. Especially preferred is isoxazolyl which can optionally be substituted by lower alkyl.

The term "heterocyclyl" in general refers to a saturated or partly unsaturated ring which can comprise one, two or three atoms selected from nitrogen, oxygen and/or sulphur. Examples of heterocyclyl rings include aziridinyl, azetidinyl, pyrrolidinyl, piperidinyl, tetrahydropyridyl, azepinyl, piperazinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, oxiranyl, oxetanyl, dihydropyranyl, tetrahydropyranyl and thiomorpholinyl. Preferred heterocyclyl groups are pyrrolidinyl, piperidinyl, piperazinyl and morpholinyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "carbamoyl" refers to the group —CO—NH$_2$.

The term "carboxy" refers to the group —COOH.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula I

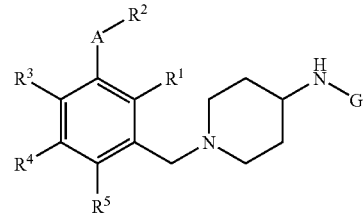

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, halogen-$C_{1-7}$-alkoxy, —C(O)OR$^6$, wherein R$^6$ is $C_{1-7}$-alkyl, amino, pyrrolyl, unsubstituted phenyl or phenyl substituted by one to three groups independently selected from $C_{1-7}$-alkyl, halogen and $C_{1-7}$-alkoxy;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—C(CH$_3$)$_2$—CH=CH—;

$R^5$ is selected from the group consisting of hydrogen, halogen and $C_{1-7}$-alkoxy;

G is selected from the groups

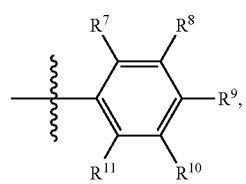

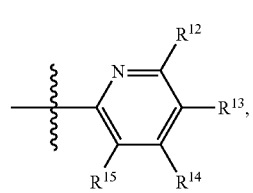

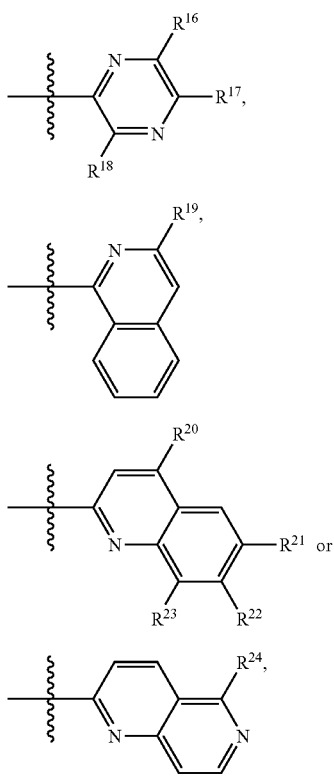

wherein
R$^7$ and R$^{11}$ are hydrogen;
R$^8$ and R$^{10}$ independently from each other are hydrogen or —NH—C(O)—R$^{25}$, wherein R$^{25}$ is C$_{1-7}$-alkyl;
R$^9$ is selected from the group consisting of hydrogen, C$_{1-7}$-alkyl, halogen, halogen-C$_{1-7}$-alkyl, cyano, —C(O)OR$^{26}$, wherein R$^{26}$ is hydrogen or C$_{1-7}$-alkyl, —(CH$_2$)$_m$—S(O)$_2$—NH—R$^{27}$, wherein m is 0 or 1 and R$^{27}$ is selected from C$_{1-7}$-alkyl, unsubstituted heteroaryl and heteroaryl substituted by C$_{1-7}$-alkyl; and
—NH—S(O)$_2$—R$^{28}$, wherein R$^{28}$ is C$_{1-7}$-alkyl; or
or R$^8$ and R$^9$ are bonded to each other to form a ring together with the carbon atoms they are attached to and R$^8$ and R$^9$ together are —CH$_2$—S(O)$_2$—CH$_2$—;
R$^{12}$ is selected from the group consisting of hydrogen, C$_{1-7}$-alkyl, halogen and amino;
R$^{13}$ is selected from the group consisting of hydrogen, C$_{1-7}$-alkyl, halogen, halogen-C$_{1-7}$-alkyl, cyano, nitro, phenyl, tetrazolyl, benzoimidazolyl, —COOR$^{29}$, wherein R$^{29}$ is hydrogen or C$_{1-7}$-alkyl, hydroxy-C$_{1-7}$-alkoxy, cyano-C$_{1-7}$-alkoxy, —CONHR$^{30}$, wherein R$^{30}$ is selected from the group consisting of hydrogen, C$_{1-7}$-alkyl, C$_{3-7}$-cycloalkyl, hydroxy-C$_{1-7}$-alkyl, C$_{1-7}$-alkoxy-C$_{1-7}$-alkyl, halogen-C$_{1-7}$-alkyl, carboxy-C$_{1-7}$-alkyl, —(CH$_2$)$_n$—NH—C(O)—R$^{31}$, wherein n is 1 or 2 and R$^{31}$ is C$_{1-7}$-alkyl, —S(O)$_2$—R$^{33}$, wherein R$^{33}$ is C$_{1-7}$-alkyl, —OS(O)$_2$—R$^{34}$, wherein R$^{34}$ is C$_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and C$_{1-7}$-alkanoyl;
R$^{14}$ is selected from the group consisting of hydrogen, C$_{1-7}$-alkyl, C$_{1-7}$-alkoxy, C$_{1-7}$-alkoxy-C$_{1-7}$-alkyl, cyano, carbamoyl, —COOR$^{35}$, wherein R$^{35}$ is hydrogen or C$_{1-7}$-alkyl, halogen and halogen-C$_{1-7}$-alkyl;
R$^{15}$ is selected from the group consisting of hydrogen, cyano, halogen and halogen-C$_{1-7}$-alkyl;
R$^{16}$ and R$^{18}$ are hydrogen;
R$^{17}$ is carbamoyl or —COOR$^{32}$, wherein R$^{32}$ is hydrogen or C$_{1-7}$-alkyl;
R$^{19}$ is hydrogen or halogen;
R$^{20}$ is selected from the group consisting of hydrogen, C$_{1-7}$-alkyl, C$_{1-7}$-alkoxy, C$_{1-7}$-alkoxy-C$_{1-7}$-alkyl and halogen;
R$^{21}$, R$^{22}$ and R$^{23}$ independently from each other are hydrogen or halogen;
R$^{24}$ is hydrogen or C$_{1-7}$-alkyl;
and pharmaceutically acceptable salts thereof.

Preferred compounds of formula I of the present invention are also those, wherein A is O.

Also preferred are compounds of formula I, wherein A is NH.

Furthermore, compounds of formula I according to the present invention are preferred, wherein R$^1$ is hydrogen.

Also preferred are compounds of formula I according to the invention, wherein R$^2$ is selected from the group consisting of C$_{2-7}$-alkyl, C$_{2-7}$-alkenyl and halogen-C$_{1-7}$-alkyl. Especially preferred are those compounds of formula I, wherein R$^2$ is selected from the group consisting of ethyl, propyl, isopropyl, allyl, 2-fluoroethyl, butyl and isobutyl, with those compounds, wherein R$^2$ is ethyl or isopropyl, being most preferred.

Further preferred compounds of formula I according to the present invention are those, wherein R$^3$ is selected from the group consisting of hydrogen, C$_{1-7}$-alkyl, hydroxy, C$_{1-7}$-alkoxy, halogen, halogen-C$_{1-7}$-alkoxy, —C(O)OR$^6$, wherein R$^6$ is C$_{1-7}$-alkyl, amino and pyrrolyl. More preferred are those compounds of formula I, wherein R$^3$ is selected from the group consisting of hydrogen, C$_{1-7}$-alkoxy and halogen, with those compounds, wherein R$^3$ is halogen, being especially preferred. Most preferably, R$^3$ is chloro.

Also preferred are compounds of formula I, wherein R$^3$ is unsubstituted phenyl or phenyl substituted by one to three groups independently selected from C$_{1-7}$-alkyl, halogen and C$_{1-7}$-alkoxy, with those compounds of formula I, wherein R$^3$ is phenyl substituted by halogen being more preferred, and with compounds of formula I, wherein R$^3$ is 4-fluorophenyl or 4-chlorophenyl being most preferred.

Furthermore, compounds of formula I of the present invention are preferred, wherein R$^4$ is selected from the group consisting of hydrogen, hydroxy, C$_{1-7}$-alkoxy and C$_{1-7}$-alkoxy-C$_{1-7}$-alkoxy.

Another group of preferred compounds of formula I according to the present invention are those, wherein R$^3$ and R$^4$ are bonded to each other to form a ring together with the carbon atoms they are attached to and R$^3$ and R$^4$ together are —O—C(CH$_3$)$_2$—CH=CH—. These are compounds of the formula Ix:

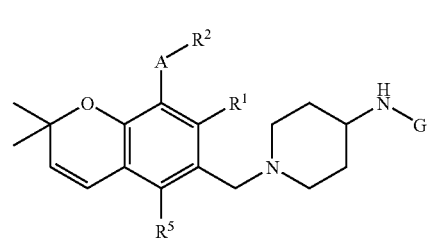

Ix

Furthermore, compounds of formula I according to the invention are preferred, wherein R$^5$ is hydrogen.

Especially preferred are compounds of formula I according to the present invention, wherein G is

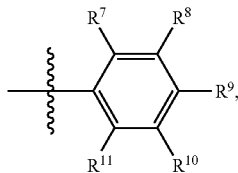

and wherein
R$^7$ and R$^{11}$ are hydrogen;
R$^8$ and R$^{10}$ independently from each other are hydrogen or —NH—C(O)—R$^{25}$, wherein R$^{25}$ is C$_{1-7}$-alkyl; and
R$^9$ is selected from the group consisting of hydrogen, C$_{1-7}$-alkyl, halogen, halogen-C$_{1-7}$-alkyl, cyano, —C(O)OR$^{26}$, wherein R$^{26}$ is hydrogen or C$_{1-7}$-alkyl, —(CH$_2$)$_m$—S(O)$_2$—NH—R$^{27}$, wherein m is 0 or 1 and R$^{27}$ is selected from C$_{1-7}$-alkyl, unsubstituted heteroaryl and heteroaryl substituted by C$_{1-7}$-alkyl; and
—NH—S(O)$_2$—R$^{28}$, wherein R$^{28}$ is C$_{1-7}$-alkyl; or
R$^8$ and R$^9$ are bonded to each other to form a ring together with the carbon atoms they are attached to and R$^8$ and R$^9$ together are —CH$_2$—S(O)$_2$—CH$_2$—.

Within this group, those compounds of formula I are preferred, wherein
R$^7$, R$^8$, R$^{10}$ and R$^{11}$ are hydrogen; and
R$^9$ is selected from the group consisting of C$_{1-7}$-alkyl, halogen, halogen-C$_{1-7}$-alkyl, cyano, —C(O)OR$^{26}$, wherein R$^{26}$ is hydrogen or C$_{1-7}$-alkyl, —(CH$_2$)$_m$—S(O)$_2$—NH—R$^{27}$, wherein m is 0 or 1 and R$^{27}$ is selected from C$_{1-7}$-alkyl, unsubstituted heteroaryl and heteroaryl substituted by C$_{1-7}$-alkyl; and
—NH—S(O)$_2$—R$^{28}$, wherein R$^{28}$ is C$_{1-7}$-alkyl.

Another group of preferred compounds of formula I according to the invention are those, wherein G is

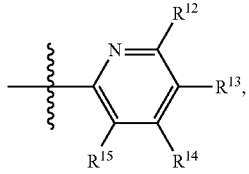

and wherein
R$^{12}$ is selected from the group consisting of hydrogen, C$_{1-7}$-alkyl, halogen and amino;
R$^{13}$ is selected from the group consisting of hydrogen, C$_{1-7}$-alkyl, halogen, halogen-C$_{1-7}$-alkyl, cyano, nitro, phenyl, tetrazolyl, benzoimidazolyl, —COOR$^{29}$, wherein R$^{29}$ is hydrogen or C$_{1-7}$-alkyl, hydroxy-C$_{1-7}$-alkoxy, cyano-C$_{1-7}$-alkoxy, —CONHR$^{30}$, wherein R$^{30}$ is selected from the group consisting of hydrogen, C$_{1-7}$-alkyl, C$_{3-7}$-cycloalkyl, hydroxy-C$_{1-7}$-alkyl, C$_{1-7}$-alkoxy-C$_{1-7}$-alkyl, halogen-C$_{1-7}$-alkyl, carboxy-C$_{1-7}$-alkyl, —(CH$_2$)$_n$—NH—C(O)—R$^{31}$, wherein n is 1 or 2 and R$^{31}$ is C$_{1-7}$-alkyl, —S(O)$_2$—R$^{33}$, wherein R$^{33}$ is C$_{1-7}$-alkyl, —O—S(O)$_2$—R$^{34}$, wherein R$^{34}$ is C$_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and C$_{1-7}$-alkanoyl;
R$^{14}$ is selected from the group consisting of hydrogen, C$_{1-7}$-alkyl, C$_{1-7}$-alkoxy, C$_{1-7}$-alkoxy-C$_{1-7}$-alkyl, cyano, carbamoyl, —COOR$^{35}$, wherein R$^{35}$ is hydrogen or C$_{1-7}$-alkyl, halogen and halogen-C$_{1-7}$-alkyl; and
R$^{15}$ is selected from the group consisting of hydrogen, cyano, halogen and halogen-C$_{1-7}$-alkyl.

Within this group, those compounds are preferred, wherein
R$^{12}$, R$^{14}$ and R$^{13}$ are hydrogen; and
R$^{13}$ is selected from the group consisting of C$_{1-7}$-alkyl, halogen, halogen-C$_{1-7}$-alkyl, cyano, nitro, phenyl, tetrazolyl, benzoimidazolyl, —COOR$^{29}$, wherein R$^{29}$ is hydrogen or C$_{1-7}$-alkyl, —CONHR$^{30}$, wherein R$^{30}$ is selected from the group consisting of hydrogen, C$_{1-7}$-alkyl, C$_{3-7}$-cycloalkyl, hydroxy-C$_{1-7}$-alkyl, C$_{1-7}$-alkoxy-C$_{1-7}$-alkyl, halogen-C$_{1-7}$-alkyl, carboxy-C$_{1-7}$-alkyl, —(CH$_2$)$_n$—NH—C(O)—R$^{31}$, wherein n is 1 or 2 and R$^{31}$ is C$_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and C$_{1-7}$-alkanoyl.

A further group of preferred compounds of formula I according to the invention are those, wherein G is

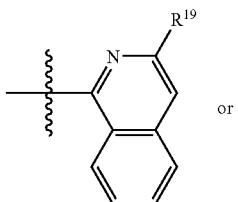

and wherein
R$^{16}$ and R$^{18}$ are hydrogen; and
R$^{17}$ is carbamoyl or —COOR$^{32}$, wherein R$^{32}$ is hydrogen or C$_{1-7}$-alkyl.

Also preferred are compounds of formula I according to the invention, wherein G is a group selected from

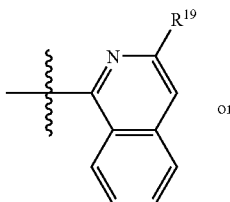

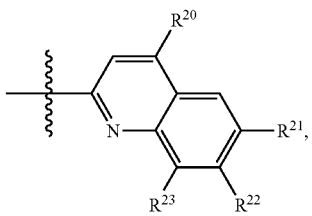

and wherein
R$^{19}$ is hydrogen or halogen;
R$^{20}$ is selected from the group consisting of hydrogen, C$_{1-7}$-alkyl, C$_{1-7}$-alkoxy, C$_{1-7}$-alkoxy-C$_{1-7}$-alkyl and halogen; and $R^{21}$, $R^{22}$ and $R^{23}$ independently from each other are hydrogen or halogen.

Another group of preferred compounds are those, wherein G is

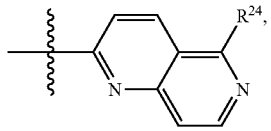

G6 and wherein $R^{24}$ is hydrogen or $C_{1-7}$-alkyl.

In one aspect, the invention relates to compounds of formula I having the formula

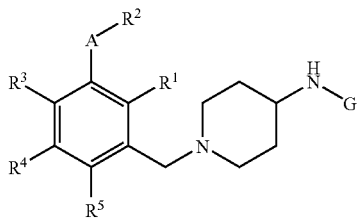

Ia wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, halogen-$C_{1-7}$-alkoxy, —C(O)OR$^6$, wherein $R^6$ is $C_{1-7}$-alkyl, amino and pyrrolyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—C(CH$_3$)$_2$—CH═CH—;

$R^5$ is selected from the group consisting of hydrogen, halogen and $C_{1-7}$-alkoxy;

G is selected from the groups

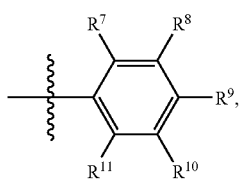

G1

-continued

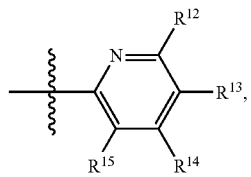

G2

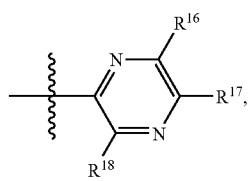

G3

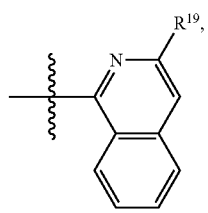

G4

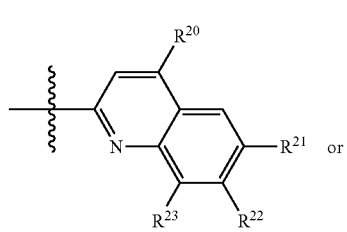

G5

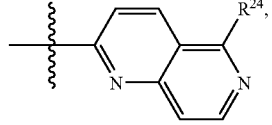 or

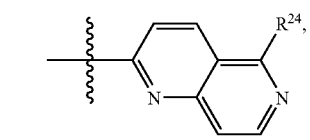

G6 wherein $R^7$ and $R^{11}$ are hydrogen;

$R^8$ and $R^{11}$ independently from each other are hydrogen or —NH—C(O)—$R^{25}$, wherein $R^{25}$ is $C_{1-7}$-alkyl;

$R^9$ is selected from the group consisting of hydrogen, $C_{1-7}$-alkyl, halogen, halogen-$C_{1-7}$-alkyl, cyano, —C(O)OR$^{26}$, wherein $R^{26}$ is hydrogen or $C_{1-7}$-alkyl, —(CH$_2$)$_m$—S(O)$_2$—NH—$R^{27}$, wherein m is 0 or 1 and $R^{27}$ is selected from $C_{1-7}$-alkyl, unsubstituted heteroaryl and heteroaryl substituted by $C_{1-7}$-alkyl; and —NH—S(O)$_2$—$R^{28}$, wherein $R^{28}$ is $C_{1-7}$-alkyl; or or $R^8$ and $R^9$ are bonded to each other to form a ring together with the carbon atoms they are attached to and $R^8$ and $R^9$ together are —CH$_2$—S(O)$_2$—CH$_2$—;

$R^{12}$ is selected from the group consisting of hydrogen, $C_{1-7}$-alkyl, halogen and amino;

$R^{13}$ is selected from the group consisting of hydrogen, $C_{1-7}$-alkyl, halogen, halogen-$C_{1-7}$-alkyl, cyano, nitro, phenyl, tetrazolyl, benzoimidazolyl, —COOR$^{29}$, wherein $R^{29}$ is hydrogen or $C_{1-7}$-alkyl, —CONHR$^{30}$, wherein $R^{30}$ is selected from the group consisting of hydrogen, $C_{1-7}$-alkyl, $C_{3-7}$-cycloalkyl, hydroxy-$C_{1-7}$-alkyl, $C_{1-7}$-alkoxy-$C_{1-7}$-alkyl, halogen-$C_{1-7}$-alkyl, carboxy-$C_{1-7}$-alkyl, —(CH$_2$)$_n$—NH—C(O)—$R^{31}$, wherein n is 1 or 2 and $R^{31}$ is $C_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and $C_{1-7}$-alkanoyl;

$R^{14}$ is selected from the group consisting of hydrogen, $C_{1-7}$-alkyl, $C_{1-7}$-alkoxy, $C_{1-7}$-alkoxy-$C_{1-7}$-alkyl, cyano, carbamoyl, halogen and halogen-$C_{1-7}$-alkyl;

$R^{15}$ is selected from the group consisting of hydrogen, cyano, halogen and halogen-$C_{1-7}$-alkyl;

$R^{16}$ and $R^{18}$ are hydrogen;

$R^{17}$ is carbamoyl or —COOR$^{32}$, wherein $R^{32}$ is hydrogen or $C_{1-7}$-alkyl;

$R^{19}$ is hydrogen or halogen;

$R^{20}$ is selected from the group consisting of hydrogen, $C_{1-7}$-alkyl, $C_{1-7}$-alkoxy, $C_{1-7}$-alkoxy-$C_{1-7}$-alkyl and halogen;

$R^{21}$, $R^{22}$ and $R^{23}$ independently from each other are hydrogen or halogen;

$R^{24}$ is hydrogen or $C_{1-7}$-alkyl;

and pharmaceutically acceptable salts thereof.

Examples of preferred compounds of formula I are the following:

4-[1-(3-ethoxy-4-methoxy-benzyl)-piperidin-4-ylamino]-benzonitrile,
4-[1-(4-chloro-3-ethoxy-benzyl)-piperidin-4-ylamino]-benzonitrile,
N-{3-[1-(4-chloro-3-ethoxy-benzyl)-piperidin-4-ylamino]-phenyl}-acetamide,
N-{3-[1-(3,5-diethoxy-4-fluoro-benzyl)-piperidin-4-ylamino]-phenyl}-acetamide,
[1-(3-ethoxy-4-methoxy-benzyl)-piperidin-4-yl]-(4-ethyl-phenyl)-amine,
C-{4-[1-(3-ethoxy-4-methoxy-benzyl)-piperidin-4-ylamino]-phenyl}-N-methyl-methanesulfonamide,
(2,2-dioxo-2,3-dihydro-1H-2λ6-benzo[c]thiophen-5-yl)-[1-(3-ethoxy-4-methoxy-benzyl)-piperidin-4-yl]-amine,
4-[1-(3-ethoxy-4-methoxy-benzyl)-piperidin-4-ylamino]-benzoic acid,
4-[1-(3-ethoxy-4-methoxy-benzyl)-piperidin-4-ylamino]-N-(5-methyl-isoxazol-3-yl)-benzenesulfonamide,
N-{4-[1-(3-ethoxy-4-methoxy-benzyl)-piperidin-4-ylamino]-phenyl}-methanesulfonamide,
[5-(1H-benzoimidazol-2-yl)-pyridin-2-yl]-[1-(3-ethoxy-4-methoxy-benzyl)-piperidin-4-yl]-amine,
(7-chloro-4-methoxymethyl-quinolin-2-yl)-[1-(3-ethoxy-4-methoxy-benzyl)-piperidin-4-yl]-amine,
[1-(3-ethoxy-4-methoxy-benzyl)-piperidin-4-yl]-(6-fluoro-quinolin-2-yl)-amine,
6-[1-(3-ethoxy-4-methoxy-benzyl)-piperidin-4-ylamino]-nicotinonitrile,
[1-(3-ethoxy-4-methoxy-benzyl)-piperidin-4-yl]-(5-trifluoromethyl-pyridin-2-yl)-amine,
(6-chloro-pyridin-2-yl)-[1-(3-ethoxy-4-methoxy-benzyl)-piperidin-4-yl]-amine,
6-[1-(3-ethoxy-4-methoxy-benzyl)-piperidin-4-ylamino]-nicotinic acid ethyl ester,
6-[1-(3-ethoxy-4-methoxy-benzyl)-piperidin-4-ylamino]-nicotinic acid methyl ester,
[1-(3-ethoxy-4-methoxy-benzyl)-piperidin-4-yl]-(5-nitro-pyridin-2-yl)-amine,
(5-bromo-pyridin-2-yl)-[1-(3-ethoxy-4-methoxy-benzyl)-piperidin-4-yl]-amine,
[1-(3-ethoxy-4-methoxy-benzyl)-piperidin-4-yl]-(6-methyl-5-nitro-pyridin-2-yl)-amine,
$N^6$-[1-(3-ethoxy-4-methoxy-benzyl)-piperidin-4-yl]-3-nitro-pyridine-2,6-diamine,
2-chloro-6-[1-(3-ethoxy-4-methoxy-benzyl)-piperidin-4-ylamino]-isonicotinic acid methyl ester,
2-[1-(3-ethoxy-4-methoxy-benzyl)-piperidin-4-ylamino]-6-methyl-5-phenyl-nicotinonitrile,
2-chloro-6-[1-(3-ethoxy-4-methoxy-benzyl)-piperidin-4-ylamino]-5-fluoro-nicotinonitrile,
[1-(3-ethoxy-4-methoxy-benzyl)-piperidin-4-yl]-quinolin-2-yl-amine,
[1-(3-ethoxy-4-methoxy-benzyl)-piperidin-4-yl]-(5-methyl-[1,6]naphthyridin-2-yl)-amine,
{2-chloro-6-[1-(4-chloro-3-ethoxy-benzyl)-piperidin-4-ylamino]-pyridin-4-yl}-methanol,
6-[1-(4-chloro-3-ethoxy-benzyl)-piperidin-4-ylamino]-nicotinic acid methyl ester,
[1-(4-chloro-3-ethoxy-benzyl)-piperidin-4-yl]-(5-trifluoromethyl-pyridin-2-yl)-amine,
[1-(4-chloro-3-ethoxy-benzyl)-piperidin-4-yl]-(3-trifluoromethyl-pyridin-2-yl)-amine,
[1-(4-chloro-3-ethoxy-benzyl)-piperidin-4-yl]-(6-methyl-5-nitro-pyridin-2-yl)-amine,
$N^6$-[1-(4-chloro-3-ethoxy-benzyl)-piperidin-4-yl]-3-nitro-pyridine-2,6-diamine,
[1-(4-chloro-3-ethoxy-benzyl)-piperidin-4-yl]-(6-chloro-4-methoxymethyl-pyridin-2-yl)-amine,
2-[1-(4-chloro-3-ethoxy-benzyl)-piperidin-4-ylamino]-6-methyl-nicotinonitrile,
[1-(4-chloro-3-ethoxy-benzyl)-piperidin-4-yl]-(6-fluoro-quinolin-2-yl)-amine,
[1-(4-chloro-3-ethoxy-benzyl)-piperidin-4-yl]-(5-methyl-[1,6]naphthyridin-2-yl)-amine,
6-[1-(3-ethoxy-4-methyl-benzyl)-piperidin-4-ylamino]-nicotinonitrile,
6-[1-(3-ethoxy-4-fluoro-benzyl)-piperidin-4-ylamino]-nicotinonitrile,
6-[1-(4-chloro-3-ethoxy-benzyl)-piperidin-4-ylamino]-nicotinonitrile,
6-[1-(3-ethoxy-4-hydroxy-benzyl)-piperidin-4-ylamino]-nicotinonitrile,
6-[1-(3,5-diethoxy-benzyl)-piperidin-4-ylamino]-nicotinonitrile,
6-[1-(3,5-diisopropoxy-benzyl)-piperidin-4-ylamino]-nicotinonitrile,
6-[1-(3,5-diethoxy-4-fluoro-benzyl)-piperidin-4-ylamino]-nicotinonitrile,
6-[1-(4-chloro-3,5-diethoxy-benzyl)-piperidin-4-ylamino]-nicotinonitrile,
6-[1-(4-bromo-3,5-diethoxy-benzyl)-piperidin-4-ylamino]-nicotinonitrile,
6-[1-(4-amino-3,5-diethoxy-benzyl)-piperidin-4-ylamino]-nicotinonitrile,
6-[1-(3,5-diethoxy-4-pyrrol-1-yl-benzyl)-piperidin-4-ylamino]-nicotinonitrile,
6-[1-(3-ethoxy-4-methyl-benzyl)-piperidin-4-ylamino]-nicotinamide,
6-[1-(3-ethoxy-4-fluoro-benzyl)-piperidin-4-ylamino]-nicotinamide,
6-[1-(4-chloro-3-ethoxy-benzyl)-piperidin-4-ylamino]-nicotinamide,
6-[1-(3-ethoxy-4-hydroxy-benzyl)-piperidin-4-ylamino]-nicotinamide,
6-[1-(3-ethoxy-4-methoxy-benzyl)-piperidin-4-ylamino]-nicotinamide,
6-[1-(4-methoxy-3-propoxy-benzyl)-piperidin-4-ylamino]-nicotinamide,
6-[1-(3-isobutoxy-4-methoxy-benzyl)-piperidin-4-ylamino]-nicotinamide,
6-[1-(3,5-diethoxy-benzyl)-piperidin-4-ylamino]-nicotinamide,
6-[1-(3,5-diisopropoxy-benzyl)-piperidin-4-ylamino]-nicotinamide,
6-[1-(3,5-diethoxy-4-fluoro-benzyl)-piperidin-4-ylamino]-nicotinamide, 6-[1-(4-chloro-3,5-diethoxy-benzyl)-piperidin-4-ylamino]-nicotinamide,
6-[1-(4-amino-3,5-diethoxy-benzyl)-piperidin-4-ylamino]-nicotinamide,
6-[1-(3,5-diethoxy-4-pyrrol-1-yl-benzyl)-piperidin-4-ylamino]-nicotinamide,
6-[1-(3-ethoxy-4-methyl-benzyl)-piperidin-4-ylamino]-nicotinic acid,
6-[1-(3-ethoxy-4-fluoro-benzyl)-piperidin-4-ylamino]-nicotinic acid,
6-[1-(4-chloro-3-ethoxy-benzyl)-piperidin-4-ylamino]-nicotinic acid,
6-[1-(3-ethoxy-4-hydroxy-benzyl)-piperidin-4-ylamino]-nicotinic acid,
6-[1-(3-ethoxy-4-methoxy-benzyl)-piperidin-4-ylamino]-nicotinic acid,
6-[1-(3,5-diethoxy-benzyl)-piperidin-4-ylamino]-nicotinic acid,
6-[1-(3,5-diisopropoxy-benzyl)-piperidin-4-ylamino]-nicotinic acid,
6-[1-(3,5-diethoxy-4-fluoro-benzyl)-piperidin-4-ylamino]-nicotinic acid,
6-[1-(4-chloro-3,5-diethoxy-benzyl)-piperidin-4-ylamino]-nicotinic acid,
[1-(4-chloro-3-ethoxy-benzyl)-piperidin-4-yl]-[5-(1H-tetrazol-5-yl)-pyridin-2-yl]-amine,
[1-(3-ethoxy-4-methoxy-benzyl)-piperidin-4-yl]-[5-(1H-tetrazol-5-yl)-pyridin-2-yl]-amine,
[1-(3,5-diisopropoxy-benzyl)-piperidin-4-yl]-[5-(1H-tetrazol-5-yl)-pyridin-2-yl]-amine,
[1-(3,5-diethoxy-4-fluoro-benzyl)-piperidin-4-yl]-[5-(1H-tetrazol-5-yl)-pyridin-2-yl]-amine,
[1-(4-bromo-3,5-diethoxy-benzyl)-piperidin-4-yl]-[5-(1H-tetrazol-5-yl)-pyridin-2-yl]-amine,
[1-(3-ethoxy-4-methyl-benzyl)-piperidin-4-yl]-(5-trifluoromethyl-pyridin-2-yl)-amine,
[1-(4-chloro-3-ethoxy-benzyl)-piperidin-4-yl]-(5-trifluoromethyl-pyridin-2-yl)-amine,
[1-(3-ethoxy-4-methoxy-benzyl)-piperidin-4-yl]-(5-trifluoromethyl-pyridin-2-yl)-amine,
[1-(4-methoxy-3-propoxy-benzyl)-piperidin-4-yl]-(5-trifluoromethyl-pyridin-2-yl)-amine,
[1-(3,5-diethoxy-benzyl)-piperidin-4-yl]-(5-trifluoromethyl-pyridin-2-yl)-amine,
[1-(3,5-diethoxy-4-fluoro-benzyl)-piperidin-4-yl]-(5-trifluoromethyl-pyridin-2-yl)-amine,
[1-(3,5-diethoxy-4-iodo-benzyl)-piperidin-4-yl]-(5-trifluoromethyl-pyridin-2-yl)-amine,
[1-(3-ethoxy-4-iodo-5-methoxymethoxy-benzyl)-piperidin-4-yl]-(5-trifluoromethyl-pyridin-2-yl)-amine,
[1-(3,5-diethoxy-4-pyrrol-1-yl-benzyl)-piperidin-4-yl]-(5-trifluoromethyl-pyridin-2-yl)-amine,
6-[1-(4-chloro-3-ethoxy-benzyl)-piperidin-4-ylamino]-4-trifluoromethyl-nicotinic acid methyl ester,
6-[1-(3-ethoxy-4-hydroxy-benzyl)-piperidin-4-ylamino]-4-trifluoromethyl-nicotinic acid methyl ester,
6-[1-(3-ethoxy-4-methoxy-benzyl)-piperidin-4-ylamino]-4-trifluoromethyl-nicotinic acid methyl ester,
6-[1-(4-methoxy-3-propoxy-benzyl)-piperidin-4-ylamino]-4-trifluoromethyl-nicotinic acid methyl ester,
6-[1-(3-isobutoxy-4-methoxy-benzyl)-piperidin-4-ylamino]-4-trifluoromethyl-nicotinic acid methyl ester,
[1-(3-ethoxy-4-methyl-benzyl)-piperidin-4-yl]-quinolin-2-yl-amine,
[1-(3-ethoxy-4-fluoro-benzyl)-piperidin-4-yl]-quinolin-2-yl-amine,
[1-(4-chloro-3-ethoxy-benzyl)-piperidin-4-yl]-quinolin-2-yl-amine,
[1-(3-ethoxy-4-methoxy-benzyl)-piperidin-4-yl]-quinolin-2-yl-amine,
{1-[3-ethoxy-4-(1-ethyl-propoxy)-benzyl]-piperidin-4-yl}-quinolin-2-yl-amine,
[1-(4-methoxy-3-propoxy-benzyl)-piperidin-4-yl]-quinolin-2-yl-amine,
[1-(3-allyloxy-4-methoxy-benzyl)-piperidin-4-yl]-quinolin-2-yl-amine,
[1-(3-butoxy-4-methoxy-benzyl)-piperidin-4-yl]-quinolin-2-yl-amine,
[1-(3-isobutoxy-4-methoxy-benzyl)-piperidin-4-yl]-quinolin-2-yl-amine,
[1-(8-ethoxy-2,2-dimethyl-2H-chromen-6-ylmethyl)-piperidin-4-yl]-quinolin-2-yl-amine,
[1-(3,5-diethoxy-benzyl)-piperidin-4-yl]-quinolin-2-yl-amine,
3-isopropoxy-5-[4-(quinolin-2-ylamino)-piperidin-1-ylmethyl]-phenol,
[1-(3,5-diisopropoxy-benzyl)-piperidin-4-yl]-quinolin-2-yl-amine,
[1-(3,5-diethoxy-4-fluoro-benzyl)-piperidin-4-yl]-quinolin-2-yl-amine,
[1-(4-chloro-3,5-diethoxy-benzyl)-piperidin-4-yl]-quinolin-2-yl-amine,
[1-(4-bromo-3,5-diethoxy-benzyl)-piperidin-4-yl]-quinolin-2-yl-amine,
[1-(4-amino-3,5-diethoxy-benzyl)-piperidin-4-yl]-quinolin-2-yl-amine,
[1-(3,5-diethoxy-4-pyrrol-1-yl-benzyl)-piperidin-4-yl]-quinolin-2-yl-amine,
[1-(3-ethoxy-4-methyl-benzyl)-piperidin-4-yl]-(4-methyl-quinolin-2-yl)-amine,
[1-(3-ethoxy-4-fluoro-benzyl)-piperidin-4-yl]-(4-methyl-quinolin-2-yl)-amine,
[1-(4-chloro-3-ethoxy-benzyl)-piperidin-4-yl]-(4-methyl-quinolin-2-yl)-amine,
[1-(3-ethoxy-4-methoxy-benzyl)-piperidin-4-yl]-(4-methyl-quinolin-2-yl)-amine,
3-isopropoxy-5-[4-(4-methyl-quinolin-2-ylamino)-piperidin-1-ylmethyl]-phenol,
[1-(3,5-diisopropoxy-benzyl)-piperidin-4-yl]-(4-methyl-quinolin-2-yl)-amine,
[1-(3,5-diethoxy-4-fluoro-benzyl)-piperidin-4-yl]-(4-methyl-quinolin-2-yl)-amine,
[1-(4-chloro-3,5-diethoxy-benzyl)-piperidin-4-yl]-(4-methyl-quinolin-2-yl)-amine,
[1-(4-bromo-3,5-diethoxy-benzyl)-piperidin-4-yl]-(4-methyl-quinolin-2-yl)-amine,
[1-(4-amino-3,5-diethoxy-benzyl)-piperidin-4-yl]-(4-methyl-quinolin-2-yl)-amine,
[1-(3,5-diethoxy-4-pyrrol-1-yl-benzyl)-piperidin-4-yl]-(4-methyl-quinolin-2-yl)-amine,
(4-chloro-quinolin-2-yl)-[1-(3-ethoxy-4-methyl-benzyl)-piperidin-4-yl]-amine,
[1-(4-chloro-3-ethoxy-benzyl)-piperidin-4-yl]-(4-chloro-quinolin-2-yl)-amine,
[1-(4-chloro-3,5-diethoxy-benzyl)-piperidin-4-yl]-(4-chloro-quinolin-2-yl)-amine,
[1-(4-amino-3,5-diethoxy-benzyl)-piperidin-4-yl]-(4-chloro-quinolin-2-yl)-amine,
(8-chloro-quinolin-2-yl)-[1-(3-ethoxy-4-methyl-benzyl)-piperidin-4-yl]-amine,
[1-(4-chloro-3-ethoxy-benzyl)-piperidin-4-yl]-(8-chloro-quinolin-2-yl)-amine, 4-[4-(8-chloro-quinolin-2-ylamino)-piperidin-1-ylmethyl]-2-ethoxy-phenol,
(8-chloro-quinolin-2-yl)-[1-(3-ethoxy-4-methoxy-benzyl)-piperidin-4-yl]-amine,
(8-chloro-quinolin-2-yl)-{1-[3-ethoxy-4-(1-ethyl-propoxy)-benzyl]-piperidin-4-yl}-amine,
(8-chloro-quinolin-2-yl)-[1-(4-methoxy-3-propoxy-benzyl)-piperidin-4-yl]-amine,
[1-(3-allyloxy-4-methoxy-benzyl)-piperidin-4-yl]-(8-chloro-quinolin-2-yl)-amine,
[1-(3-butoxy-4-methoxy-benzyl)-piperidin-4-yl]-(8-chloro-quinolin-2-yl)-amine,
(8-chloro-quinolin-2-yl)-[1-(3-isobutoxy-4-methoxy-benzyl)-piperidin-4-yl]-amine,
(8-chloro-quinolin-2-yl)-[1-(8-ethoxy-2,2-dimethyl-2H-chromen-6-ylmethyl)-piperidin-4-yl]-amine,
(8-chloro-quinolin-2-yl)-[1-(3,5-diethoxy-benzyl)-piperidin-4-yl]-amine,
4-[4-(8-chloro-quinolin-2-ylamino)-piperidin-1-ylmethyl]-2,6-diethoxy-benzoic acid ethyl ester,
(8-chloro-quinolin-2-yl)-[1-(3,5-diethoxy-4-fluoro-benzyl)-piperidin-4-yl]-amine,
[1-(4-bromo-3,5-diethoxy-benzyl)-piperidin-4-yl]-(8-chloro-quinolin-2-yl)-amine,
(8-chloro-quinolin-2-yl)-[1-(3,5-diethoxy-4-pyrrol-1-yl-benzyl)-piperidin-4-yl]-amine,
[1-(3-ethoxy-4-methyl-benzyl)-piperidin-4-yl]-isoquinolin-1-yl-amine,
[1-(3-ethoxy-4-fluoro-benzyl)-piperidin-4-yl]-isoquinolin-1-yl-amine,
[1-(4-chloro-3-ethoxy-benzyl)-piperidin-4-yl]-isoquinolin-1-yl-amine,
[1-(3-ethoxy-4-methoxy-benzyl)-piperidin-4-yl]-isoquinolin-1-yl-amine,
isoquinolin-1-yl-[1-(4-methoxy-3-propoxy-benzyl)-piperidin-4-yl]-amine,
[1-(3-allyloxy-4-methoxy-benzyl)-piperidin-4-yl]-isoquinolin-1-yl-amine,
[1-(3-butoxy-4-methoxy-benzyl)-piperidin-4-yl]-isoquinolin-1-yl-amine,
[1-(3-isobutoxy-4-methoxy-benzyl)-piperidin-4-yl]-isoquinolin-1-yl-amine,
[1-(8-ethoxy-2,2-dimethyl-2H-chromen-6-ylmethyl)-piperidin-4-yl]-isoquinolin-1-yl-amine,
[1-(3,5-diethoxy-benzyl)-piperidin-4-yl]-isoquinolin-1-yl-amine,
3-isopropoxy-5-[4-(isoquinolin-1-ylamino)-piperidin-1-ylmethyl]-phenol,
[1-(3,5-diisopropoxy-benzyl)-piperidin-4-yl]-isoquinolin-1-yl-amine,
[1-(3,5-diethoxy-4-fluoro-benzyl)-piperidin-4-yl]-isoquinolin-1-yl-amine,
[1-(4-chloro-3,5-diethoxy-benzyl)-piperidin-4-yl]-isoquinolin-1-yl-amine,
[1-(4-bromo-3,5-diethoxy-benzyl)-piperidin-4-yl]-isoquinolin-1-yl-amine,
[1-(3,5-diethoxy-4-pyrrol-1-yl-benzyl)-piperidin-4-yl]-isoquinolin-1-yl-amine,
(3-chloro-isoquinolin-1-yl)-[1-(3-ethoxy-4-methyl-benzyl)-piperidin-4-yl]-amine,
(3-chloro-isoquinolin-1-yl)-[1-(3-ethoxy-4-fluoro-benzyl)-piperidin-4-yl]-amine,
[1-(4-chloro-3-ethoxy-benzyl)-piperidin-4-yl]-(3-chloro-isoquinolin-1-yl)-amine,
4-[4-(3-chloro-isoquinolin-1-ylamino)-piperidin-1-ylmethyl]-2-ethoxy-phenol,
(3-chloro-isoquinolin-1-yl)-[1-(3-ethoxy-4-methoxy-benzyl)-piperidin-4-yl]-amine,
(3-chloro-isoquinolin-1-yl)-[1-(4-difluoromethoxy-3-ethoxy-benzyl)-piperidin-4-yl]-amine,
(3-chloro-isoquinolin-1-yl)-[1-(3-ethoxy-4-isopropoxy-benzyl)-piperidin-4-yl]-amine,
(3-chloro-isoquinolin-1-yl)-[1-(3-ethoxy-4-isobutoxy-benzyl)-piperidin-4-yl]-amine,
(3-chloro-isoquinolin-1-yl)-[1-(4-methoxy-3-propoxy-benzyl)-piperidin-4-yl]-amine,
[1-(3-allyloxy-4-methoxy-benzyl)-piperidin-4-yl]-(3-chloro-isoquinolin-1-yl)-amine,
[1-(3-butoxy-4-methoxy-benzyl)-piperidin-4-yl]-(3-chloro-isoquinolin-1-yl)-amine,
(3-chloro-isoquinolin-1-yl)-[1-(3-isobutoxy-4-methoxy-benzyl)-piperidin-4-yl]-amine,
(3-chloro-isoquinolin-1-yl)-[1-(8-ethoxy-2,2-dimethyl-2H-chromen-6-ylmethyl)-piperidin-4-yl]-amine,
(3-chloro-isoquinolin-1-yl)-[1-(3,5-diethoxy-benzyl)-piperidin-4-yl]-amine,
(3-chloro-isoquinolin-1-yl)-[1-(3,5-diethoxy-4-fluoro-benzyl)-piperidin-4-yl]-amine,
[1-(4-chloro-3,5-diethoxy-benzyl)-piperidin-4-yl]-(3-chloro-isoquinolin-1-yl)-amine,
[1-(4-bromo-3,5-diethoxy-benzyl)-piperidin-4-yl]-(3-chloro-isoquinolin-1-yl)-amine,
[1-(4-amino-3,5-diethoxy-benzyl)-piperidin-4-yl]-(3-chloro-isoquinolin-1-yl)-amine,
5-[1-(3-ethoxy-4-methyl-benzyl)-piperidin-4-ylamino]-pyrazine-2-carboxylic acid methyl ester,
5-[1-(3-ethoxy-4-fluoro-benzyl)-piperidin-4-ylamino]-pyrazine-2-carboxylic acid methyl ester,
5-[1-(4-chloro-3-ethoxy-benzyl)-piperidin-4-ylamino]-pyrazine-2-carboxylic acid methyl ester,
5-[1-(3-ethoxy-4-hydroxy-benzyl)-piperidin-4-ylamino]-pyrazine-2-carboxylic acid methyl ester,
5-[1-(3-ethoxy-4-methoxy-benzyl)-piperidin-4-ylamino]-pyrazine-2-carboxylic acid methyl ester,
5-[1-(3-ethoxy-4-isopropoxy-benzyl)-piperidin-4-ylamino]-pyrazine-2-carboxylic acid methyl ester,
5-[1-(4-methoxy-3-propoxy-benzyl)-piperidin-4-ylamino]-pyrazine-2-carboxylic acid methyl ester,
5-{1-[3-(2-fluoro-ethoxy)-4-methoxy-benzyl]-piperidin-4-ylamino}-pyrazine-2-carboxylic acid methyl ester,
5-[1-(3-isobutoxy-4-methoxy-benzyl)-piperidin-4-ylamino]-pyrazine-2-carboxylic acid methyl ester,
5-[1-(8-ethoxy-2,2-dimethyl-2H-chromen-6-ylmethyl)-piperidin-4-ylamino]-pyrazine-2-carboxylic acid methyl ester,
5-[1-(3,5-diethoxy-benzyl)-piperidin-4-ylamino]-pyrazine-2-carboxylic acid methyl ester,
5-[1-(3,5-diisopropoxy-benzyl)-piperidin-4-ylamino]-pyrazine-2-carboxylic acid methyl ester,
5-[1-(3,5-diethoxy-4-fluoro-benzyl)-piperidin-4-ylamino]-pyrazine-2-carboxylic acid methyl ester,
5-[1-(4-chloro-3,5-diethoxy-benzyl)-piperidin-4-ylamino]-pyrazine-2-carboxylic acid methyl ester,
5-[1-(4-bromo-3,5-diethoxy-benzyl)-piperidin-4-ylamino]-pyrazine-2-carboxylic acid methyl ester,
5-[1-(4-amino-3,5-diethoxy-benzyl)-piperidin-4-ylamino]-pyrazine-2-carboxylic acid methyl ester,
5-[1-(3,5-diethoxy-4-pyrrol-1-yl-benzyl)-piperidin-4-ylamino]-pyrazine-2-carboxylic acid methyl ester,
2-[1-(3-ethoxy-4-methyl-benzyl)-piperidin-4-ylamino]-isonicotinonitrile,
2-[1-(3-ethoxy-4-methyl-benzyl)-piperidin-4-ylamino]-isonicotinamide, 2-[1-(4-chloro-3-ethoxy-benzyl)-piperidin-4-ylamino]-isonicotinonitrile,
2-[1-(4-chloro-3-ethoxy-benzyl)-piperidin-4-ylamino]-isonicotinamide,
2-[1-(3,5-diisopropoxy-benzyl)-piperidin-4-ylamino]-isonicotinonitrile,
2-[1-(3,5-diisopropoxy-benzyl)-piperidin-4-ylamino]-isonicotinamide,
2-[1-(3,5-diethoxy-4-fluoro-benzyl)-piperidin-4-ylamino]-isonicotinonitrile,
2-[1-(3,5-diethoxy-4-fluoro-benzyl)-piperidin-4-ylamino]-isonicotinamide,
6-[1-(4-methoxy-3-propoxy-benzyl)-piperidin-4-ylamino]-4-trifluoromethyl-nicotinamide,
6-[1-(3-isobutoxy-4-methoxy-benzyl)-piperidin-4-ylamino]-4-trifluoromethyl-nicotinamide,
6-[1-(4-chloro-3-ethoxy-benzyl)-piperidin-4-ylamino]-4-trifluoromethyl-nicotinamide,
6-[1-(3,5-diethoxy-4-fluoro-benzyl)-piperidin-4-ylamino]-4-trifluoromethyl-nicotinamide,
6-[1-(3-ethoxy-4-hydroxy-benzyl)-piperidin-4-ylamino]-4-trifluoromethyl-nicotinic acid,
6-[1-(3-ethoxy-4-methoxy-benzyl)-piperidin-4-ylamino]-4-trifluoromethyl-nicotinic acid,
6-[1-(4-methoxy-3-propoxy-benzyl)-piperidin-4-ylamino]-4-trifluoromethyl-nicotinic acid,
6-[1-(3-isobutoxy-4-methoxy-benzyl)-piperidin-4-ylamino]-4-trifluoromethyl-nicotinic acid,
5-[1-(4-chloro-3-ethoxy-benzyl)-piperidin-4-ylamino]-pyrazine-2-carboxylic acid amide,
6-[1-(4-chloro-3,5-diethoxy-benzyl)-piperidin-4-ylamino]-N-(2-hydroxy-ethyl)-nicotinamide,
6-[1-(4-chloro-3,5-diethoxy-benzyl)-piperidin-4-ylamino]-N-cyclobutyl-nicotinamide,
({6-[1-(4-chloro-3,5-diethoxy-benzyl)-piperidin-4-ylamino]-pyridine-3-carbonyl}-amino)-acetic acid,
6-[1-(4-chloro-3,5-diethoxy-benzyl)-piperidin-4-ylamino]-N-(2-methoxy-ethyl)-nicotinamide,
{6-[1-(4-chloro-3,5-diethoxy-benzyl)-piperidin-4-ylamino]-pyridin-3-yl}-morpholin-4-yl-methanone,
{6-[1-(4-chloro-3,5-diethoxy-benzyl)-piperidin-4-ylamino]-pyridin-3-yl}-((R)-3-hydroxy-pyrrolidin-1-yl)-methanone,
6-[1-(4-chloro-3,5-diethoxy-benzyl)-piperidin-4-ylamino]-N-(2-hydroxy-1-hydroxymethyl-ethyl)-nicotinamide,
6-[1-(4-chloro-3,5-diethoxy-benzyl)-piperidin-4-ylamino]-N-(2,2,2-trifluoro-ethyl)-nicotinamide,
N-(2-acetylamino-ethyl)-6-[1-(4-chloro-3,5-diethoxy-benzyl)-piperidin-4-ylamino]-nicotinamide,
1-{6-[1-(4-chloro-3,5-diethoxy-benzyl)-piperidin-4-ylamino]-pyridine-3-carbonyl}-piperidine-4-carboxylic acid amide,
1-(4-{6-[1-(4-chloro-3,5-diethoxy-benzyl)-piperidin-4-ylamino]-pyridine-3-carbonyl}-piperazin-1-yl)-ethanone,
1-{6-[1-(4-chloro-3,5-diethoxy-benzyl)-piperidin-4-ylamino]-pyridine-3-carbonyl}-piperidine-4-carboxylic acid,
(3-chloro-isoquinolin-1-yl)-[1-(2,6-diethoxy-4'-fluoro-biphenyl-4-ylmethyl)-piperidin-4-yl]-amine,
5-[1-(2,6-diethoxy-4'-fluoro-biphenyl-4-ylmethyl)-piperidin-4-ylamino]-pyrazine-2-carboxylic acid methyl ester,
[1-(3,5-diethoxy-4-fluoro-benzyl)-piperidin-4-yl]-(5-methanesulfonyl-pyridin-2-yl)-amine,
[1-(4-chloro-3,5-diethoxy-benzyl)-piperidin-4-yl]-(5-methanesulfonyl-pyridin-2-yl)-amine,
[1-(2,6-diethoxy-4'-fluoro-biphenyl-4-ylmethyl)-piperidin-4-yl]-(5-methanesulfonyl-pyridin-2-yl)-amine,
2-chloro-6-[1-(3,5-diethoxy-4-fluoro-benzyl)-piperidin-4-ylamino]-isonicotinic acid methyl ester,
2-chloro-6-[1-(4-chloro-3,5-diethoxy-benzyl)-piperidin-4-ylamino]-isonicotinic acid methyl ester,
2-chloro-6-[1-(2,6-diethoxy-4'-fluoro-biphenyl-4-ylmethyl)-piperidin-4-ylamino]-isonicotinic acid methyl ester,
{6-[1-(2,6-diethoxy-4'-fluoro-biphenyl-4-ylmethyl)-piperidin-4-ylamino]-pyridin-3-yloxy}-acetonitrile,
3-{6-[1-(4-chloro-3,5-diethoxy-benzyl)-piperidin-4-ylamino]-pyridin-3-yloxy}-propane-1,2-diol,
3-{6-[1-(2,6-diethoxy-4'-fluoro-biphenyl-4-ylmethyl)-piperidin-4-ylamino]-pyridin-3-yloxy}-propane-1,2-diol,
3-{6-[1-(2,6-diethoxy-4'-fluoro-biphenyl-4-ylmethyl)-piperidin-4-ylamino]-pyridin-3-yloxy}-propan-1-ol,
3-{6-[1-(4-chloro-3,5-diethoxy-benzyl)-piperidin-4-ylamino]-pyridin-3-yloxy}-propan-1-ol,
methanesulfonic acid 6-[1-(2,6-diethoxy-4'-fluoro-biphenyl-4-ylmethyl)-piperidin-4-ylamino]-pyridin-3-yl ester,
2-chloro-6-[1-(4-chloro-3,5-diethoxy-benzyl)-piperidin-4-ylamino]-isonicotinic acid,
2-chloro-6-[1-(2,6-diethoxy-4'-fluoro-biphenyl-4-ylmethyl)-piperidin-4-ylamino]-isonicotinic acid,
and pharmaceutically acceptable salts thereof.

Especially preferred are the following compounds of formula I of the present invention:
4-[1-(4-chloro-3-ethoxy-benzyl)-piperidin-4-ylamino]-benzonitrile,
6-[1-(4-chloro-3-ethoxy-benzyl)-piperidin-4-ylamino]-nicotinamide,
6-[1-(4-chloro-3,5-diethoxy-benzyl)-piperidin-4-ylamino]-nicotinamide,
6-[1-(4-chloro-3-ethoxy-benzyl)-piperidin-4-ylamino]-nicotinic acid,
6-[1-(4-chloro-3,5-diethoxy-benzyl)-piperidin-4-ylamino]-nicotinic acid,
[1-(3,5-diisopropoxy-benzyl)-piperidin-4-yl]-[5-(1H-tetrazol-5-yl)-pyridin-2-yl]-amine,
[1-(4-chloro-3-ethoxy-benzyl)-piperidin-4-yl]-quinolin-2-yl-amine,
[1-(4-chloro-3,5-diethoxy-benzyl)-piperidin-4-yl]-(4-methyl-quinolin-2-yl)-amine,
[1-(4-chloro-3,5-diethoxy-benzyl)-piperidin-4-yl]-isoquinolin-1-yl-amine,
({6-[1-(4-chloro-3,5-diethoxy-benzyl)-piperidin-4-ylamino]-pyridine-3-carbonyl}-amino)-acetic acid,
{6-[1-(4-chloro-3,5-diethoxy-benzyl)-piperidin-4-ylamino]-pyridin-3-yl}-morpholin-4-yl-methanone,
1-{6-[1-(4-chloro-3,5-diethoxy-benzyl)-piperidin-4-ylamino]-pyridine-3-carbonyl}-piperidine-4-carboxylic acid,
and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a compound of the general formula

G-X    II wherein G is as defined herein before and G is a leaving group,
with a compound of the formula

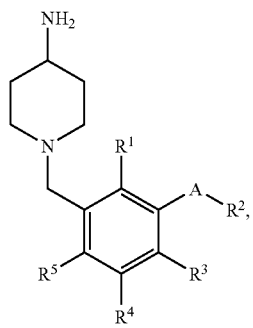
III wherein A and $R^1$ to $R^5$ are as defined herein before, to obtain a compound of the formula

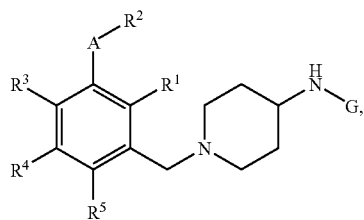
I and, if desired, converting the compound of formula I into a pharmaceutically acceptable salt; or, alternatively,
b) reacting a compound of the general formula

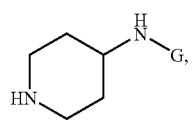
IV wherein G is as defined herein before,
with an aldehyde of the formula

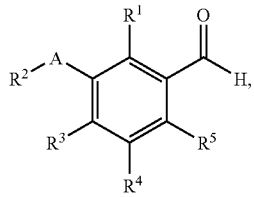
V wherein A and $R^1$ to $R^5$ are as defined herein before,
by employing a reducing agent to obtain a compound of the formula

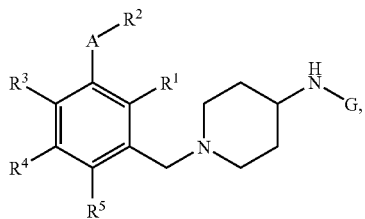
I and, if desired, converting the compound of formula I into a pharmaceutically acceptable salt.

The invention further relates to compounds of formula I as defined above, when manufactured according to a process as defined above.

Suitable reducing agents are preferably selected from the group consisting of pyridine-$BH_3$ complex, $NaBH(OAc)_3$ and $NaCNBH_3$. The reaction can be carried out under acidic conditions by using an acid such as acetic acid or formic acid or an Lewis acid (e.g., $Ti(iPrO)_4$, $ZnCl_2$) or under basic conditions (no additive) in a suitable solvent such as dichloromethane, dichloroethane or ethanol (or mixtures thereof) at ambient or elevated temperatures using conventional heating or heating by microwave irradiation.

As described above, the compounds of formula I of the present invention can be used as medicaments for the treatment and/or prevention of diseases which are associated with the modulation of SST receptors subtype 5.

"Diseases which are associated with the modulation of SST receptors subtype 5" are such diseases as diabetes mellitus, particularly type II diabetes mellitus, impaired fasting glucose, impaired glucose tolerance, micro- and macrovascular diabetic complications, posttransplantation diabetes mellitus in patients having type I diabetes mellitus, gestational diabetes, obesity, inflammatory bowel diseases such as Crohn's disease or ulcerative colitis, malabsorption, autoimmune diseases such as rheumatoid arthritis, osteoarthritis, psoriasis and other skin disorder, and immunodeficiencies. Microvascular diabetic complications include diabetic nephropathy and diabetic retinopathy, whereas macrovascular diabetes-associated complications lead to an increased risk for myocardial infarction, stroke and limb amputations.

The use as medicament for the treatment and/or prevention of diabetes mellitus, particularly type II diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are which are associated with the modulation of SST receptors subtype 5, which method comprises administering a compound of formula I to a human or animal. The method for the treatment and/or prevention of diabetes mellitus, particularly type II diabetes mellitus, impaired fasting glucose or impaired glucose tolerance, is most preferred.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5. Preferred examples of such diseases are diabetes mellitus, particularly type II diabetes mellitus, impaired fasting glucose or impaired glucose tolerance.

The compounds of formula I can be manufactured by the methods given below, by the methods given in the examples or by analogous methods. Appropriate reaction conditions for the individual reaction steps are standard reactions and are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia and Ib, are described in Schemes 1 to 6.

The synthesis of compounds of the general formula I, particularly compounds according to formula Ia can be accomplished according to Scheme 1.

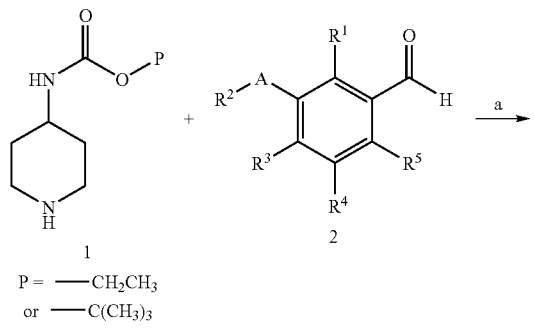

Scheme 1

P = —CH$_2$CH$_3$
or —C(CH$_3$)$_3$

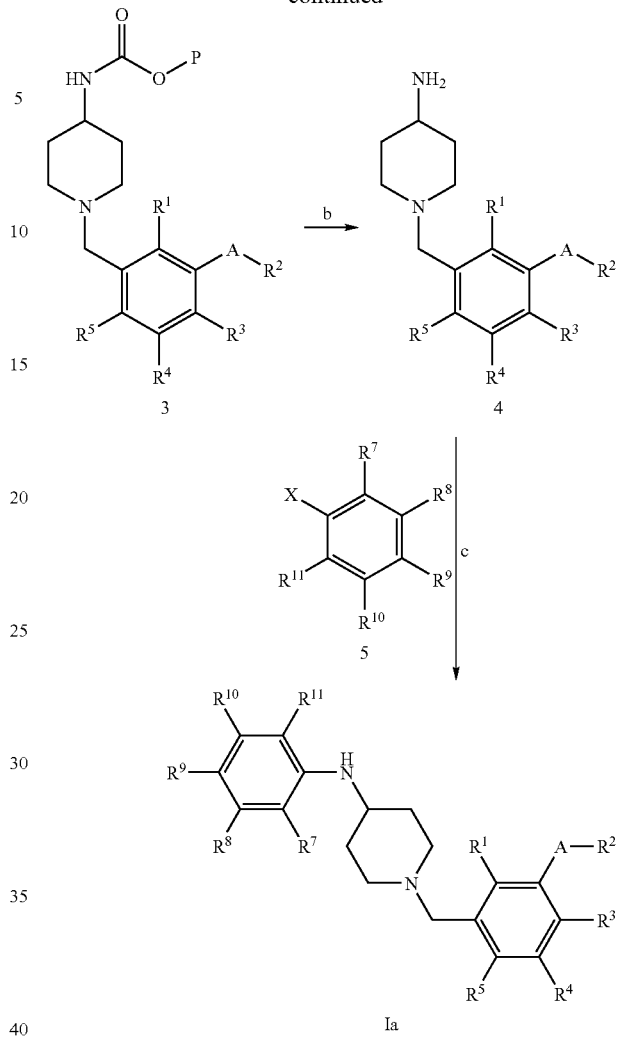

Reductive N-alkylation of suitably protected piperidines (for protecting groups see *Protective Groups in Organic Synthesis*, T. W. Greene and P. G. M. Wuts, 3$^{rd}$ Edition, 1999, Wiley-Interscience) of formula 1 with aldehydes 2 in the presence of a reducing agent such as pyridine-BH$_3$ complex, NaBH(OAc)$_3$ or NaCNBH$_3$ under acidic conditions (e.g., acetic acid, formic acid), by using a Lewis acid (e.g., Ti(iPrO)$_4$, ZnCl$_2$) or under buffered conditions, e.g., in the presence of acetic acid and a tertiary amine like N-ethyldiisopropylamine or triethylamine, in a suitable solvent such as dichloromethane (DCM), dichloroethane, ethanol or isopropanol (or mixtures thereof) at ambient or elevated temperatures using conventional heating or heating by microwave irradiation provide piperidines of general formula 3 (Scheme 1, step a). The piperidines of formula 1 may thereby used either as a salt, e.g., hydrochloride or hydrobromide salt, or as the corresponding free amine. The alkyloxycarbonyl protecting group present in compounds 3 can be removed, using e.g., 48% aqueous hydrogen bromide or 37% aqueous hydrochloric acid as reagent preferably at elevated temperatures to remove an ethyl carbamate or using trifluoroacetic acid or hydrochloric acid in a solvent like dichloromethane, dioxane or THF preferable at room temperature to remove a tert-butyloxycarbonyl (BOC)-protective group (see *Protective Groups in Organic Synthesis*, T. W. Greene and P. G. M.

Wuts, 3<sup>rd</sup> Edition, 1999, Wiley-Interscience), yielding 4-amino piperidines of formula 4 (Scheme 1, step b).

Target compounds of formula Ia can be synthesized by nucleophilic replacement reaction of 4-amino piperidines of formula 4 and fluorobenzenes of general structure 5 at elevated temperatures (Scheme 1, step c), whereby $R^1$, $R^3$ and/or $R^5$ is an electron withdrawing group such as nitrile. Thereby heating can be achieved conventionally or by microwave irradiation using a suitable microwave irradiation apparatus. Furthermore the reaction can be conducted in the presence of or without solvent (typically an aprotic polar solvent such as DMF (N,N-dimethylformamide), DMAc (dimethylacetamide), NMP (N-methylpyrrolidon), ethylene glycol, acetonitrile or THF (tetrahydrofurane)) and in the presence of or without a tertiary amine base such as N-ethyl diisopropylamine, triethylamine or pyridine. The time for the reaction may vary widely, depending on the many factors, notably the reaction temperature and the nature of the reagents. However, a period of 0.5 h to several days will usually suffice to yield the piperidine derivatives of formula Ia. The starting materials and some of the intermediates of general structure 5 (e.g., 4-fluoro-benzonitrile) are known compounds and are commercially available or can be prepared by numerous methods using conventional reaction procedures generally known in the art. The 4-amino piperidines of formula 4 may thereby used either as a salt, e.g., hydrochloride or hydrobromide salt, or as the corresponding free amine.

Target structures of general formula Ia can also be synthesized by reductive N-alkylation of anilines 6 with suitably protected piperidines of formula 7 (for protecting groups see *Protective Groups in Organic Synthesis*, T. W. Greene and P. G. M. Wuts, 3<sup>rd</sup> Edition, 1999, Wiley-Interscience) in the presence of a reducing agent such as pyridine-BH$_3$ complex, NaBH(OAc)$_3$ or NaCNBH$_3$ under acidic conditions (e.g., acetic acid, formic acid), by using a Lewis acid (e.g., Ti(iPrO)$_4$, ZnCl$_2$) or under buffered conditions, e.g., in the presence of acetic acid and a tertiary amine like N-ethyl diisopropylamine or triethylamine in a suitable solvent such as dichloromethane, dichloroethane, ethanol or isopropanol (or mixtures thereof) at ambient or elevated temperatures using conventional heating or heating by microwave irradiation providing piperidines of general formula 8 (Scheme 2, step a). The alkyloxycarbonyl protecting group present in compounds 8 can be removed, using e.g., 48% aqueous hydrogen bromide or 37% aqueous hydrochloric acid as reagent preferably at elevated temperatures to remove an ethyl carbamate or using trifluoroacetic acid or hydrochloric acid in a solvent like dichloromethane, dioxane or THF preferable at room temperature to remove a tert-butyloxycarbonyl (BOC)-protective group (see *Protective Groups in Organic Synthesis*, T. W. Greene and P. G. M. Wuts, 3<sup>rd</sup> Edition, 1999, Wiley-Interscience), yielding phenyl-piperidin-4-yl-amines of formula 9 (Scheme 2, step b). Reductive N-alkylation of piperidines 9 with aldehydes 2 provides then access to target structures Ia (Scheme 2, step c).

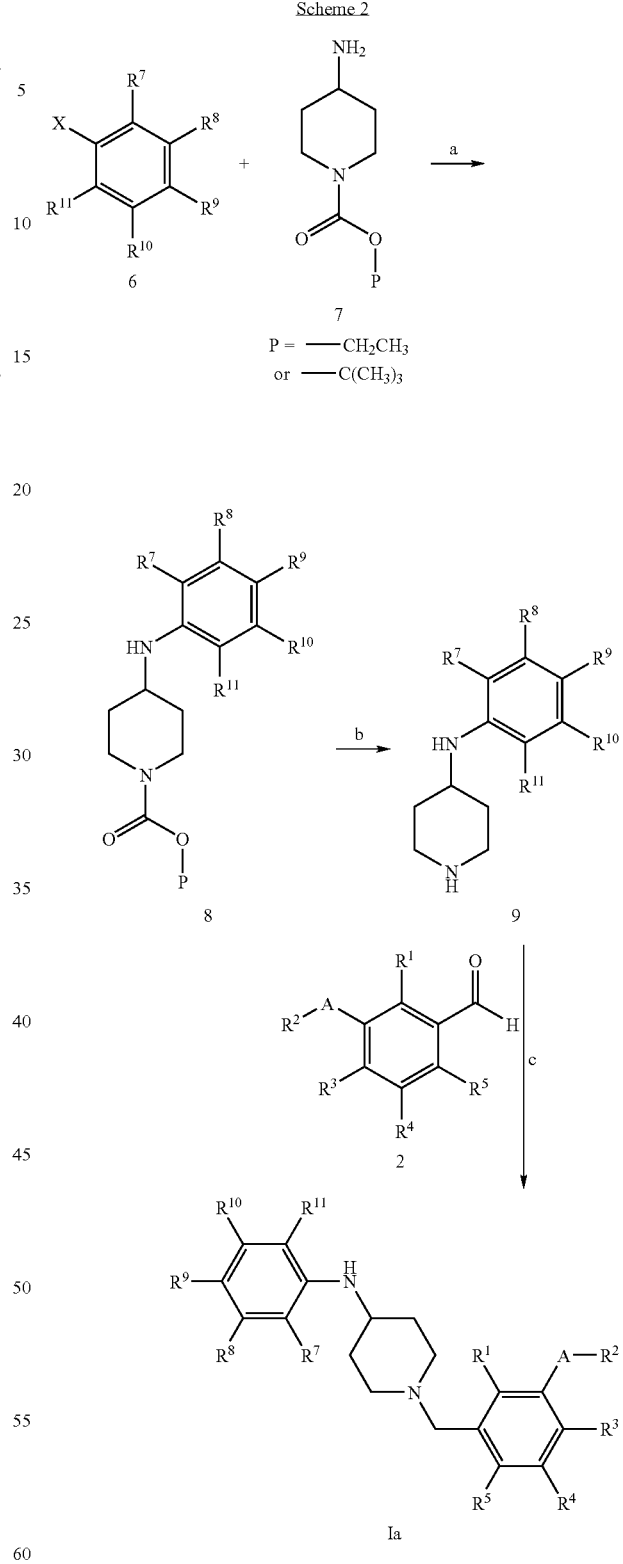

Alternatively, target structures of formula Ia can be accomplished employing an inverted reaction sequence. Reductive coupling of suitably ketone protected piperidines (for protecting groups see *Protective Groups in Organic Synthesis*, T. W. Greene and P. G. M. Wuts, 3<sup>rd</sup> Edition, 1999, Wiley-Interscience) such as 1,4-dioxa-8-aza-spiro[4.5]decane (10) with aldehydes 2 provides piperidines 11 (Scheme 3, step a), which are subsequently deprotected to the tertiary amine 12 (Scheme 3, step b). In the case of an acetal this deprotection step is preferentially conducted under acid catalysis (e.g., hydrochloric acid) in a solvent such as water under elevated temperatures. Finally, N-alkylation of benzyl-piperidinone 12 with aniline 6 under reductive reaction conditions affords target structures Ia (Scheme 3, step c). In contrast to the strategy outlined in Scheme 2, where the point of diversification is the aryl moiety, this synthetic route is of particular interest if the variation of the benzyl moiety is aimed for in a rapid and parallel fashion.

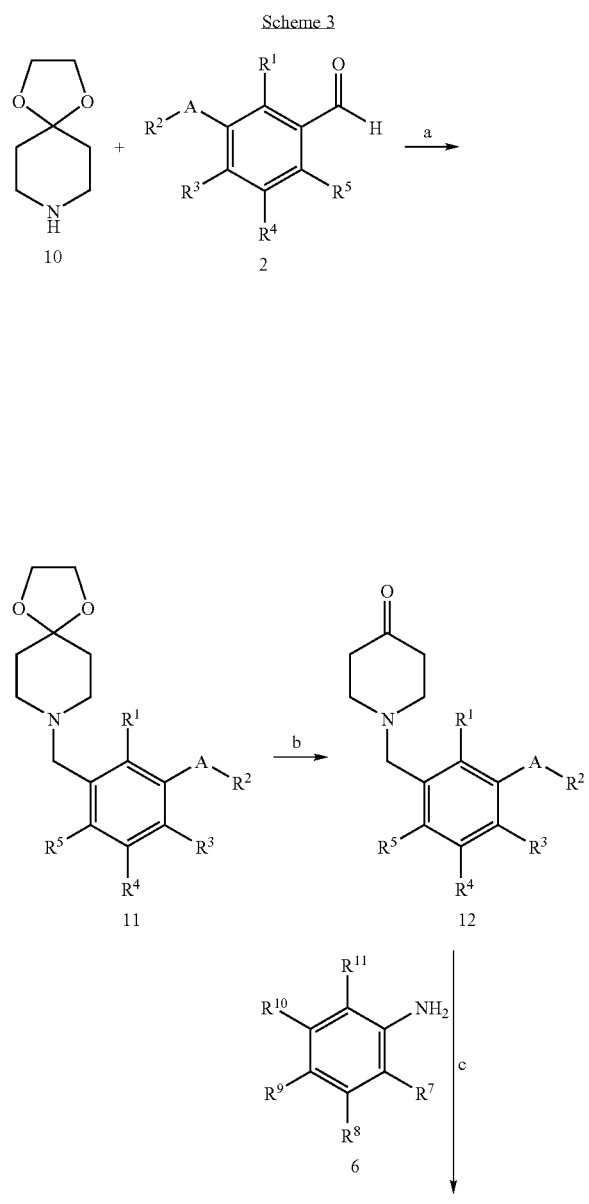

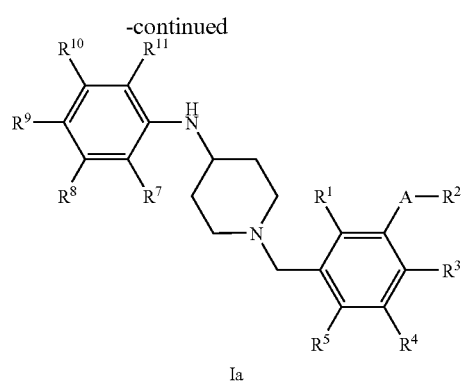

The synthesis of target compounds of general formula I, particularly compounds according to formula Ib is outlined in Scheme 4. Reductive N-alkylation of suitably protected piperidines of formula 1 with aldehydes 2 in the presence of a reducing agent affords piperidines of general formula 3 (Scheme 4, step a). Removal of the preferentially carbamate protection group yields then the free 4-amino piperidines of formula 4 (Scheme 4, step b). Target structures of formula Ib are accessible by nucleophilic replacement reaction of 4-amino-piperidines of formula 4 and a variety of differentially substituted pyridines, quinolines, isoquinolines, naphthyridines and pyrazines of general structure 5 at room or elevated temperatures (Scheme 4, step c), whereby X is a suitable leaving group such as fluorine, chlorine, bromine or methyl sulfone. In order to enhance the rate of conversion heating might be applied, whereby conventional heating or microwave assisted heating might be employed using a suitable microwave irradiation apparatus. The 4-amino-piperidines of formula 4 may thereby used either as a salt, e.g., hydrochloride or hydrobromide salt, or as the corresponding free amine. Alternatively the nucleophilic displacement reaction can be conducted under basic conditions by using $K_2CO_3$, KOH, $NaOCH_3$, KOtert-Bu or in particular by using NaH. Furthermore the reaction can be conducted in the presence of or without solvent (typically an aprotic polar solvent such as DMF (N,N-dimethylformamide), DMAc (dimethylacetamide), NMP (N-methylpyrrolidon), ethylene glycol, acetonitrile or THF) and in the presence of or without a tertiary amine base such as triethylamine, N-ethyl diisopropylamine or pyridine and in the presence with or without copper(I) bromide or copper(I) iodide. The time for the reaction may vary widely, depending on the many factors, notably the reaction temperature and the nature of the reagents. However, a period of 0.5 h to several days will usually suffice to yield the piperidine derivatives of formula Ib.

The starting materials and some of the intermediates of general structure 5 (e.g., 2-chloro-pyridines, 2-chloro-quinolines or 2-chloro-pyrazines) are known compounds and are commercially available or can be prepared by numerous methods using conventional reaction procedures generally known in the art. There is a plethora of references known in the art teaching methods useful for the preparation of aforementioned heterocyclic ring systems. The reader is referred to (a) A. R. Katritzky, *Handbook of Heterocyclic Chemistry*, 1985, Pergamon Press Ltd, Oxford, United Kingdom (pyridine synthesis pp. 407-411; quinoline synthesis pp. 457-461;

isoquinoline synthesis pp. 463-465; pyrazine synthesis pp. 432-433) and references cited therein, (b) T. Eicher and S. Hauptmann (translated by H. Suschitzky and J. Suschitzky), *The Chemistry of Heterocycles*, 1995, Georg Thieme Verlag, Stuttgart, Deutschland (pyridine synthesis pp. 295-305; quinoline synthesis pp. 325-334; isoquinoline synthesis pp. 341-347; pyrazine synthesis pp. 419-422) and references cited therein and (c) H. Krauch and W. Kunz, *Reaktionen der organischen Chemie*, 6., neubearbeitete Auflage, 1997, Huthig GmbH, Heidelberg, Deutschland (pyridine synthesis pp. 589-590; quinoline synthesis pp. 219-221; isoquinoline synthesis pp. 423-429; pyrazine synthesis pp. 578-580) and references cited therein.

Alternatively target structures Ib can be manufactured using Pd(O)-catalyzed amination reactions of 4-amino-piperidines 4 with 2-halo pyridines, 2-halo-quinolines or 1-halo-isoquinolines of general formula 13 (e.g., Buchwald-Hartwig coupling; see (a) J. P. Wolfe, S. Wagaw and S. L. Buchwald *J. Am. Chem. Soc.* 1996, 118, 7215-7216; (b) J. P. Wolfe and S. L. Buchwald *Tetrahedron Lett.* 1997, 38, 6359-6362; (c) J. P. Wolfe, S. Wagaw, J.-F. Marcoux and S. L. Buchwald *Acc. Chem. Res.* 1998, 31, 805-818; (d) B. H. Yang and S. L. Buchwald *J. Organomet. Chem.* 1999, 576, 125-146; (e) J. F. Hartwig *Angew. Chem. Int. Ed.* 1998, 37, 2046-2067). Thereby halo-substituted heterocylces 13 are reacted with primary amines 4 under an inert atmosphere such as argon or nitrogen in the presence of a palladium catalys such as tris (dibenzylideneacetone)dipalladium(0) $(Pd_2(dba)_3)$ or palladium(II) acetate $(Pd(COOCH_3)_2)$, a phosphine ligand like triphenylphosphine, rac-2,2'-bis(diphenylphosphino)-1,1'-binaphthalene (rac-BINAP) or (R)-(−)-1-[(S)-2-(dicyclohexylphosphino)ferrocenyl]ethyldi-tert-butylphosphine (Josiphos; see Q. Shen, S. Shekhar, J. P. Stambuli and J. F. Hartwig *Angew. Chem. Int. Ed.* 2005, 44, 1371-1375) and a base such as $Cs_2CO_3$ or KOtert-Bu in a solvent like toluene, ethanol or water or mixtures thereof (Scheme 4, step c). Said C—N formation reaction may be conducted at room temperature or elevated temperatures, whereby heating might be achieved conventionally or by microwave irradiation (see also Palladium(0) Complexes in Organic Chemistry, in *Organometallics in Synthesis* (Ed. M. Schlosser), Chapter 4, 2nd Edition, 2002, John Wiley & Sons, Ltd, Chichester, UK).

If the nucleophilic substitution or Pd(O)-catalyzed amination reaction has been conducted with starting materials which potentially can result in regioisomeric coupling products such as asymmetrically substituted 2,6-dichloro-pyridines or 1,3-dichloro-isoquinolines, the regiochemistry of target structures Ib was unambiguously established by means of nuclear magnetic resonance spectroscopy employing 1D-NOE difference, 2D-NOESY and/or $^{13}C/^1H$ HMBC experiments. In all cases reaction products were successfully separated by conventional chromatographic methods.

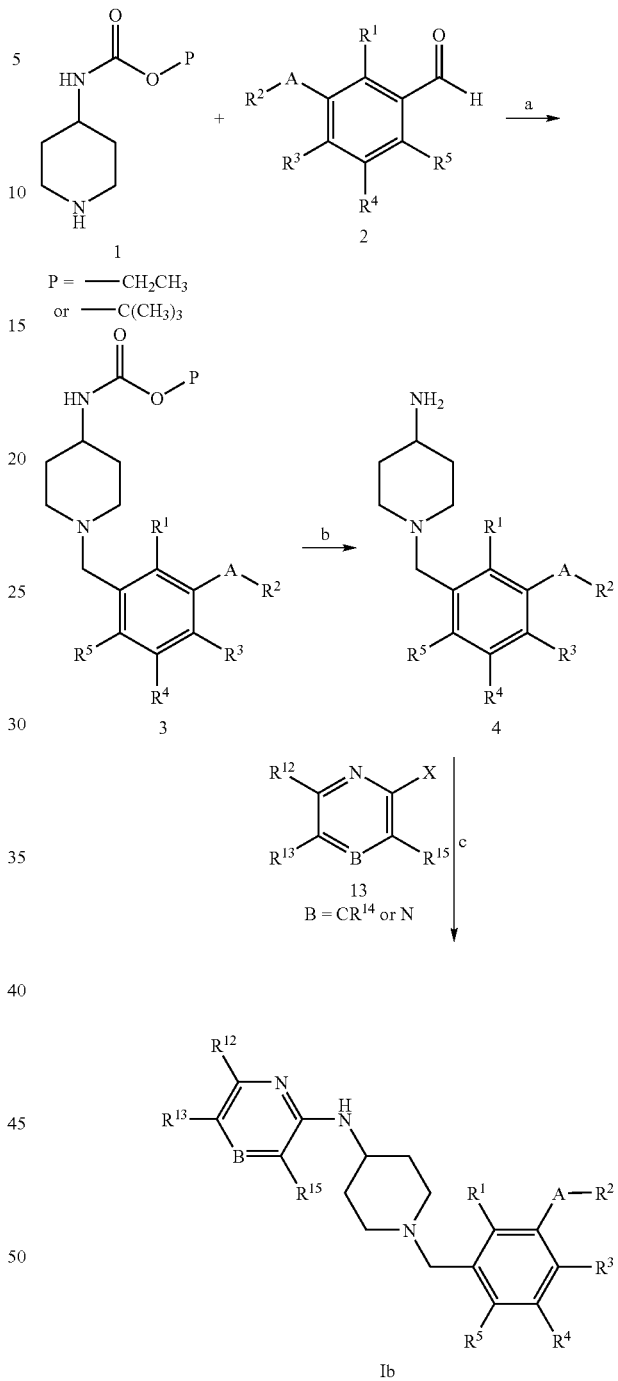

Target structures of formula Ib can also be accomplished employing an inverted reaction sequence, namely by first coupling halo-substituted heterocycles 13 with alkyloxycarbonyl protected amine 7 (Scheme 5, step a). The protection group of piperidines 14 are then removed yielding the secondary amines 15 (Scheme 5, step b), which undergo reductive N-alkylation to target structures Ib (Scheme 5, step c). In contrast to the strategy outlined in Scheme 4 where the point of diversification is the heteroaryl moiety this synthetic route is of particular interest for the rapid and parallel variation of the benzyl moiety.

Scheme 5

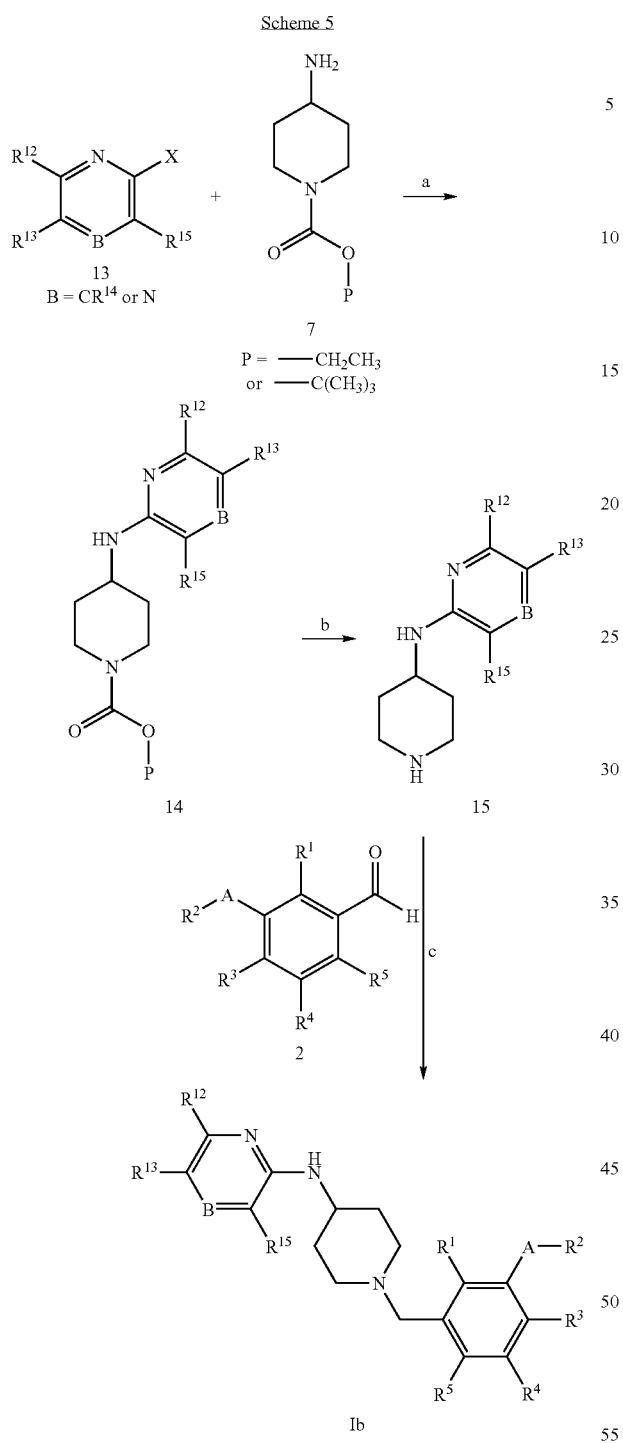

analogous alkylation reactions. Alternatively target structures of formula Ia and Ib might be accessible by Mitsunobu reaction (D. L. Hughes, The Mitsunobu Reaction, in *Organic Reactions*, Volume 42, 1992, John Wiley & Sons, New York; pp. 335-656) applying alcohols 17 activated by a mixture of a phosphine like a trialkylphosphine such as tributylphosphine ((n-Bu)$_3$P), triphenylphosphine (Ph$_3$P) and the like and a diazo-compound like diethyl-azodicarboxylate (DEAD), diisopropyl-azodicarboxylate (DIAD) or di-tert-butyl-azodicarboxylate and the like in a solvent commonly used for such transfomations like tetrahydrofurane (THF), toluene, dichloromethane and the like (Scheme 6, step b). There is no particular restriction on the nature of the solvent to be employed, provided that it has no adverse effect on the reaction or the reagents involved and that it can dissolve the reagents, at least to some extent. The reaction can take place over a wide range of temperatures ranging from ambient temperatures to the reflux temperature of the solvent employed. In case of compounds of formula Ia, $R^a$ has the meanings of $R^7$ and $R^b$, $R^c$, $R^d$ and $R^e$ correspond to $R^8$, $R^9$, $R^{10}$ and $R^{11}$, respectively. In case of compounds of formula Ib, $R^a$ corresponds to $R^{15}$ ($B^1$=$CR^b$) or $R^{18}$ ($B^1$=N), $R^b$ can have the meanings of $R^{14}$, $R^c$ corresponds to $R^{13}$ or $R^{17}$ and $R^d$ corresponds to $R^{12}$ or $R^{16}$.

Scheme 6

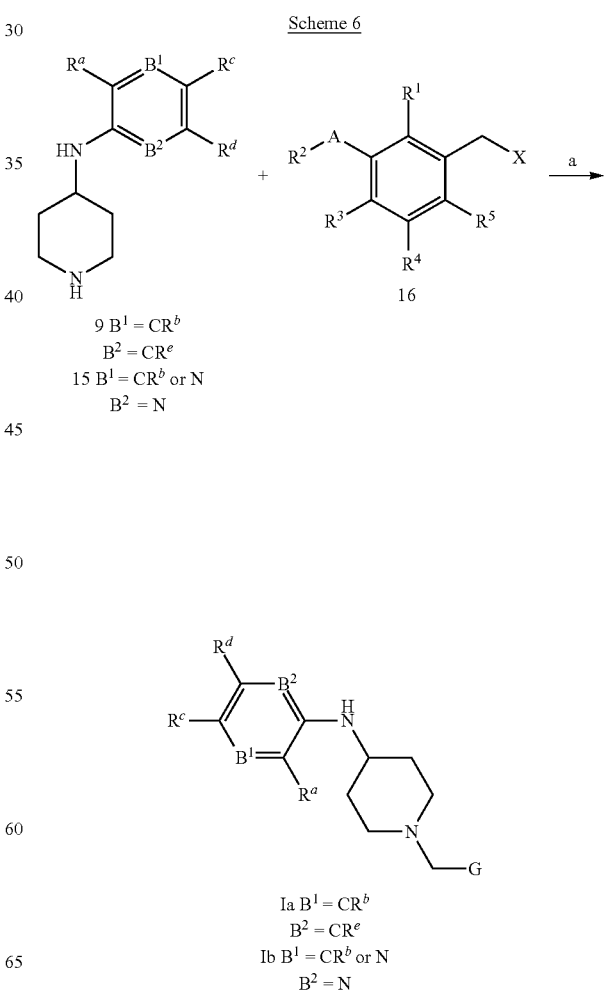

Target compounds of formula Ia and Ib might also be manufactured by direct alkylation of piperidines 9 and 15 with suitable halides, mesylates, tosylates or alcohols containing any other suitable leaving group of general structure 16 in a solvent such as N,N-dimethylformamide, dichloromethane, dichloroethane or acetone at ambient or elevated temperatures using conventional heating or heating by microwave irradiation with the addition of a suitable tertiary amine base (e.g., triethylamine, N-ethyl diisopropylamine) or an inorganic base (e.g., Cs$_2$CO$_3$, K$_2$CO$_3$; Scheme 6, step a) or by

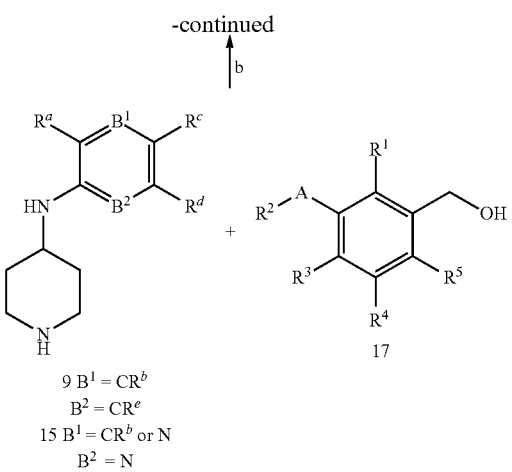

9 $B^1 = CR^b$
  $B^2 = CR^e$
15 $B^1 = CR^b$ or N
  $B^2 = N$

Compounds of formula Ib containing a cyano group can be further converted to carboxamides under acidic or basic reaction conditions (for further reaction conditions see R. C. Larock, *Comprehensive Organic Transformations—A Guide to Functional Group Preparations*, 1989, VCH Publishers Inc., New York; pp. 994). If the reaction is conducted under acidic conditions, preferentially hydrochloric acid or sulfuric acid are used at room temperature or elevated temperatures in a solvent such as dioxane or THF (tetrahydrofurane).

Compounds of formula Ib containing an alkyl ester group, preferentially a methyl ester group, can be further transformed to carboxamides under basic reaction conditions (for further reaction conditions see R. C. Larock, *Comprehensive Organic Transformations—A Guide to Functional Group Preparations*, 1989, VCH Publishers Inc., New York; pp. 987-988), preferentially using ammonium hydroxide in the presence of potassium cyanide at room temperature or elevated temperatures in a solvent such as DMF (N,N-dimethylformamide) or DMAc (dimethylacetamide). In order to enhance the rate of conversion heating might be applied, whereby conventional heating or microwave assisted heating might be employed using a suitable microwave irradiation apparatus.

Compounds of formula Ib containing an alkyl ester group, preferentially a methyl ester group, can be further converted to carboxylic acids under basic reaction conditions (for further reaction conditions see R. C. Larock, *Comprehensive Organic Transformations—A Guide to Functional Group Preparations*, 1989, VCH Publishers Inc., New York; pp. 981-985), preferentially using potassium or sodium hydroxide at room temperature or elevated temperatures in a solvent such as methanol, dioxane, THF (tetrahydrofurane), DMF (N,N-dimethylformamide) or DMAc (dimethylacetamide) or mixtures thereof. In order to enhance the rate of conversion heating might be applied, whereby conventional heating or microwave assisted heating might be employed using a suitable microwave irradiation apparatus.

Compounds of formula Ib containing a carboxylic acid function can be further transformed to amides by reaction with primary or secondary amines (for further reaction conditions see R. C. Larock, *Comprehensive Organic Transformations—A Guide to Functional Group Preparations*, 1989, VCH Publishers Inc., New York; pp. 972-976). The coupling of carboxylic acids with amines is widely described in literature and the procedures are known to those in the art (see also R. C. Larock, *Organic Transformations: A Guide to Functional Group Preparations*, 2$^{nd}$ Edition, 1999, John Wiley & Sons, New York). Preferentially, nicotinic acids of general structure Ib can conveniently be transformed to the respective amide through coupling with a primary or secondary amine employing a coupling agent. Suitable coupling agents for the reaction of carboxylic acids with amines are for example N,N'-carbonyldiimidazole (CDI), N,N'-dicyclohexylcarbodiimide (DCC), 1-(3-dimethyl-aminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like. Preferred coupling agents are 1-[bis(dimethylamino) methylene]-1H-1,2,3-triazolo[4,5-b]pyridinium-3-oxide hexafluorophosphate (HATU) or O-benzotriazol-1-yl-N,N,N',N'-tetramethyl-uronium tetrafluoroborate (TBTU). Solvents commonly used for such kind of reactions are DMF (N,N-dimethylformamide), DMAc (dimethylacetamide), DCM (dichloromethane), dioxane, THF (tetrahydrofurane) and the like in the presence of or without a tertiary amine base such as N-ethyl diisopropylamine, triethylamine or pyridine. The reaction can take place over a wide range of temperatures from ambient temperature to the reflux temperature of the solvent applied. The time for the reaction may also vary widely, depending on the many factors, notably the reaction temperature and the nature of the reagents. However, a period of 0.5 h to several days will usually suffice to yield the amide derivatives of formula Ib.

Synthesis of Aldehyde Intermediates

The requisite aldehyde partners are either commercially available or can be derived by alkylation with alkyl halides, alkyl mesylates, alkyl tosylates or alcohols containing any other suitable leaving group in a polar solvent such as DMF (N,N-dimethylformamide) or acetone and a suitable base (e.g., $Cs_2CO_3$, $K_2CO_3$) at room temperature or elevated temperatures, by Mitsunobu reaction with alcohols activated by a mixture of triphenylphosphine and diethylazadicarboxylate, or by analogous alkylation of the phenolic carboxylic esters or acids of formula 18 (Scheme 7, step a). Reduction of the esters of formula 19 by a suitable reducing agent (e.g., diisobutylaluminium hydride at low temperature, with $LiAlH_4$ at elevated or ambient temperature) in a solvent such as THF (tetrahydrofurane) provides the corresponding benzylalcohols of formula 20 (Scheme 7, step b). These can then be oxidized to the aldehydes of formula 21, preferably with activated $MnO_2$ as oxidant in dichloromethane (Scheme 7, step c).

Alternatively the introduction of the side-chain can be accomplished by direct alkylation (sequential for unsymmetrical compounds) of the phenolic benzaldehydes of formula 22 providing the desired compounds of formula 21 directly (Scheme 7, step d).

A further well-established route towards the synthesis of benzylaldehydes of formula 24 consists in the reduction of the corresponding benzonitriles of formula 23 by a suitable reducing agent such as diisobutylaluminium hydride at low temperature in a non-protic polar solvent (e.g., THF; Scheme 7, step e).

Additional syntheses of aldehydes of formula II are described in the examples.

Scheme 7

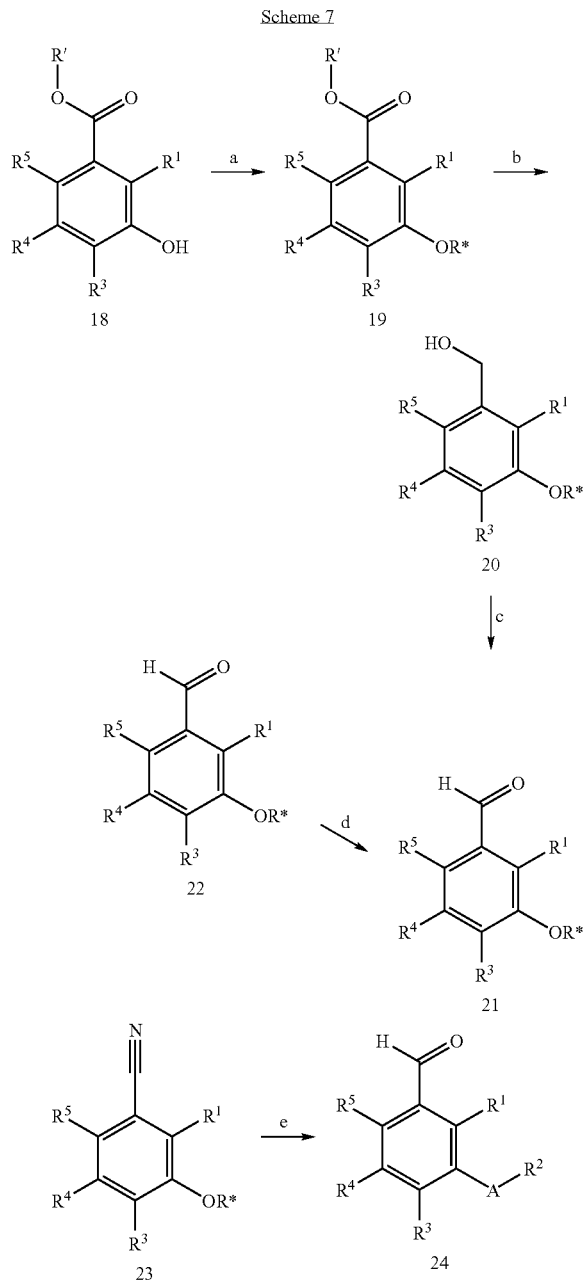

As described hereinbefore, it has been found that the compounds of formula I possess pharmaceutical activity, in particular they are modulators of somatostatin receptor activity. More particularly, the compounds of the present invention have been found to be antagonists of the somatostatin receptor subtype 5 (SSTR5).

The following tests were carried out in order to determine the activity of the compounds of formula I.

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing, membranes were diluted in assay buffer (50 mM Tris-HCl at pH 7.4, 5 mM $MgCl_2$ and 0.20% BSA) and subjected to dounce homogenization.

For binding studies, 0.1 mL membrane suspension, corresponding to app. $6 \times 10^{-15}$ mol receptor, was incubated for 1 h at room temperature with 0.05 nM $^{125}$I-labeled tracer (11-Tyr somatostatin-14, Perkin-Elmer) and either test compounds in varying concentrations or, for the determination of non-specific binding, 0.001 mM non-labeled somatostatin-14. The incubation was stopped by filtration through GF/B glassfiber filters and washing with ice-cold wash buffer (50 mM Tris-HCl at pH 7.4). The bound radioactivity was measured after application of a scintillation cocktail (Microscint 40) and expressed as disintegrations per minute (dpm).

The receptor concentration was determined in a prior saturation experiment where a fixed, arbitrary amount of membranes was incubated with a concentration range of radiolabeled tracer. This allows estimating the total number of specific binding sites per amount of protein (i.e., $B_{max}$), typically between 1 and 5 pmol/mg.

The concentration of the test compound required to result in half maximal inhibition of binding of the radio-labeled tracer ($IC_{50}$) was estimated from a concentration-versus-dpm graph. The binding affinity ($K_i$) was calculated from the $IC_{50}$ by applying the Cheng-Prussoff equation for single binding sites.

For functional experiments, 50'000 cells were incubated in Krebs Ringer HEPES buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM HEPES, adjusted to pH 7.4) supplemented with 1 mM IBMX and 0.1% BSA, then stimulated with 0.004 mM forskolin. Simultaneously with forskolin, test compounds in varying concentrations were applied. Cells were then incubated for 20 minutes at 37° C. and 5% $CO_2$. Subsequently, cells were lysed and cAMP concentration measured using a fluorescence-based commercial kit according to the manufacturer (HitHunter cAMP, DiscoverX).

The concentration of the test compound to induce a half maximal effect (i.e., $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e., $IC_{50}$) were deduced from concentration-versus-fluorescence graphs.

The compounds of the present invention exhibit $K_i$ values of 0.1 nM to 10 μM, preferably $K_i$ values of 1 nM to 500 nM and more preferably 0.1 nM to 100 nM for human subtype 5 somatostatin receptor. The following table shows measured values for selected compounds of the present invention.

|  | SSTR5 $K_i$ (nmol/l) |
| --- | --- |
| Example 24 | 789 |
| Example 103 | 7 |
| Example 205 | 86 |

The compounds of formula I and their pharmaceutically acceptable salts and esters can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or infusion solutions, or topically, e.g., in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The present invention will be further explained by reference to the following illustrative examples. They are, however, not intended to limit its scope in any manner.

EXAMPLES

Abbreviations

Ar=argon, DMAc=dimethylacetamide, DMF=N,N-dimethylformamide, DMSO=dimethyl sulfoxide, EI=electron impact (ionization), ESI=electron spray ionisation, HATU=1-[bis(dimethylamino)methylene]-1H-1,2,3-triazolo[4,5-b]pyridinium-3-oxide hexafluorophosphate, HPLC=high performance liquid chromatography, Hyflo Super Gel®=filtration aid (Fluka), ISN=ion spray negative (mode), ISP=ion spray positive (mode), Josiphos ligand=(R)-(–)-1-[(S)-2-(dicyclohexyl-phosphino)-ferrocenyl]ethyl-di-tert-butylphosphine, NMP=N-methylpyrrolidon, NMR=nuclear magnetic resonance, MPLC=medium pressure liquid chromatography, MS=mass spectrum, P=protecting group, R=any group, rt=room temperature, THF=tetrahydrofuran, X=halogen, Y=any group including heteroatoms and halides.

Example 1

4-[1-(3-Ethoxy-4-methoxy-benzyl)-piperidin-4-ylamino]-benzonitrile

Step 1: [1-(3-Ethoxy-4-methoxy-benzyl)-piperidin-4-yl]-carbamic acid tert-butyl ester A mixture of piperidin-4-yl-carbamic acid tert-butyl ester (10.0 g, 50.0 mmol, 1.0 equiv; commercially available), 3-ethoxy-4-methoxy-benzaldehyde (10.8 g, 60.0 mmol, 1.2 equiv; commercially available) and acetic acid (11.4 mL, 12.01 g, 200.0 mmol, 4.0 equiv) in ethanol (40 mL) was heated by microwave irradiation to 100° C. for 5 min. Sodium cyanoborohydride (6.27 g, 100.0 mmol, 2.0 equiv), dissolved in ethanol (20 mL), was added and the reaction mixture heated by microwave irradiation to 100° C. for an additional time period of 5 min. The solvent was removed under reduced pressure and the crude reaction product extracted from a solution of 1 M NaOH (200 mL) with ethyl acetate (3×100 mL). The combined organic phases were dried over MgSO$_4$, concentrated by evaporation under reduced pressure and the crude material purified with column chromatography on silica eluting with ethyl acetate to yield 9.71 g (53%) of the title compound as a white solid. MS (ISP): 365.3 [M+H]$^+$.

Step 2: 1-(3-Ethoxy-4-methoxy-benzyl)-piperidin-4-ylamine (Intermediate A1)

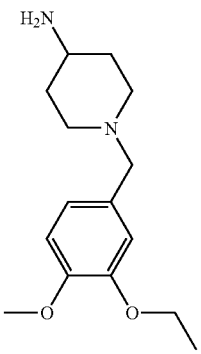

A solution of [1-(3-ethoxy-4-methoxy-benzyl)-piperidin-4-yl]-carbamic acid tert-butyl ester (9.71 g, 26.64 mmol) in ethanol (50 mL) and 4 M HCl in dioxane (75 mL) was stirred at rt for 2 h. The hydrochloric acid was removed under reduced pressure and the crude reaction product extracted from a solution of 1 M NaOH (200 mL) with ethyl acetate (3×100 mL). The combined organic phases were dried over MgSO$_4$ and concentrated by evaporation under reduced pressure yielding 4.69 g (89%) of a white solid. The crude material was directly used in the following reaction step. MS (ESI): 265.0 [M+H]$^+$.

Step 3: 4-[1-(3-Ethoxy-4-methoxy-benzyl)-piperidin-4-ylamino]-benzonitrile

A solution of 4-fluoro-benzonitrile (36.3 mg, 0.30 mmol, 1.0 equiv; commercially available) and 1-(3-ethoxy-4-methoxy-benzyl)-piperidin-4-ylamine (95.2 mg, 0.36 mmol, 1.2 equiv; intermediate A1) in DMAc (2 mL) was heated by microwave irradiation to 210° C. for 3 h. Removal of the solvent under reduced pressure and purification by preparative HPLC on reversed phase eluting with a gradient of acetonitrile/water provided 17.8 mg (16%) of the title compound. MS (ISP): 366.4 [M+H]$^+$.

Example 2

4-[1-(4-Chloro-3-ethoxy-benzyl)-piperidin-4-ylamino]-benzonitrile

Step 1: [1-(4-Chloro-3-ethoxy-benzyl)-piperidin-4-yl]-carbamic acid tert-butyl ester A mixture of piperidin-4-yl-carbamic acid tert-butyl ester (5.0 g, 25.0 mmol, 1.0 equiv; commercially available), 4-chloro-3-ethoxy-benzaldehyde (5.54 g, 30.0 mmol, 1.2 equiv; intermediate E2, vide infra) and acetic acid (5.7 mL, 6.01 g, 100.0 mmol, 4.0 equiv) in ethanol (25 mL) was heated by microwave irradiation to 100° C. for 5 min. Sodium cyanoborohydride (3.14 g, 50.0 mmol, 2.0 equiv), dissolved in ethanol (10 mL), was added and the reaction mixture heated by microwave irradiation to 100° C. for an additional time period of 10 min. The solvent was removed under reduced pressure and the crude reaction product extracted from a solution of 1 M NaOH (100 mL) with ethyl acetate (3×100 mL). The combined organic phases were dried over MgSO$_4$, concentrated by evaporation under reduced pressure and the crude material purified by silica column chromatography using a MPLC system (CombiFlash Companion, Isco Inc.) eluting with a gradient of heptane/ethyl acetate providing 3.91 g (42%) of the title compound. MS (ISP): 369.0 [M+H]$^+$.

Step 2: 1-(4-Chloro-3-ethoxy-benzyl)-piperidin-4-ylamine (Intermediate A2)

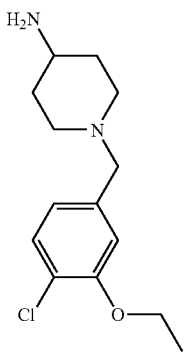

A solution of [1-(4-chloro-3-ethoxy-benzyl)-piperidin-4-yl]-carbamic acid tert-butyl ester (0.78 g, 2.12 mmol) in ethanol (10 mL) and 4 M HCl (15 mL) was stirred at rt for 2 h. The hydrochloric acid was removed under reduced pressure and the crude reaction product extracted from a solution of 1 M NaOH (50 mL) with ethyl acetate (3×50 mL). The combined organic phases were dried over MgSO$_4$ and concentrated by evaporation under reduced pressure yielding 0.32 g (57%) of a white solid. The crude material was directly used in the following reaction step. MS (ISP): 269.0 [M+H]$^+$.

Step 3: 4-[1-(4-Chloro-3-ethoxy-benzyl)-piperidin-4-ylamino]-benzonitrile

A solution of 4-fluoro-benzonitrile (36.3 mg, 0.30 mmol, 1.0 equiv; commercially available) and 1-(4-chloro-3-ethoxy-benzyl)-piperidin-4-ylamine (96.8 mg, 0.36 mmol, 1.2 equiv; intermediate A2) in DMAc (2 mL) was heated by microwave irradiation to 210° C. for 3 h. Removal of the solvent under reduced pressure and purification by preparative HPLC on reversed phase eluting with a gradient of acetonitrile/water provided 10.9 mg (10%) of the title compound. MS (ISP): 370.1 [M+H]$^+$.

Example 3

N-{3-[1-(4-Chloro-3-ethoxy-benzyl)-piperidin-4-ylamino]-phenyl}-acetamide

Step 1: 4-(3-Acetylamino-phenylamino)-piperidine-1-carboxylic acid tert-butyl ester A mixture of N-(3-amino-phenyl)-acetamide (0.19 g, 1.25 mmol, 1.0 equiv; commercially available) and 4-oxo-piperidine-1-carboxylic acid tert-butyl ester (0.3 g, 1.50 mmol, 1.2 equiv; commercially available) in isopropanol (2 mL) was heated by microwave irradiation to 120° C. for 20 min. Sodium cyanoborohydride (0.16 g, 2.50 mmol, 2.0 equiv), dissolved in isopropanol (2 mL), was added and the reaction mixture heated by microwave irradiation to 120° C. for an additional time period of 20 min. The crude reaction material was purified by silica column chromatography eluting with heptane/ethyl acetate (1:2) providing 0.21 g (49%) of the title compound. MS (ISP): 334.3 [M+H]$^+$.

Step 2: N-[3-(Piperidin-4-ylamino)-phenyl]-acetamide dihydrochloride (Intermediate B1)

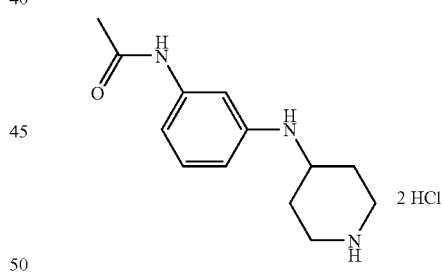

A solution of 4-(3-acetylamino-phenylamino)-piperidine-1-carboxylic acid tert-butyl ester (0.21 g, 0.63 mmol) in 4 M HCl in dioxane (10 mL) was stirred at rt for 2 h. The solvent was removed under reduced pressure and the crude product used in the consecutive step without further purification assuming quantitative deprotection and formation of the dihydrochloride salt. MS (ISP): 234.4 [M+H]$^+$.

Step 3: N-{3-[1-(4-Chloro-3-ethoxy-benzyl)-piperidin-4-ylamino]-phenyl}-acetamide To a solution of N-[3-(piperidin-4-ylamino)-phenyl]-acetamide dihydrochloride (61.2 mg, 0.2 mmol, 1.0 equiv; intermediate B1), acetic acid (60.1 mg, 1.0 mmol, 5.0 equiv) and triethylamine (40.5 mg, 0.4 mmol, 2.0 equiv) in ethanol (1 mL) was added 4-chloro-3-ethoxy-benzaldehyde (46.1 mg, 0.25 mmol, 1.25 equiv; intermediate E2, vide infra) and the mixture stirred at 50° C. After 1 h, sodium cyanoborohydride (15.1 mg, 0.24 mmol, 1.2 equiv), dissolved in ethanol (1 mL), was added and the mixture stirred at 50° C. over night. Removal of the solvent under reduced pressure and purification by preparative HPLC on reversed phase eluting with a gradient of acetonitrile/water provided 10.0 mg (12%) of the title compound. MS (ISP): 402.3 [M+H]+.

Example 4

N-{3-[1-(3,5-Diethoxy-4-fluoro-benzyl)-piperidin-4-ylamino]-phenyl}-acetamide

To a solution of N-[3-(piperidin-4-ylamino)-phenyl]-acetamide dihydrochloride (61.2 mg, 0.2 mmol, 1.0 equiv; intermediate B1), acetic acid (60.1 mg, 1.0 mmol, 5.0 equiv) and triethylamine (40.5 mg, 0.4 mmol, 2.0 equiv) in ethanol (1 mL) was added 3,5-diethoxy-4-fluoro-benzaldehyde (53.1 mg, 0.25 mmol, 1.25 equiv; intermediate E5, vide infra) and the mixture stirred at 50° C. After 1 h, sodium cyanoborohydride (15.1 mg, 0.24 mmol, 1.2 equiv), dissolved in ethanol (1 mL), was added and the mixture stirred at 50° C. over night. Removal of the solvent under reduced pressure and purification by preparative HPLC on reversed phase eluting with a gradient of acetonitrile/water provided 19.9 mg (23%) of the title compound. MS (ISP): 430.4 [M+H]+.

Example 5

[1-(3-Ethoxy-4-methoxy-benzyl)-piperidin-4-yl]-(4-ethyl-phenyl)-amine

Step 1: 1-(3-Ethoxy-4-methoxy-benzyl)-piperidin-4-one (Intermediate C1)

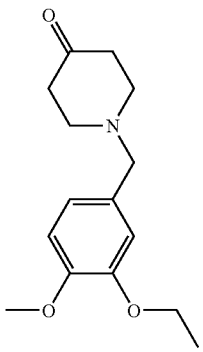

A mixture of 1,4-dioxa-8-aza-spiro[4.5]decane (9.33 g, 65.16 mmol, 1.0 equiv; commercially available) and 3-ethoxy-4-methoxy-benzaldehyde (14.09 g, 78.19 mmol, 1.2 equiv; commercially available) in ethanol (50 mL) and acetic acid (5 mL) was heated to 50° C. for 1 h. Sodium cyanoborohydride (4.91 g, 78.19 mmol, 1.2 equiv), dissolved in ethanol (20 mL), was added and the reaction mixture heated to 50° C. After 2 h, a solution of 37% HCl in water (100 mL) was added and the reaction mixture heated to 100° C. for 3 h. The solvent was removed under reduced pressure and the crude reaction product extracted from a solution of 1 M NaOH (100 mL) with ethyl acetate (3×100 mL). The combined organic phases were dried over $MgSO_4$, concentrated by evaporation under reduced pressure and the crude material purified with column chromatography on silica eluting with a gradient of heptane/ethyl acetate (1:3)→ethyl acetate to provide 11.23 g (59%) of the title compound. $^1$H NMR (300 MHz, $CDCl_3$): δ 1.46 (t, J=6.9 Hz, 3H), 2.41-2.44 (m, 4H), 2.69-2.73 (m, 4H), 3.53 (s, 2H), 3.87 (s, 3H), 4.11 (q, J=6.9 Hz, 2H), 6.80-6.86 (m, 2H), 6.94 (s, 1H). $^{13}$C NMR (75 MHz, $CDCl_3$): δ 14.49, 41.16, 52.71, 55.90, 61.00, 64.50, 111.43, 113.71, 121.04, 130.77, 148.17, 148.68, 208.71. MS (ISP): 263.9 [M+H]+.

Step 2: [1-(3-Ethoxy-4-methoxy-benzyl)-piperidin-4-yl]-(4-ethyl-phenyl)-amine

A solution of 1-(3-ethoxy-4-methoxy-benzyl)-piperidin-4-one (94.8 mg, 0.36 mmol, 1.2 equiv; intermediate C1) and 4-ethyl-phenylamine (36.4 mg, 0.30 mmol, 1.0 equiv; commercially available) in ethanol (2 mL) and acetic acid (0.38 mL) was heated to 85° C. After 2 h, sodium cyanoborohydride (22.6 mg, 0.36 mmol, 1.2 equiv), dissolved in ethanol (1 mL), was added and the mixture stirred at 85° C. over night. Removal of the solvent under reduced pressure and purification by preparative HPLC on reversed phase eluting with a gradient of acetonitrile/water provided 17.2 mg (16%) of the title compound. MS (ISP): 369.4 [M+H]+.

Examples 6 to 10

According to the procedure described for the synthesis of example 5/step 2 further phenyl derivatives have been synthesized from 1-(3-ethoxy-4-methoxy-benzyl)-piperidin-4-one (intermediate C1) and the respective aniline intermediate as indicated in Table 1. The results are compiled in Table 1 and comprise example 6 to example 10.

TABLE 1

| No | MW | Compound Name | Starting Materials | ISP [M + H]+ found |
|---|---|---|---|---|
| 6 | 447.60 | C-{4-[1-(3-Ethoxy-4-methoxy-benzyl)-piperidin-4-ylamino]-phenyl}-N-methyl-methanesulfonamide | 1-(3-ethoxy-4-methoxy-benzyl)-piperidin-4-one (intermediate C1) and C-(4-amino-phenyl)-N-methyl-methanesulfonamide (commercially available) | 448.1 |
| 7 | 430.57 | (2,2-dioxo-2,3-dihydro-1H-2λ$^6$-benzo[c]thiophen-5-yl)-[1-(3-ethoxy-4-methoxy-benzyl)- | 1-(3-ethoxy-4-methoxy-benzyl)-piperidin-4-one (intermediate C1) and 2,2-dioxo-2,3-dihydro-1H-2λ$^6$- | 431.3 |

TABLE 1-continued

| No | MW | Compound Name | Starting Materials | ISP [M + H]+ found |
|---|---|---|---|---|
|  |  | piperidin-4-yl]-amine | benzo[c]thiophen-5-ylamine (commercially available) |  |
| 8 | 384.48 | 4-[1-(3-ethoxy-4-methoxy-benzyl)-piperidin-4-ylamino]-benzoic acid | 1-(3-ethoxy-4-methoxy-benzyl)-piperidin-4-one (intermediate C1) and 4-amino-benzoic acid (commercially available) | 385.4 |
| 9 | 500.62 | 4-[1-(3-ethoxy-4-methoxy-benzyl)-piperidin-4-ylamino]-N-(5-methyl-isoxazol-3-yl)-benzenesulfonamide | 1-(3-ethoxy-4-methoxy-benzyl)-piperidin-4-one (intermediate C1) and 4-amino-N-(5-methyl-isoxazol-3-yl)-benzenesulfonamide (commercially available) | 501.2 |
| 10 | 433.57 | N-{4-[1-(3-ethoxy-4-methoxy-benzyl)-piperidin-4-ylamino]-phenyl}-methanesulfonamide | 1-(3-ethoxy-4-methoxy-benzyl)-piperidin-4-one (intermediate C1) and N-(4-amino-phenyl)-methanesulfonamide (commercially available) | 434.4 |

Example 11

[5-(1H-Benzoimidazol-2-yl)-pyridin-2-yl]-[1-(3-ethoxy-4-methoxy-benzyl)-piperidin-4-yl]-amine A solution of 2-(6-chloro-pyridin-3-yl)-1H-benzoimidazole (23.0 mg, 0.10 mmol, 1.0 equiv; commercially available) and 1-(3-ethoxy-4-methoxy-benzyl)-piperidin-4-ylamine (39.7 mg, 0.15 mmol, 1.5 equiv; intermediate A1) in ethylene glycol (2 mL) was heated by microwave irradiation to 220° C. for 20 min. Removal of the solvent under reduced pressure and purification by preparative HPLC on reversed phase eluting with a gradient of acetonitrile/water provided 4.0 mg (9%) of the title compound. MS (ISP): 456.6 [M−H]−.

Example 12

(7-Chloro-4-methoxymethyl-quinolin-2-yl)-[1-(3-ethoxy-4-methoxy-benzyl)-piperidin-4-yl]-amine Step 1: 2,7-Dichloro-4-methoxymethyl-quinoline To a solution of 4-bromomethyl-7-chloro-quinolin-2-ol (500.0 mg, 1.84 mmol, 1.0 equiv; [CAS RN 23976-53-6]; prepared according to R. J. Chudgar and K. N. Trivedi *J. Ind. Chem. Soc.* 1969, 46, 537-540) and collidine (333.5 mg, 2.75 mmol, 1.5 equiv) in acetonitril (15 mL) was added phosphorus oxychloride (1.0 mL, 1.69 g, 11.0 mmol, 6.0 equiv) and the reaction mixture heated to 110° C. over night. The reaction mixture was poured on ice, the pH adjusted to 9 by addition of a sat. solution of Na2CO3 (100 mL) and the solution extracted with ethyl acetate (3×50 mL). The organic phase was dried over Na2SO4 and concentrated by evaporation under reduced pressure yielding 0.43 g of a mixture of 4-bromomethyl-2,7-dichloro-quinoline and 2,7-dichloro-4-chloromethyl-quinoline according to 1H NMR, which was used directly in the consecutive step without further purification. The mixture was dissolved in MeOH (20 mL) and sodium methoxide (99.4 mg, 1.84 mmol, 1.0 equiv) was added. After heating to 60° C. for 8 h, the solvent was removed under reduced pressure and the crude material purified with silica column chromatography eluting with hexane/diethyl ether (10:1) to provide 0.17 g (38%) of the title compound. 1H NMR (250 MHz, CDCl3): δ 3.54 (s, 3H), 4.87 (s, 2H), 7.48 (s, 1H), 7.53 (dd, J=9.0 Hz, J=2.1 Hz, 1H), 7.86 (d, J=9.0 Hz, 1H), 8.03 (d, J=2.1 Hz, 1H). MS (EI): 242 [M]+.

Step 2: (7-Chloro-4-methoxymethyl-quinolin-2-yl)-[1-(3-ethoxy-4-methoxy-benzyl)-piperidin-4-yl]-amine A solution of 2,7-dichloro-4-methoxymethyl-quinoline (36.3 mg, 0.15 mmol, 1.0 equiv) and 1-(3-ethoxy-4-methoxy-benzyl)-piperidin-4-ylamine (47.6 mg, 0.18 mmol, 1.5 equiv; intermediate A1) in NMP (2 mL) was heated by microwave irradiation to 200° C. for 30 min. Removal of the solvent under reduced pressure and purification by preparative HPLC on reversed phase eluting with a gradient of acetonitrile/water provided 9.6 mg (14%) of the title compound. MS (ISP): 470.4 [M+H]+.

Example 13

[1-(3-Ethoxy-4-methoxy-benzyl)-piperidin-4-yl]-(6-fluoro-quinolin-2-yl)-amine

Step 1: 2-Chloro-6-fluoro-quinoline (Intermediate D1) [CAS RN 77119-53-0]

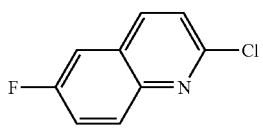

The title compound was prepared according to S. R. Inglis, C. Stojkoski, K. M. Branson, J. F. Cawthray, D. Fritz, E. Wiadrowski, S. M. Pyke and G. W. Booker *J. Med. Chem.* 2004, 47, 5405-5417.

Step 2: [1-(3-Ethoxy-4-methoxy-benzyl)-piperidin-4-yl]-(6-fluoro-quinolin-2-yl)-amine A solution of 2-chloro-6-fluoro-quinoline (27.2 mg, 0.15 mmol, 1.0 equiv; intermediate D1) and 1-(3-ethoxy-4-methoxy-benzyl)-piperidin-4-ylamine (47.6 mg, 0.18 mmol, 1.2 equiv; intermediate A1) in DMAc (2 mL) was heated by microwave irradiation to 220° C. for 1 h. Removal of the solvent under reduced pressure and purification by prepara-

Example 14

6-[1-(3-Ethoxy-4-methoxy-benzyl)-piperidin-4-ylamino]-nicotinonitrile

Method A:

A solution of 6-chloro-nicotinonitrile (20.8 mg, 0.15 mmol, 1.0 equiv; commercially available) and 1-(3-ethoxy-4-methoxy-benzyl)-piperidin-4-ylamine (47.6 mg, 0.18 mmol, 1.2 equiv; intermediate A1) in DMAc (1.5 mL) was heated by microwave irradiation to 180° C. for 10 min. Removal of the solvent under reduced pressure and purification by preparative HPLC on reversed phase eluting with a gradient of acetonitrile/water provided 2.2 mg (4%) of the title compound. MS (ISP): 367.3 [M+H]$^+$.

Example 15

[1-(3-Ethoxy-4-methoxy-benzyl)-piperidin-4-yl]-(5-trifluoromethyl-pyridin-2-yl)-amine Method B:

To a solution of 1-(3-ethoxy-4-methoxy-benzyl)-piperidin-4-ylamine (39.7 mg, 0.15 mmol, 1.2 equiv; intermediate A1) in dry DMF (1.5 mL) under Ar was added sodium hydride (6.6 mg, 0.15 mmol, 1.2 equiv; 55% free-flowing powder moistened with oil) and the reaction mixture stirred at rt. After 2 h, 2-chloro-5-trifluoromethyl-pyridine (22.7 mg, 0.125 mmol, 1.0 equiv; commercially available) was added and the mixture heated by microwave irradiation to 160° C. for 15 min. Removal of the solvent under reduced pressure and purification by preparative HPLC on reversed phase eluting with a gradient of acetonitrile/water provided 4.8 mg (8%) of the title compound. MS (ISP): 410.3 [M+H]$^+$.

Example 16

(6-Chloro-pyridin-2-yl)-[1-(3-ethoxy-4-methoxy-benzyl)-piperidin-4-yl]-amine Method C:

To a solution of 1-(3-ethoxy-4-methoxy-benzyl)-piperidin-4-ylamine (39.7 mg, 0.15 mmol, 1.2 equiv; intermediate A1) in dry DMF (1.5 mL) under Ar was added sodium hydride (6.6 mg, 0.15 mmol, 1.2 equiv; 55% free-flowing powder moistened with oil) and the reaction mixture stirred at rt. After 2 h, 2,6-dichloro-pyridine (18.5 mg, 0.125 mmol, 1.0 equiv; commercially available) was added and the mixture heated by microwave irradiation to 140° C. for 1 h. Removal of the solvent under reduced pressure and purification by preparative HPLC on reversed phase eluting with a gradient of acetonitrile/water provided 1.1 mg (2%) of the title compound. MS (ISP): 376.3 [M+H]$^+$.

Example 17

6-[1-(3-Ethoxy-4-methoxy-benzyl)-piperidin-4-ylamino]-nicotinic acid ethyl ester Method D:

To a solution of 1-(3-ethoxy-4-methoxy-benzyl)-piperidin-4-ylamine (39.7 mg, 0.15 mmol, 1.0 equiv; intermediate A1) in dry DMF (1.5 mL) under Ar was added sodium hydride (6.6 mg, 0.15 mmol, 1.0 equiv; 55% free-flowing powder moistened with oil) and the reaction mixture stirred at rt. After 2 h, 6-chloro-nicotinic acid ethyl ester (46.4 mg, 0.25 mmol, 1.67 equiv; commercially available) was added and the mixture heated by microwave irradiation to 220° C. for 15 min. Removal of the solvent under reduced pressure and purification by preparative HPLC on reversed phase eluting with a gradient of acetonitrile/water provided 10.9 mg (18%) of the title compound. MS (ISP): 414.4 [M+H]$^+$.

Examples 18 to 27

According to the procedure described for the synthesis of example 14 (Method A), example 15 (Method B), example 16 (Method C) and example 17 (Method D) further pyridine, quinoline and naphthyridine derivatives have been synthesized from 1-(3-ethoxy-4-methoxy-benzyl)-piperidin-4-ylamine (intermediate A1) and the respective pyridine, quinoline and naphthyridine intermediate as indicated in Table 2. The results are compiled in Table 2 and comprise example 18 to example 27.

TABLE 2

| No | MW | Compound Name | Preparation | Starting Materials | ISP [M + H]$^+$ found |
|---|---|---|---|---|---|
| 18 | 399.49 | 6-[1-(3-ethoxy-4-methoxy-benzyl)-piperidin-4-ylamino]-nicotinic acid methyl ester | Method B | 1-(3-ethoxy-4-methoxy-benzyl)-piperidin-4-ylamine (intermediate A1) and 6-chloro-nicotinic acid methyl ester (commercially available) | 400.4 |
| 19 | 386.45 | [1-(3-ethoxy-4-methoxy-benzyl)-piperidin-4-yl]-(5-nitro-pyridin-2-yl)-amine | Method A | 1-(3-ethoxy-4-methoxy-benzyl)-piperidin-4-ylamine (intermediate A1) and 2-chloro-5-nitro-pyridine (commercially available) | 387.3 |
| 20 | 420.36 | (5-bromo-pyridin-2-yl)-[1-(3-ethoxy-4-methoxy-benzyl)-piperidin-4-yl]-amine | Method D | 1-(3-ethoxy-4-methoxy-benzyl)-piperidin-4-ylamine (intermediate A1) and 5-bromo-2-chloro-pyridine (commercially available) | 422.2 |
| 21 | 400.48 | [1-(3-ethoxy-4-methoxy-benzyl)- | Method C | 1-(3-ethoxy-4-methoxy-benzyl)-piperidin-4- | 401.4 |

TABLE 2-continued

| No | MW | Compound Name | Preparation | Starting Materials | ISP [M + H]+ found |
|----|------|---------------|-------------|--------------------|--------------------|
|    |      | piperidin-4-yl]-(6-methyl-5-nitro-pyridin-2-yl)-amine |  | ylamine (intermediate A1) and 6-chloro-2-methyl-3-nitro-pyridine (commercially available) |  |
| 22 | 401.47 | N6-[1-(3-ethoxy-4-methoxy-benzyl)-piperidin-4-yl]-3-nitro-pyridine-2,6-diamine | Method C | 1-(3-ethoxy-4-methoxy-benzyl)-piperidin-4-ylamine (intermediate A1) and 6-chloro-3-nitro-pyridin-2-ylamine (commercially available) | 402.4 |
| 23 | 433.94 | 2-chloro-6-[1-(3-ethoxy-4-methoxy-benzyl)-piperidin-4-ylamino]-isonicotinic acid methyl ester | Method C | 1-(3-ethoxy-4-methoxy-benzyl)-piperidin-4-ylamine (intermediate A1) and 2,6-dichloro-isonicotinic acid methyl ester (commercially available) | 434.3 |
| 24 | 456.59 | 2-[1-(3-ethoxy-4-methoxy-benzyl)-piperidin-4-ylamino]-6-methyl-5-phenyl-nicotinonitrile | Method C | 1-(3-ethoxy-4-methoxy-benzyl)-piperidin-4-ylamine (intermediate A1) and 2-chloro-6-methyl-5-phenyl-nicotinonitrile (commercially available) | 457.4 |
| 25 | 418.90 | 2-chloro-6-[1-(3-ethoxy-4-methoxy-benzy)-piperidin-4-ylamino]-5-fluoro-nicotinonitrile | Method C | 1-(3-ethoxy-4-methoxy-benzyl)-piperidin-4-ylamine (intermediate A1) and 2,6-dichloro-5-fluoro-nicotinonitrile (commercially available) | 419.2 |
| 26 | 391.51 | [1-(3-ethoxy-4-methoxy-benzyl)-piperidin-4-yl]-quinolin-2-yl-amine | Method D | 1-(3-ethoxy-4-methoxy-benzyl)-piperidin-4-ylamine (intermediate A1) and 2-chloro-quinoline (commercially available) | 392.2 |
| 27 | 406.53 | [1-(3-ethoxy-4-methoxy-benzyl)-piperidin-4-yl]-(5-methyl-[1,6]naphthyridin-2-yl)-amine | Method C | 1-(3-ethoxy-4-methoxy-benzyl)-piperidin-4-ylamine (intermediate A1) and 2-chloro-5-methyl-[1,6]naphthyridine (commercially available) | 407.4 |

Example 28

{2-Chloro-6-[1-(4-chloro-3-ethoxy-benzyl)-piperidin-4-ylamino]-pyridin-4-yl}-methanol Method E:

A solution of (2,6-dichloro-pyridin-4-yl)-methanol (44.5 mg, 0.25 mmol, 1.25 equiv; commercially available) and 1-(4-chloro-3-ethoxy-benzyl)-piperidin-4-ylamine (53.8 mg, 0.20 mmol, 1.2 equiv; intermediate A2) in DMF (2.0 mL) was heated by microwave irradiation to 220° C. for 1 h. Removal of the solvent under reduced pressure and purification by preparative HPLC on reversed phase eluting with a gradient of acetonitrile/water provided 3.2 mg (4%) of the title compound. MS (ISP): 410.3 [M+H]+.

The pyridine intermediate D2 was prepared following literature precedents.

Synthesis of Pyridine Intermediate D2 to be used in Table 3

Intermediate D2

2,6-Dichloro-4-methoxymethyl-pyridine [CAS RN 221093-39-6]

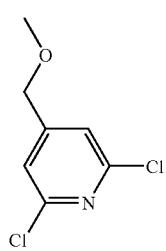

The title compound was prepared according to WO 99/12907 (Dainippon Ink and Chemicals, Inc.).

Examples 29 to 37

According to the procedure described for the synthesis of example 15 (Method B), example 16 (Method C) and example 28 (Method E) further pyridine, quinoline and naphthyridine derivatives have been synthesized from 1-(4-chloro-3-ethoxy-benzyl)-piperidin-4-ylamine (intermediate A2) and the respective pyridine, quinoline and naphthyridine intermediate as indicated in Table 3. The results are compiled in Table 3 and comprise example 29 to example 37.

TABLE 3

| No | MW | Compound Name | Preparation | Starting Materials | ISP [M + H]+ found |
|---|---|---|---|---|---|
| 29 | 403.91 | 6-[1-(4-chloro-3-ethoxy-benzyl)-piperidin-4-ylamino]-nicotinic acid methyl ester | Method B | 1-(4-chloro-3-ethoxy-benzyl)-piperidin-4-ylamine (intermediate A2) and 6-chloro-nicotinic acid methyl ester (commercially available) | 404.4 |
| 30 | 413.87 | [1-(4-chloro-3-ethoxy-benzyl)-piperidin-4-yl]-(5-trifluoromethyl-pyridin-2-yl)-amine | Method C | 1-(4-chloro-3-ethoxy-benzyl)-piperidin-4-ylamine (intermediate A2) and 2-chloro-5-trifluoromethyl-pyridine (commercially available) | 414.3 |
| 31 | 413.87 | [1-(4-chloro-3-ethoxy-benzyl)-piperidin-4-yl]-(3-trifluoromethyl-pyridin-2-yl)-amine | Method C | 1-(4-chloro-3-ethoxy-benzyl)-piperidin-4-ylamine (intermediate A2) and 2-chloro-3-trifluoromethyl-pyridine (commercially available) | 414.3 |
| 32 | 404.90 | [1-(4-chloro-3-ethoxy-benzyl)-piperidin-4-yl]-(6-methyl-5-nitro-pyridin-2-yl)-amine | Method C | 1-(4-chloro-3-ethoxy-benzyl)-piperidin-4-ylamine (intermediate A2) and 6-chloro-2-methyl-3-nitro-pyridine (commercially available) | 405.3 |
| 33 | 405.89 | $N^6$-[1-(4-chloro-3-ethoxy-benzyl)-piperidin-4-yl]-3-nitro-pyridine-2,6-diamine | Method C | 1-(4-chloro-3-ethoxy-benzyl)-piperidin-4-ylamine (intermediate A2) and 6-chloro-3-nitro-pyridin-2-ylamine (commercially available) | 406.4 |
| 34 | 424.37 | [1-(4-chloro-3-ethoxy-benzyl)-piperidin-4-yl]-(6-chloro-4-methoxymethyl-pyridin-2-yl)-amine | Method E | 1-(4-chloro-3-ethoxy-benzyl)-piperidin-4-ylamine (intermediate A2) and 2,6-dichloro-4-methoxymethyl-pyridine (intermediate D2) | 424.1 |
| 35 | 384.91 | 2-[1-(4-chloro-3-ethoxy-benzyl)-piperidin-4-ylamino]-6-methyl-nicotinonitrile | Method C | 1-(4-chloro-3-ethoxy-benzyl)-piperidin-4-ylamine (intermediate A2) and 2-chloro-6-methyl-nicotinonitrile (commercially available) | 385.4 |
| 36 | 413.92 | [1-(4-chloro-3-ethoxy-benzyl)-piperidin-4-yl]-(6-fluoro-quinolin-2-yl)-amine | Method E | 1-(4-chloro-3-ethoxy-benzyl)-piperidin-4-ylamine (intermediate A2) and 2-chloro-6-fluoro-quinoline (intermediate D1) | 414.4 |
| 37 | 410.95 | [1-(4-chloro-3-ethoxy-benzyl)-piperidin-4-yl]-(5-methyl-[1,6]naphthyridin-2-yl)-amine | Method C | 1-(4-chloro-3-ethoxy-benzyl)-piperidin-4-ylamine (intermediate A2) and 2-chloro-5-methyl-[1,6]naphthyridine (commercially available) | 411.5 |

Example 38

6-[1-(3-Ethoxy-4-methyl-benzyl)-piperidin-4-ylamino]-nicotinonitrile

Step 1: 4-(5-Cyano-pyridin-2-ylamino)-piperidine-1-carboxylic acid tert-butyl ester A mixture of 6-chloro-nicotinonitrile (2.1 g, 15.16 mmol, 1.0 equiv; commercially available) and 4-amino-piperidine-1-carboxylic acid tert-butyl ester (4.86 g, 24.25 mmol, 1.6 equiv; commercially available) in N-ethyl diisopropylamine (5 mL) and anhydrous DMF (10 mL) was stirred at 60° C. for 3 d. To the reaction mixture was added a sat. solution of Na$_2$CO$_3$ (100 mL) and the crude extracted with ethyl acetate (3×100 mL). The combined organic phases were dried over MgSO$_4$, concentrated by evaporation under reduced pressure and the crude material purified with silica column chromatography eluting with toluene/ethyl acetate (4:1) to provide 2.90 g (63%) of the title compound. $^1$H NMR (300 MHz, DMSO): δ 1.24-1.42 (m, 2H), 1.41 (s, 9H), 1.84-1.89 (m, 2H), 2.85-2.94 (m, 2H), 3.87-3.91 (m, 2H), 3.98 (br s, 1H), 6.54 (d, J=8.9 Hz, 1H), 7.53 (d, J=7.5 Hz, 1H), 7.66 (dd, J=8.9 Hz, J=2.1 Hz, 1H), 8.38 (d, J=2.1 Hz, 1H), $^{13}$C NMR (75 MHz, DMSO): δ 828.04, 31.19, 42.25, 47.12, 78.58, 94.49, 108.62, 118.91, 138.53, 153.00, 153.89, 159.17. MS (ISP): 303.1 [M+H]$^+$.

Step 2: 6-(Piperidin-4-ylamino)-nicotinonitrile dihydrochloride (Intermediate B2)

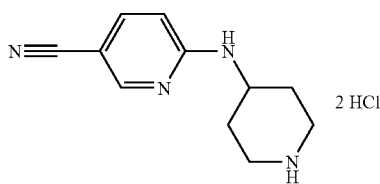

A solution of 4-(5-cyano-pyridin-2-ylamino)-piperidine-1-carboxylic acid tert-butyl ester (2.6 g, 8.60 mmol) in 4 M HCl in dioxane (20 mL) was stirred at rt for 1 h. The solvent was removed under reduced pressure and the crude product used in the consecutive step without further purification assuming quantitative deprotection and formation of the dihydrochloride salt. MS (ISP): 203.3 [M+H]$^+$.

Step 3: 6-[1-(3-Ethoxy-4-methyl-benzyl)-piperidin-4-ylamino]-nicotinonitrile To a solution of 6-(piperidin-4-ylamino)-nicotinonitrile dihydrochloride (41.3 mg, 0.15 mmol, 1.0 equiv; intermediate B2) in ethanol (2 mL), acetic acid (72.1 mg, 1.2 mmol, 8.0 equiv) and N-ethyl diisopropylamine (77.6 mg, 0.6 mmol, 4.0 equiv) was added 3-ethoxy-4-methyl-benzaldehyde (29.6 mg, 0.18 mmol, 1.2 equiv; intermediate E10, vide infra) and the mixture stirred at 55° C. After 1 h, sodium cyanoborohydride (47.1 mg, 0.75 mmol, 5.0 equiv), dissolved in ethanol (0.5 mL), was added and the mixture stirred at 55° C. over night. Removal of the solvent under reduced pressure and purification by preparative HPLC on reversed phase eluting with a gradient of acetonitrile/water provided 20.5 mg (39%) of the title compound. MS (ISP): 350.7 [M+H]$^+$.

The pyridine, quinoline, isoquinoline and pyrazine piperidine intermediates B3 to B14 were prepared following literature precedents or as described below.

Synthesis of Pyridine, Quinoline, Isoquinoline and Pyrazine Piperidine Intermediates B3 to B14 to be used in Table 4

Intermediate B3

6-(Piperidin-4-ylamino)-nicotinamide dihydrochloride

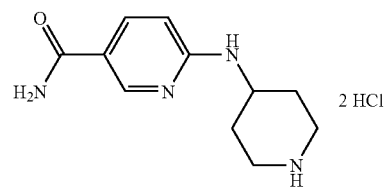

Step 1: 4-(5-Carbamoyl-pyridin-2-ylamino)-piperidine-1-carboxylic acid tert-butyl ester To a solution of 4-(5-cyano-pyridin-2-ylamino)-piperidine-1-carboxylic acid tert-butyl ester (0.40 g, 1.32 mmol, 1.0 equiv; example 38/step 1) in DMSO (2.5 mL) was added potassium carbonate (0.037 g, 0.27 mmol, 0.2 equiv) and a solution of 30% hydrogen peroxide in water (0.27 mL, 0.30 g, 2.65 mmol, 2.0 equiv). The reaction mixture was stirred for 1 h at rt and then extracted from water (50 mL) with ethyl acetate (3×50 mL). The combined organic phases were dried over MgSO$_4$ and concentrated by evaporation under reduced pressure yielding 0.63 g (74%) of the title compound, which was used in the consecutive step without further purification. $^1$H NMR (300 MHz, CDCl$_3$): δ 1.38-1.46 (m, 2H), 1.46 (s, 9H), 1.98-2.03 (m, 2H), 2.90-2.93 (m, 2H), 3.79-3.91 (m, 1H), 4.01-4.06 (m, 2H), 5.48 (d, J=8.1 Hz, 1H), 6.39 (d, J=8.8 Hz, 1H), 6.59 (br s, 2H), 7.87 (dd, J=8.8 Hz, J=2.1 Hz, 1H), 8.59 (d, J=2.1 Hz, 1H). $^{13}$C NMR (75 MHz, CDCl$_3$): δ 28.38, 31.75, 42.50, 48.18, 79.52, 106.81, 117.65, 136.65, 148.75, 154.68, 159.45, 168.70. MS (ISP): 321.4 [M+H]$^+$.

Step 2: 6-(Piperidin-4-ylamino)-nicotinamide dihydrochloride

A solution of 4-(5-carbamoyl-pyridin-2-ylamino)-piperidine-1-carboxylic acid tert-butyl ester (0.63 g, 1.97 mmol) in 4 M HCl in dioxane (20 mL) was stirred at rt for 1 h. The solvent was removed under reduced pressure and the crude product used in the consecutive step without further purification assuming quantitative deprotection and formation of the dihydrochloride salt. MS (ISP): 221.4 [M+H]$^+$.

Intermediate B4

6-(Piperidin-4-ylamino)-nicotinic acid dihydrochloride

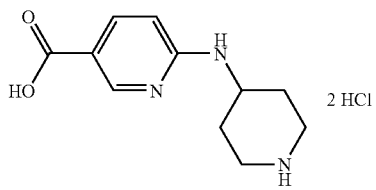

Step 1: 6-(1-tert-Butoxycarbonyl-piperidin-4-ylamino)-nicotinic acid

To a solution of 4-(5-cyano-pyridin-2-ylamino)-piperidine-1-carboxylic acid tert-butyl ester (1.00 g, 3.31 mmol, 1.0 equiv; example 38/step 1) in ethanol (10 mL) was added a solution of 5 M NaOH (3.31 mL, 16.54 mmol, 5.0 equiv) and the reaction mixture heated by microwave irradiation to 120° C. for 15 min. The solvent was evaporated under reduced pressure and the crude material purified by silica column chromatography using a MPLC system (CombiFlash Companion, Isco Inc.) eluting with a gradient of dichloromethane/methanol providing 0.46 g (39%) of the title compound. $^1$H NMR (300 MHz, DMSO): δ 1.18-1.31 (m, 2H), 1.40 (s, 9H), 1.84-1.88 (m, 2H), 2.83-2.93 (m, 2H), 3.86-3.90 (m, 2H), 3.90-4.03 (m, 1H), 6.43 (d, J=8.8 Hz, 1H), 7.05 (d, J=8.1 Hz, 1H), 7.81 (dd, J=8.8 Hz, J=2.2 Hz, 1H), 8.54 (d, J=2.2 Hz, 1H). MS (ISP): 322.4 [M+H]$^+$.

Step 2: 6-(Piperidin-4-ylamino)-nicotinic acid dihydrochloride

A solution of 6-(1-tert-butoxycarbonyl-piperidin-4-ylamino)-nicotinic acid (0.46 g, 1.43 mmol) in ethanol (40 mL) and 4 M HCl in dioxane (40 mL) was stirred at rt for 1 h. The solvent was removed under reduced pressure and the crude product used in the consecutive step without further purification assuming quantitative deprotection and formation of the dihydrochloride salt. MS (ISP): 222.3 [M+H]$^+$.

Intermediate B5

Piperidin-4-yl-[5-(1H-tetrazol-5-yl)-pyridin-2-yl]-amine dihydrochloride

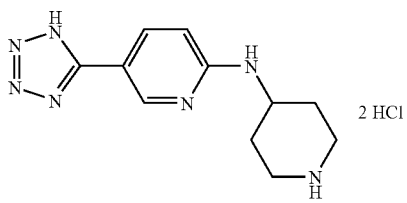

Step 1: 4-[5-(1H-Tetrazol-5-yl)-pyridin-2-ylamino]-piperidine-1-carboxylic acid tert-butyl ester To a solution of 4-(5-cyano-pyridin-2-ylamino)-piperidine-1-carboxylic acid tert-butyl ester (0.70 g, 2.32 mmol, 1.0 equiv; example 38/step 1) in anhydrous DMF (8 mL) was added sodium azide (0.45 g, 6.95 mmol, 3.0 equiv) and ammonium chloride (0.37 g, 6.95 mmol, 3.0 equiv) and the reaction mixture heated by microwave irradiation to 150° C. for 1.5 h. The solvent was evaporated under reduced pressure and the crude material purified with column chromatography on silica eluting with dichloromethane/methanol (9:1) to yield 0.80 g (100%) of the title compound. $^1$H NMR (300 MHz, CH$_3$OD): δ 1.28-1.44 (m, 2H), 1.42 (s, 9H), 1.89-1.93 (m, 2H), 2.85-2.93 (m, 2H), 3.81-3.90 (m, 1H), 3.93-3.97 (m, 2H), 6.56 (d, J=8.9 Hz, 1H), 7.90 (dd, J=8.9 Hz, J=2.3 Hz, 1H), 8.52 (d, J=2.3 Hz, 1H). MS (ISP): 346.1 [M+H]$^+$.

Step 2: Piperidin-4-yl-[5-(1H-tetrazol-5-yl)-pyridin-2-yl]-amine dihydrochloride A solution of 4-[5-(1H-tetrazol-5-yl)-pyridin-2-ylamino]-piperidine-1-carboxylic acid tert-butyl ester (0.80 g, 2.32 mmol) in 4 M HCl in dioxane (60 mL) was stirred at rt for 2 h. The solvent was removed under reduced pressure and the crude product used in the consecutive step without further purification assuming quantitative deprotection and formation of the dihydrochloride salt. MS (ISP): 246.4 [M+H]$^+$.

Intermediate B6

Piperidin-4-yl-(5-trifluoromethyl-pyridin-2-yl)-amine dihydrochloride

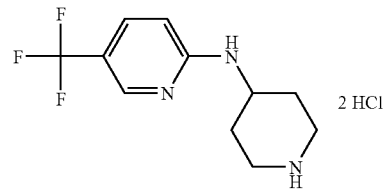

Step 1: 4-(5-Trifluoromethyl-pyridin-2-ylamino)-piperidine-1-carboxylic acid tert-butyl ester A solution of 2-chloro-5-trifluoromethyl-pyridine (2.45 g, 13.50 mmol, 1.0 equiv; commercially available) and 4-amino-piperidine-1-carboxylic acid tert-butyl ester (3.24 g, 16.19 mmol, 1.2 equiv; commercially available) in DMAc (12 mL) was heated by microwave irradiation to 155° C. for 6 h. A solution of 1 M NaOH (100 mL) was added and the reaction mixture extracted with ethyl acetate (3×100 mL). The combined organic phases were dried over MgSO$_4$, concentrated by evaporation under reduced pressure and the crude material purified with column chromatography on silica eluting with a gradient of heptane/ethyl acetate (4:1→1:1) to yield 0.69 g (15%) of the title compound. $^1$H NMR (300 MHz, CDCl$_3$): δ 1.31-1.47 (m, 2H), 1.40 (s, 9H), 1.92-1.98 (m, 2H), 2.81-2.92 (m, 2H), 3.72-3.83 (m, 1H), 3.97-4.03 (m, 2H), 4.77 (d, J=8.1 Hz, 1H), 6.31 (d, J=8.8 Hz, 1H), 7.62 (dd, J=8.8 Hz, J=2.2 Hz, 1H), 8.25 (br s, 1H). $^{13}$C NMR (75 MHz, CDCl$_3$): δ 27.45, 31.17, 41.64, 47.51, 78.72, 105.86, 114.65 (q, J=32.8 Hz), 123.58 (q, J=268.6 Hz), 133.26, 145.15, 153.76, 158.36. $^{19}$F NMR (282 MHz, CDCl$_3$): δ-61.22. MS (ISP): 346.1 [M+H]$^+$.

Step 2: Piperidin-4-yl-(5-trifluoromethyl-pyridin-2-yl)-amine dihydrochloride A solution of 4-(5-trifluoromethyl-pyridin-2-ylamino)-piperidine-1-carboxylic acid tert-butyl ester (0.69 g, 2.00 mmol) in ethanol (40 mL) and 4 M HCl in dioxane (40 mL) was stirred at rt for 1 h. The solvent was removed under reduced pressure and the crude product used in the consecutive step without further purification assuming quantitative deprotection and formation of the dihydrochloride salt. MS (ISP): 246.1 [M+H]⁺.

Intermediate B7

6-(Piperidin-4-ylamino)-4-trifluoromethyl-nicotinic acid methyl ester dihydrochloride

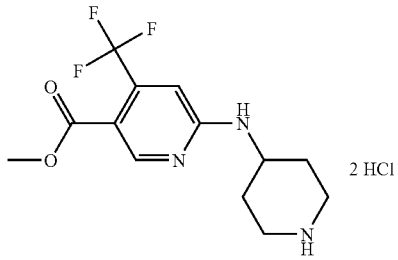

Step 1: 6-(1-tert-Butoxycarbonyl-piperidin-4-ylamino)-4-trifluoromethyl-nicotinic acid methyl ester A solution of 6-chloro-4-trifluoromethyl-nicotinic acid methyl ester (2.00 g, 8.35 mmol, 1.0 equiv; commercially available) and 4-amino-piperidine-1-carboxylic acid tert-butyl ester (2.01 g, 10.02 mmol, 1.2 equiv; commercially available) in anhydrous DMF (10 mL) was heated by microwave irradiation to 110° C. for 4 h. A solution of 1 M NaOH (100 mL) was added and the reaction mixture extracted with ethyl acetate (3×100 mL). The combined organic phases were dried over MgSO₄, concentrated by evaporation under reduced pressure and the crude material purified with column chromatography on silica eluting with a gradient of heptane/ethyl acetate (5:1→3:1) to yield 1.65 g (49%) of the title compound. ¹H NMR (300 MHz, CDCl₃): δ 1.36-1.41 (m, 2H), 1.40 (s, 9H), 1.95-1.97 (m, 2H), 2.85-2.93 (m, 2H), 3.81 (s, 3H), 3.92-3.98 (m, 1H), 3.98-4.05 (m, 2H), 5.12 (d, J=8.1 Hz, 1H), 6.59 (s, 1H), 8.68 (s, 1H). ¹⁹F NMR (282 MHz, CDCl₃): δ-62.38. MS (ISP): 404.5 [M+H]⁺.

Step 2: 6-(Piperidin-4-ylamino)-4-trifluoromethyl-nicotinic acid methyl ester dihydrochloride A solution of 6-(1-tert-butoxycarbonyl-piperidin-4-ylamino)-4-trifluoromethyl-nicotinic acid methyl ester (1.65 g, 4.09 mmol) in THF (10 mL) and 4 M HCl in dioxane (20 mL) was stirred at rt for 1 h. The solvent was removed under reduced pressure and the crude product used in the consecutive step without further purification assuming quantitative deprotection and formation of the dihydrochloride salt. MS (ISP): 304.0 [M+H]⁺.

Intermediate B8

Piperidin-4-yl-quinolin-2-yl-amine dihydrochloride

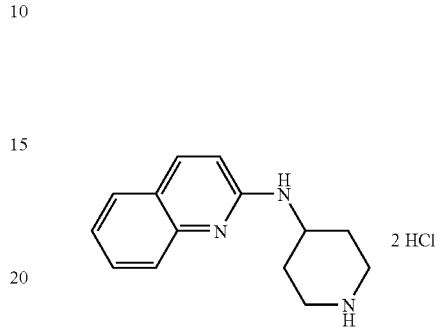

Step 1:
4-(Quinolin-2-ylamino)-piperidine-1-carboxylic acid tert-butyl ester

To a degassed solution of 2-chloro-quinoline (1.00 g, 6.11 mmol, 1.0 equiv; commercially available) and 4-amino-piperidine-1-carboxylic acid tert-butyl ester (1.47 g, 7.33 mmol, 1.2 equiv; commercially available) in dimethoxyethane (15 mL) was added KOtert-Bu (0.96 g, 8.56 mmol, 1.4 equiv), (R)-(−)-1-[(S)-2-(dicyclohexyl-phosphino)-ferrocenyl]ethyl-di-tert-butylphosphine (3.39 mg, 0.0061 mmol, 0.1 mol %; Josiphos ligand [CAS RN 158923-11-6]; commercially available from Strem Chemicals, USA) and palladium(II) acetate (1.37 mg, 0.0061 mmol, 0.1 mol %). The reaction mixture was stirred at 90° C. for 4 h, concentrated by evaporation under reduced pressure and the residue purified by silica column chromatography using a MPLC system (CombiFlash Companion, Isco Inc.) eluting with a gradient of heptane (+1% triethylamine)/ethyl acetate providing 1.0 g (50%) of the title compound. ¹H NMR (300 MHz, DMSO): δ 1.28-1.41 (m, 2H), 1.42 (s, 9H), 1.93-1.94 (m, 2H), 2.95-3.02 (m, 2H), 3.87-3.92 (m, 2H), 4.11-4.19 (m, 1H), 6.74 (d, J=8.9 Hz, 1H), 6.94 (d, J=7.6 Hz, 1H), 7.10-7.16 (m, 1H), 7.42-7.51 (m, 2H), 7.59 (d, J=7.6 Hz, 1H), 7.83 (d, J=8.9 Hz, 1H). ¹³C NMR (75 MHz, DMSO): δ 28.07, 31.49, 42.41, 46.52, 78.52, 113.21, 121.03, 122.80, 125.52, 127.42, 128.89, 136.18, 147.82, 153.92, 156.13. MS (ISP): 328.5 [M+H]⁺.

Step 2: Piperidin-4-yl-quinolin-2-yl-amine dihydrochloride

A solution of 4-(quinolin-2-ylamino)-piperidine-1-carboxylic acid tert-butyl ester (1.00 g, 3.05 mmol) in 4 M HCl in dioxane (100 mL) was stirred at rt for 1 h. The solvent was removed under reduced pressure and the crude product used in the consecutive step without further purification assuming quantitative deprotection and formation of the dihydrochloride salt. MS (ISP): 228.6 [M+H]+.

Intermediate B9

(4-Methyl-quinolin-2-yl)-piperidin-4-yl-amine dihydrochloride

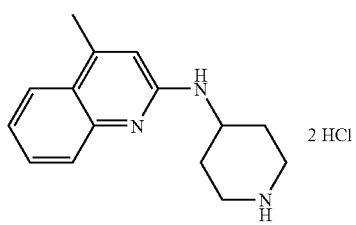

2 HCl

Step 1: 4-(4-Methyl-quinolin-2-ylamino)-piperidine-1-carboxylic acid tert-butyl ester To a degassed solution of 2-chloro-4-methyl-quinoline (1.00 g, 5.63 mmol, 1.0 equiv; commercially available) and 4-amino-piperidine-1-carboxylic acid tert-butyl ester (1.35 g, 6.76 mmol, 1.2 equiv; commercially available) in dimethoxyethane (15 mL) was added KOtert-Bu (0.88 g, 7.88 mmol, 1.4 equiv), (R)-(−)-1-[(S)-2-(dicyclohexyl-phosphino)-ferrocenyl]ethyl-di-tert-butylphosphine (3.12 mg, 0.0056 mmol, 0.1 mol %; Josiphos ligand [CAS RN 158923-11-6]; commercially available from Strem Chemicals, USA) and palladium (II) acetate (1.26 mg, 0.0056 mmol, 0.1 mol %). The reaction mixture was stirred at 90° C. for 18 h, concentrated by evaporation under reduced pressure and the residue purified by silica column chromatography using a MPLC system (CombiFlash Companion, Isco Inc.) eluting with a gradient of heptane (+1% triethylamine)/ethyl acetate providing 0.54 g (28%) of the title compound. $^1$H NMR (300 MHz, DMSO): δ 1.31-1.40 (m, 2H), 1.41 (s, 9H), 1.91-1.96 (m, 2H), 2.46 (s, 3H), 2.93-3.01 (m, 2H), 3.86-3.91 (m, 2H), 4.11-4.17 (m, 1H), 6.59 (s, 1H), 6.80 (d, J=7.7 Hz, 1H), 7.13-7.17 (m, 1H), 7.44-7.47 (m, 2H), 7.73 (d, J=7.7 Hz, 1H). $^{13}$C NMR (75 MHz, DMSO): δ 18.16, 28.07, 31.57, 42.39, 46.37, 78.51, 112.89, 120.88, 123.12, 123.64, 125.96, 128.69, 143.28, 147.91, 153.91, 155.93. MS (ISP): 342.5 [M+H]+.

Step 2: (4-Methyl-quinolin-2-yl)-piperidin-4-yl-amine dihydrochloride

A solution of 4-(4-methyl-quinolin-2-ylamino)-piperidine-1-carboxylic acid tert-butyl ester (0.54 g, 1.58 mmol) in 4 M HCl in dioxane (50 mL) was stirred at rt for 1 h. The solvent was removed under reduced pressure and the crude product used in the consecutive step without further purification assuming quantitative deprotection and formation of the dihydrochloride salt. MS (ISP): 242.4 [M+H]+.

Intermediate B10

(4-Chloro-quinolin-2-yl)-piperidin-4-yl-amine dihydrochloride

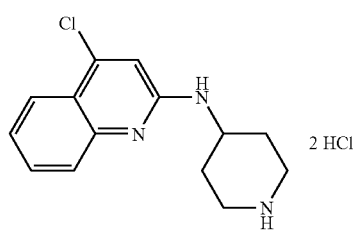

2 HCl

Step 1: 4-(4-Chloro-quinolin-2-ylamino)-piperidine-1-carboxylic acid tert-butyl ester To a degassed solution of 2,4-dichloro-quinoline (1.00 g, 5.05 mmol, 1.0 equiv; commercially available from Specs Research Laboratory, The Netherlands) and 4-amino-piperidine-1-carboxylic acid tert-butyl ester (1.21 g, 6.06 mmol, 1.2 equiv; commercially available) in dimethoxyethane (15 mL) was added KOtert-Bu (0.79 g, 7.07 mmol, 1.4 equiv), (R)-(−)-1-[(S)-2-(dicyclohexyl-phosphino)-ferrocenyl]ethyl-di-tert-butylphosphine (2.80 mg, 0.0051 mmol, 0.1 mol %; Josiphos ligand [CAS RN 158923-11-6]; commercially available from Strem Chemicals, USA) and palladium(II) acetate (1.13 mg, 0.0051 mmol, 0.1 mol %). The reaction mixture was stirred at 90° C. for 2 h, concentrated by evaporation under reduced pressure and the residue purified by silica column chromatography using a MPLC system (CombiFlash Companion, Isco Inc.) eluting with a gradient of heptane (+1% triethylamine)/ethyl acetate providing 0.22 g (12%) of the title compound. $^1$H NMR (300 MHz, DMSO): δ 1.27-1.41 (m, 2H), 1.42 (s, 9H), 1.93-1.97 (m, 2H), 2.95-3.03 (m, 2H), 3.86-3.90 (m, 2H), 4.09-4.16 (m, 1H), 6.96 (s, 1H), 7.14 (d, J=7.7 Hz, 1H), 7.24-7.30 (m, 1H), 7.55-7.57 (m, 2H), 7.86 (d, J=7.7 Hz, 1H), MS (ISP): 362.4 [M+H]+.

Step 2: (4-Chloro-quinolin-2-yl)-piperidin-4-yl-amine dihydrochloride

A solution of 4-(4-chloro-quinolin-2-ylamino)-piperidine-1-carboxylic acid tert-butyl ester (0.22 g, 0.61 mmol) in 4 M HCl in dioxane (30 mL) was stirred at rt for 1 h. The solvent was removed under reduced pressure and the crude product used in the consecutive step without further purification

Intermediate B11

(8-Chloro-quinolin-2-yl)-piperidin-4-yl-amine dihydrochloride

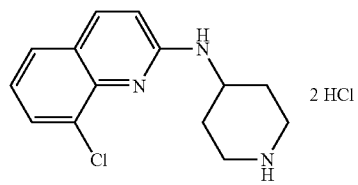

Step 1: 4-(8-Chloro-quinolin-2-ylamino)-piperidine-1-carboxylic acid tert-butyl ester To a degassed solution of 2,8-dichloro-quinoline (3.00 g, 15.15 mmol, 1.0 equiv; commercially available) and 4-amino-piperidine-1-carboxylic acid tert-butyl ester (3.64 g, 18.18 mmol, 1.2 equiv; commercially available) in toluene (35 mL) was added KOtert-Bu (2.38 g, 21.21 mmol, 1.4 equiv), rac-2,2'-bis(diphenylphosphino)-1,1'-binaphthalene (0.38 g, 0.61 mmol, 0.04 equiv) and tris(dibenzylideneacetone)-dipalladium(0) (0.31 g, 0.30 mmol, 0.02 equiv). The reaction mixture was stirred at 80° C. for 18 h, concentrated by evaporation under reduced pressure and the residue purified by silica column chromatography using a MPLC system (CombiFlash Companion, Isco Inc.) eluting with a gradient of heptane (+1% triethylamine)/ethyl acetate providing 1.73 g (31%) of the title compound. $^1$H NMR (300 MHz, CDCl$_3$): δ 1.37-1.51 (m, 2H), 1.48 (s, 9H), 2.17-2.22 (m, 2H), 2.96-3.04 (m, 2H), 4.07-4.17 (m, 3H), 4.76 (d, J=7.0 Hz, 1H), 6.64 (d, H=8.9 Hz, 1H), 7.11 (t, J=7.8 Hz, 1H), 7.49 (d, J=7.8 Hz, 1H), 7.64 (d, J=7.8 Hz, 1H), 7.80 (d, J=8.9 Hz, 1H). MS (ISP): 362.5 [M+H]$^+$.

Step 2: (8-Chloro-quinolin-2-yl)-piperidin-4-yl-amine dihydrochloride

A solution of 4-(8-chloro-quinolin-2-ylamino)-piperidine-1-carboxylic acid tert-butyl ester (1.30 g, 3.59 mmol) in 4 M HCl in dioxane (120 mL) was stirred at rt for 1 h. The solvent was removed under reduced pressure and the crude product used in the consecutive step without further purification assuming quantitative deprotection and formation of the dihydrochloride salt. MS (ISP): 262.3 [M+H]$^+$.

Intermediate B12

Isoquinolin-1-yl-piperidin-4-yl-amine dihydrochloride

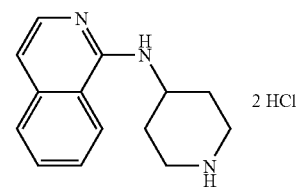

Step 1: 4-(Isoquinolin-1-ylamino)-piperidine-1-carboxylic acid tert-butyl ester To a degassed solution of 1-chloro-isoquinoline (1.00 g, 6.11 mmol, 1.0 equiv; commercially available) and 4-amino-piperidine-1-carboxylic acid tert-butyl ester (1.47 g, 7.34 mmol, 1.2 equiv; commercially available) in dimethoxyethane (15 mL) was added KOtert-Bu (0.96 g, 8.56 mmol, 1.4 equiv), (R)-(-)-1-[(S)-2-(dicyclohexyl-phosphino)-ferrocenyl]ethyl-di-tert-butylphosphine (3.39 mg, 0.0061 mmol, 0.1 mol %; Josiphos ligand [CAS RN 158923-11-6]; commercially available from Strem Chemicals, USA) and palladium (II) acetate (1.37 mg, 0.0061 mmol, 0.1 mol %). The reaction mixture was stirred at 90° C. for 4 h, concentrated by evaporation under reduced pressure and the residue purified by silica column chromatography using a MPLC system (CombiFlash Companion, Isco Inc.) eluting with a gradient of heptane (+1% triethylamine)/ethyl acetate providing 0.83 g (42%) of the title compound. $^1$H NMR (300 MHz, DMSO): δ 1.42-1.54 (m, 2H), 1.43 (s, 9H), 1.92-1.93 (m, 2H), 2.89 (br s, 2H), 3.97-4.03 (m, 2H), 4.29-4.35 (m, 1H), 6.88 (d, J=5.8 Hz, 1H), 7.04 (d, J=7.6 Hz, 1H), 7.47 (t, J=7.0 Hz, 1H), 7.63 (t, J=7.0 Hz, 1H), 7.68 (d, J=7.6 Hz, 1H), 7.86 (d, J=5.8 Hz, 1H), 8.27 (d, J=8.6 Hz, 1H). $^{13}$C NMR (75 MHz, DMSO): δ 28.09, 31.42, 42.99, 47.39, 78.50, 109.41, 117.77, 123.10, 125.29, 126.38, 129.60, 136.67, 141.31, 153.91, 154.49. MS (ISP): 328.5 [M+H]$^{3O}$.

Step 2: Isoquinolin-1-yl-piperidin-4-yl-amine dihydrochloride

A solution of 4-(isoquinolin-1-ylamino)-piperidine-1-carboxylic acid tert-butyl ester (0.83 g, 2.54 mmol) in 4 M HCl in dioxane (100 mL) was stirred at rt for 1 h. The solvent was removed under reduced pressure and the crude product used in the consecutive step without further purification assuming quantitative deprotection and formation of the dihydrochloride salt. MS (ISP): 262.3 [M+H]$^+$.

quantitative deprotection and formation of the dihydrochloride salt. MS (ISP): 228.6 [M+H]+.

Intermediate B13

(3-Chloro-isoquinolin-1-yl)-piperidin-4-yl-amine dihydrochloride

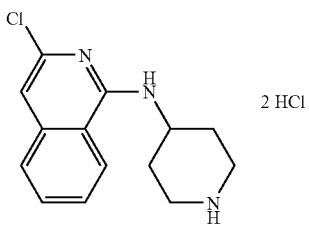

Step 1: 4-(3-Chloro-isoquinolin-1-ylamino)-piperidine-1-carboxylic acid tert-butyl ester To a degassed solution of 1,3-dichloro-isoquinoline (3.00 g, 15.15 mmol, 1.0 equiv; commercially available) and 4-amino-piperidine-1-carboxylic acid tert-butyl ester (3.64 g, 18.18 mmol, 1.2 equiv; commercially available) in toluene (35 mL) was added KOtert-Bu (2.38 g, 21.21 mmol, 1.4 equiv), rac-2,2'-bis(diphenylphosphino)-1,1'-binaphthalene (0.38 g, 0.61 mmol, 0.04 equiv) and tris(dibenzylideneacetone)-dipalladium(0) (0.31 g, 0.30 mmol, 0.02 equiv). The reaction mixture was stirred at 80° C. for 18 h, concentrated by evaporation under reduced pressure and the residue purified by silica column chromatography using a MPLC system (CombiFlash Companion, Isco Inc.) eluting with a gradient of heptane (+1% triethylamine)/ethyl acetate providing 1.14 g (21%) of the title compound. 1H NMR (300 MHz, DMSO): δ 1.41-1.48 (m, 2H), 1.43 (s, 9H), 1.90-1.91 (m, 2H), 2.87-2.93 (m, 2H), 3.97-4.02 (m, 2H), 4.24-4.27 (m, 1H), 6.96 (s, 1H), 7.45-7.48 (m, 2H), 7.64-7.66 (m, 2H), 8.29 (d, J=8.4 Hz, 1H). MS (ISN): 360.0 [M−H]−.

Step 2: (3-Chloro-isoquinolin-1-yl)-piperidin-4-yl-amine dihydrochloride

A solution of 4-(3-chloro-isoquinolin-1-ylamino)-piperidine-1-carboxylic acid tert-butyl ester (1.14 g, 3.15 mmol) in 4 M HCl in dioxane (100 mL) was stirred at rt for 1 h. The solvent was removed under reduced pressure and the crude product used in the consecutive step without further purification assuming quantitative deprotection and formation of the dihydrochloride salt. MS (ISP): 262.3 [M+H]+.

Intermediate B14

5-(Piperidin-4-ylamino)-pyrazine-2-carboxylic acid methyl ester dihydrochloride

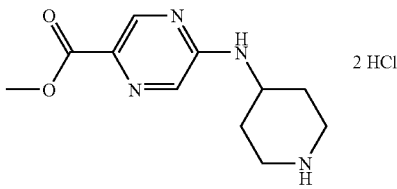

Step 1: 4-(Isoquinolin-1-ylamino)-piperidine-1-carboxylic acid tert-butyl ester A solution of 5-chloro-pyrazine-2-carboxylic acid methyl ester (1.33 g, 7.68 mmol, 1.0 equiv; commercially available) and 4-amino-piperidine-1-carboxylic acid tert-butyl ester (2.00 g, 10.00 mmol, 1.3 equiv; commercially available) in N-ethyl diisopropylamine (12 mL) and acetonitrile (16 mL) was heated by microwave irradiation to 160° C. for 40 min. The solvent was evaporated under reduced pressure and the residue purified by silica column chromatography using a MPLC system (CombiFlash Companion, Isco Inc.) eluting with a gradient of heptane/ethyl acetate providing 1.62 g (63%) of the title compound. 1H NMR (300 MHz, DMSO): δ 1.27-1.41 (m, 2H), 1.41 (s, 9H), 1.86-1.90 (m, 2H), 2.88-2.97 (m, 2H), 3.79 (s, 3H), 3.85-3.91 (m, 2H), 3.96-4.03 (m, 1H), 7.93 (d, J=8.0 Hz, 1H), 7.95 (s, 1H), 8.58 (s, 1H). MS (ISP): 337.5 [M+H]+.

Step 2: 5-(Piperidin-4-ylamino)-pyrazine-2-carboxylic acid methyl ester dihydrochloride A solution of 4-(isoquinolin-1-ylamino)-piperidine-1-carboxylic acid tert-butyl ester (1.62 g, 4.82 mmol) in 4 M HCl in dioxane (100 mL) was stirred at rt for 1 h. The solvent was removed under reduced pressure and the crude product used in the consecutive step without further purification assuming quantitative deprotection and formation of the dihydrochloride salt. MS (ISP): 237.1 [M+H]+.

The aldehyde intermediates E1 to E21 were prepared following literature precedents or in analogy to literature precedents or as described below.

Synthesis of Aldehyde Intermediates E1 to E21 to be used in Table 4

Intermediate E1

3-Ethoxy-4-fluoro-benzaldehyde

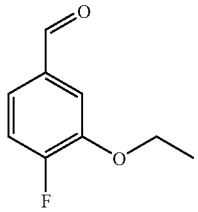

The title compound was prepared according to the procedure described for the synthesis of 4-chloro-3-ethoxy-benzaldehyde (intermediate E2, vide infra) starting from 4-fluoro-3-hydroxy-benzoic acid in 73% overall yield after purification by flash column chromatography on silica eluting with hexane/ethyl acetate (10:1). $^1$H NMR (300 MHz, DMSO): δ 1.32 (t, J=7.0 Hz, 3H), 4.12 (q, J=7.0 Hz, 2H), 7.34-7.41 (m, 1H), 7.47-7.56 (m, 2H), 9.87 (s, 1H). MS (ISP): 186.1 [M+NH$_4$]$^+$.

Intermediate E2

4-Chloro-3-ethoxy-benzaldehyde [CAS RN 85259-46-7]

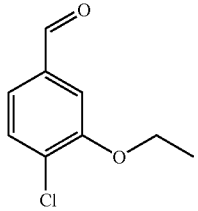

To a solution of 4-chloro-3-hydroxy-benzoic acid (3.0 g, 17.4 mmol, 1.0 equiv) in DMF (15 mL) was added K$_2$CO$_3$ (4.81 g, 34.8 mmol, 2.0 equiv) and ethyl iodide (4.03 mL, 5.97 g, 38.2 mmol, 2.2 equiv). The reaction mixture was stirred for 6 h at rt, diluted with water (20 mL) and extracted with ethyl acetate (3×50 mL). The organic phases were dried over Na$_2$SO$_4$ and concentrated to afford 3.6 g (91%) of 4-chloro-3-ethoxy-benzoic acid ethyl ester. The crude ester was then dissolved in THF (20 mL) and cooled to −78° C. under Ar. A solution of diisobutylaluminium hydride (95 mL, 95.0 mmol, 6.0 equiv; 1.0 M solution in THF) was slowly added over a time period of 15 min, the cooling bath removed on completion of addition and the reaction allowed to reach 0° C. After stirring for 1 h, the reaction was cooled to −78° C. and the excess hydride quenched by cautious addition of a solution of 1 M HCl (10 mL). The mixture was brought to rt, the organic phase separated and the aqueous layer extracted with ethyl acetate (3×100 mL). The combined organic phases were dried over Na$_2$SO$_4$ and concentrated by evaporation under reduced pressure providing 2.94 g (100%) of 4-chloro-3-ethoxy-benzyl alcohol. The crude alcohol (2.94 g, 15.75 mmol, 1.0 equiv) was dissolved in dichloromethane (15 mL) and activated MnO$_2$ (5.48 g, 63.0 mmol, 4.0 equiv) was added. The reaction mixture was stirred for 16 h, after which time the reaction was filtered through Hyflo Super Cel and concentrated. The residue was purified by flash column chromatography on silica eluting with heptane/ethyl acetate (4:1) to yield 1.51 g (52%) of the title compound. $^1$H NMR (300 MHz, CDCl$_3$): δ 1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

Intermediate E3

3,5-Diethoxy-benzaldehyde [CAS RN 120355-79-5]

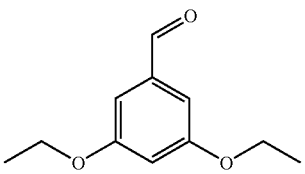

The title compound was prepared analogously to 3-ethoxy-4-methyl-benzaldehyde (intermediate E10, vide infra) by reaction of 3,5-dihydroxybenzaldehyde with ethyl iodide in DMF using K$_2$CO$_3$ as base.

Intermediate E4

3,5-Diisopropoxy-benzaldehyde [CAS RN 94169-64-9]

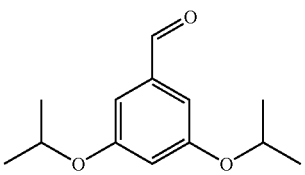

To a solution of 3,5-dihydroxy-benzaldehyde (5.0 g, 36.20 mmol, 1.0 equiv) in anhydrous DMF (30 mL) was added K$_2$CO$_3$ (15.0 g, 108.60 mmol, 3.0 equiv) and 2-bromo-propane (13.36 g, 10.20 mL, 108.60 mmol, 3.0 equiv) and the mixture stirred at 100° C. for 18 h. The K$_2$CO$_3$ was removed by filtration and the organic phase concentrated under reduced pressure. To the residue was added a sat. solution of NaCl (100 mL) and the solution extracted with ethyl acetate (3×100 mL). The combined organic phases were dried over MgSO$_4$ and the product purified by silica column chromatography using a MPLC system (CombiFlash Companion, Isco Inc.) eluting with a gradient of heptane/ethyl acetate affording 6.64 g (83%) of the title compound and 0.59 g (9%) of 3-hydroxy-5-isopropoxy-benzaldehyde (intermediate E19, vide infra). $^1$H NMR (300 MHz, CDCl$_3$): δ 1.35 (d, J=6.1 Hz, 12H), 4.59 (hept, J=6.1 Hz, 2H), 6.66-6.68 (m, 1H), 6.96-6.97 (m, 2H), 9.88 (s, 1H). MS (ISP): 223.1 [M+H]+.

Intermediate E5

3,5-Diethoxy-4-fluoro-benzaldehyde

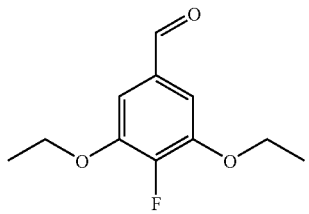

Step 1:
tert-Butyl-(4-fluoro-benzyloxy)-dimethyl-silane

To a solution of (4-fluoro-phenyl)-methanol (12.16 g, 96.4 mmol, 1.0 equiv) in anhydrous DMF (50 mL) at 0° C. under Ar was added imidazole (7.22 g, 106.1 mmol, 1.1 equiv) and tert-butyl-chloro-dimethyl-silane (15.99 g, 106.1 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of Na$_2$CO$_3$ (2×100 mL) and NaCl (2×100 mL). The organic phase was dried over Na$_2$SO$_4$, concentrated by evaporation under reduced pressure yielding a brown oil that was purified by high vacuum destillation (bp 32-35° C. at 0.1 mbar) to give 23.0 g (99%) of the title compound. $^1$H NMR (400 MHz, CDCl$_3$): δ 0.00 (s, 6H), 0.84 (s, 9H), 4.60 (s, 2H), 6.89-6.94 (m, 2H), 7.16-7.20 (m, 2H). MS (EI): 183.1 [M-tert-Bu]+.

Step 2: 5-(tert-Butyl-dimethyl-silanyloxymethyl)-2-fluoro-phenol

To a solution of tert-butyl-(4-fluoro-benzyloxy)-dimethyl-silane (5.00 g, 20.8 mmol, 1.0 equiv) in anhydrous THF (20 mL) was added at −78° C. under Ar a solution of sec-BuLi (17.6 mL, 22.8 mmol, 1.1 equiv; 1.3 M solution in hexane) within 30 min. Then a solution of trimethyl borate (2.37 mL, 2.20 g, 20.8 mmol, 1.0 equiv) in anhydrous THF (7.5 mL) was added slowly within 30 min and the cooling bath removed. A solution of conc. acetic acid (2.78 mL, 1.87 g, 31.2 mmol, 1.5 equiv) was slowly added followed by addition of a solution of 35% hydrogen peroxide in water (2.0 mL, 2.23 g, 22.9 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of NaCl (2×100 mL). The organic phase was dried over Na$_2$SO$_4$, concentrated by evaporation under reduced pressure and the crude material purified with column chromatography on silica eluting with hexane/ethyl acetate (19:1) providing 4.80 g (90%) of the title compound. $^1$H NMR (400 MHz, CDCl$_3$): δ 0.00 (s, 6H), 0.84 (s, 9H), 4.56 (s, 2H), 4.97 (br s, 1H), 6.68-6.72 (m, 1H), 6.87-6.94 (m, 2H). MS (EI): 256.2 [M]+.

Step 3: 2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 equiv) in anhydrous DMF (20 mL) at 0° C. under Ar was added imidazole (1.34 g, 19.7 mmol, 1.1 equiv) and tert-butyl-chloro-dimethyl-silane (2.97 g, 19.7 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of Na$_2$CO$_3$ (2×100 mL) and NaCl (2×100 mL). The organic phase was dried over Na$_2$SO$_4$ and concentrated by evaporation under reduced pressure yielding 4.50 g (68%) of the title compound. $^1$H NMR (400 MHz, CDCl$_3$): δ 0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS (EI): 370.2 [M]+.

Step 4: 3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol, 1.0 equiv) in anhydrous THF (130 mL) was added at −78° C. under Ar a solution of sec-BuLi (54.5 mL, 71.6 mmol, 1.1 equiv; 1.3 M solution in hexane) within 30 min. Then a solution of trimethyl borate (7.13 mL, 6.64 g, 63.9 mmol, 1.0 equiv) in anhydrous THF (30 mL) was added slowly within 30 min and the cooling bath removed. A solution of conc. acetic acid (5.49 mL, 5.76 g, 95.9 mmol, 1.5 equiv) was slowly added followed by addition of a solution of 35% hydrogen peroxide in water (6.2 mL, 6.83 g, 70.3 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of NaCl (2×100 mL). The organic phase was dried over Na$_2$SO$_4$, concentrated by evaporation under reduced pressure and the crude material purified with column chromatography on silica eluting with hexane/ethyl acetate (19:1) providing 15.80 g (64%) of the title compound. $^1$H NMR (400 MHz, CDCl$_3$): δ 0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d j=5.6 Hz, 1H). MS (EI): 329.2 [M-tert-Bu]+.

Step 5: tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 equiv) in DMF (60 mL) was added K$_2$CO$_3$ (4.56 g, 33.0 mmol, 2.2 equiv) and ethyl bromide (2.46 mL, 3.60 g, 33.0 mmol, 2.2 equiv) and the reaction mixture stirred under Ar at 60° C. for 5 h. The K$_2$CO$_3$ was removed by filtration, the crude reaction mixture concentrated by evaporation under reduced pressure, the residue extracted with ethyl acetate (3×100 mL), the combined organic phases washed with water (2×100 ml) and dried over Na$_2$SO$_4$. The solvent was removed by evaporation under reduced pressure and the crude material purified with column chromatography on silica eluting with hexane/ethyl acetate (99:1) providing 3.10 g (63%) of the title compound. $^1$H NMR (400 MHz, CDCl$_3$): δ 0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS (ISP): 329.3 [M+H]+.

Step 6: (3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 equiv) in methanol (8 mL) was added Dowex 50W-X8 (0.33 g, cation exchange resin) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, CDCl$_3$): δ 1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS (EI): 214.2 [M]$^+$.

Step 7: 3,5-Diethoxy-4-fluoro-benzaldehyde

To a solution of (3,5-diethoxy-4-fluoro-phenyl)-methanol (2.30 g, 10.7 mmol, 1.0 equiv) in 1,2-dichloroethane (50 mL) was added activated MnO$_2$ (2.89 g, 33.3 mmol, 3.1 equiv). The reaction mixture was stirred for 21 h at 50° C. and then filtered through Hyflo Super Cel providing after evaporation of the solvent under reduced pressure 1.90 g (83%) of the title compound. $^1$H NMR (400 MHz, CDCl$_3$): δ 1.38 (t, J=7.0 Hz, 6H), 4.09 (q, J=7.0 Hz, 4H), 7.04 (d, J=7.2 Hz, 2H), 9.75 (s, 1H). MS (EI): 212.1 [M]$^+$.

Intermediate E6

4-Chloro-3,5-diethoxy-benzaldehyde

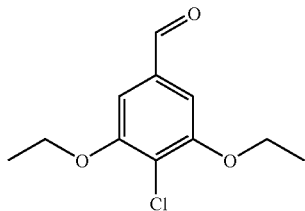

Step 1: 4-Chloro-3,5-diethoxy-benzoic acid ethyl ester

To a solution of 4-amino-3,5-diethoxy-benzoic acid ethyl ester (5.1 g, 20.13 mmol, 1.0 equiv; prepared as described in I. Kompis and A. Wick *Helv. Chim. Acta* 1977, 60, 3025-3034) in water (40 mL) and 37% HCl (40 mL) at 0° C. was added sodium nitrite (1.67 g, 24.16 mmol, 1.2 equiv). After 10 min, copper(I) chloride (12.0 g, 120.81 mmol, 6.0 equiv) was added, the reaction mixture stirred for an additional 5 h at 0° C. and then the ice bath removed. After stirring for 18 h, the crude reaction mixture was adjusted to pH=8 by addition of a solution of 1 M NaOH and the aqueous layer extraced with ethyl acetate (3×100 mL). The combined organic phases were dried over MgSO$_4$, concentrated by evaporation under reduced pressure and the crude material purified by silica column chromatography using a MPLC system (CombiFlash Companion, Isco Inc.) eluting with a gradient of heptane/ethyl acetate providing 5.0 g (91%) of the title compound. $^1$H NMR (300 MHz, CDCl$_3$): δ 1.32 (t, J=7.0 Hz, 4H), 1.40 (t, J=7.0 Hz, 6H), 4.09 (q, J=7.0 Hz, 4H), 4.30 (q, J=7.0 Hz, 2H), 7.18 (s, 2H). $^{13}$C NMR (75 MHz, CDCl$_3$): δ 13.33, 13.66, 60.29, 64.16, 105.75, 115.88, 128.25, 154.49, 165.01. MS (ISP): 273.3 [M+H]$^+$.

Step 2: (4-Chloro-3,5-diethoxy-phenyl)-methanol

To a solution of 4-chloro-3,5-diethoxy-benzoic acid ethyl ester (5.0 g, 18.33 mmol, 1.0 equiv) in dichloromethane (25 mL) was added slowly over a time period of 15 min under slight cooling to −30° C. a solution of diisobutylaluminum hydride (55.0 mL, 55.00 mmol, 3.0 equiv; 1.0 M solution in THF). After 30 min, the excess hydride was quenched by cautious addition of methanol (10 mL) and water (2 mL). The mixture was stirred for 30 min, a solution of 1 M HCl was added and the aqueous layer extracted with ethyl acetate (3×100 mL). The combined organic phases were dried over MgSO$_4$ and concentrated by evaporation under reduced pressure providing 4.0 g (95%) of the title compound. $^1$H NMR (300 MHz, CDCl$_3$): δ 1.45 (t, J=7.0 Hz, 6H), 1.93 (br s, 1H), 4.09 (q, J=7.0 Hz, 4H), 4.62 (s, 2H), 6.57 (s, 2H). $^{13}$C NMR (75 MHz, CDCl$_3$): δ 14.74, 64.96, 65.18, 104.30, 110.65, 140.29, 155.66. MS (ISP): 231.4 [M+H]$^+$.

Step 3: 4-Chloro-3,5-diethoxy-benzaldehyde

To a solution of (4-chloro-3,5-diethoxy-phenyl)-methanol (4.0 g, 17.34 mmol, 1.0 equiv) in THF (40 mL) was added activated MnO$_2$ (15.08 g, 173.4 mmol, 10.0 equiv) and the reaction mixture stirred for 18 h at rt. Filtration through Hyflo Super Cel and purification of the crude material by silica column chromatography using a MPLC system (CombiFlash Companion, Isco Inc.) eluting with a gradient of heptane/ethyl acetate provided 3.7 g (92%) of the title compound. $^1$H NMR (300 MHz, CDCl$_3$): δ 1.50 (t, J=7.0 Hz, 6H), 4.19 (q, J=7.0 Hz, 4H), 7.07 (s, 2H), 9.89 (s, 1H). $^{13}$C NMR (75 MHz, CDCl$_3$): δ 14.61, 65.22, 106.26, 118.64, 135.08, 156.22, 191.01. MS (EI): 229.4 [M]$^+$.

Intermediate E7

4-Bromo-3,5-diethoxy-benzaldehyde [CAS RN 363166-11-4]

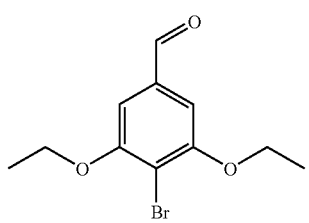

The title compound was prepared from 4-bromo-3,5-dihydroxy-benzoic acid as described in S. P. Dudek, H. D. Sikes and C. E. D. Chidsey *J. Am. Chem. Soc.* 2001, 123, 8033-8038.

Intermediate E8

4-Amino-3,5-diethoxy-benzaldehyde

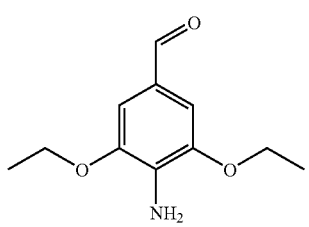

Step 1: (4-Amino-3,5-diethoxy-phenyl)-methanol

To a solution of 4-amino-3,5-diethoxy-benzoic acid ethyl ester (2.8 g, 11.05 mmol, 1.0 equiv; prepared as described in I. Kompis, A. Wick *Helv. Chim. Acta* 1977, 60, 3025-3034) in dichloromethane (50 mL) at 0° C. under Ar was slowly added diisobutylaluminium hydride (27.6 mL, 27.64 mmol, 2.5 equiv; 1.0 M solution in dichloromethane) over a time period of 15 min and the cooling bath removed on completion of addition. After stirring for 18 h, the excess hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over MgSO$_4$, concentrated by evaporation under reduced pressure and the crude material purified by column chromatography on silica eluting with a gradient of heptane/ethyl acetate (4:1→1:1) providing 1.10 g (47%) of the title compound. $^1$H NMR (300 MHz, CDCl$_3$): δ 1.42 (t, J=7.0 Hz, 3H), 3.82 (br s, 2H), 4.05 (q, J=7.0 Hz, 2H), 4.54 (s, 2H), 6.50 (s, 2H). $^{13}$C NMR (75 MHz, CDCl$_3$): δ 15.03, 64.21, 66.00, 104.51, 125.44, 129.89, 146.71. MS (ISP): 211.9 [M+H]$^+$.

Step 2: 4-Amino-3,5-diethoxy-benzaldehyde

To a solution of (4-amino-3,5-diethoxy-phenyl)-methanol (0.79 g, 3.74 mmol, 1.0 equiv) in DMF (20 mL) was added activated MnO$_2$ (1.63 g, 18.70 mmol, 5.0 equiv). The reaction mixture was stirred for 24 h at rt, filtered through Hyflo Super Cel, the filtrate extracted with ethyl acetate (3×50 mL) and the combined organic phases dried over MgSO$_4$ providing 0.69 g (88%) of the title compound. $^1$H NMR (300 MHz, DMSO): δ 1.46 (t, J=7.0 Hz, 3H), 4.15 (q, J=7.0 Hz, 2H), 4.50 (br s, 2H), 7.04 (s, 2H), 9.70 (s, 1H). MS (ISP): 210.0 [M+H]$^+$.

Intermediate E9

3,5-Diethoxy-4-pyrrol-1-yl-benzaldehyde

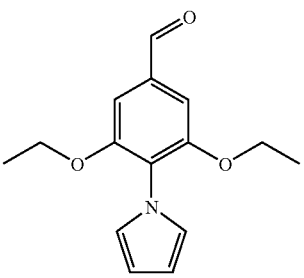

Step 1: 3,5-Diethoxy-4-pyrrol-1-yl-benzoic acid ethyl ester

To a solution of 4-amino-3,5-diethoxy-benzoic acid ethyl ester (3.0 g, 11.84 mmol, 1.0 equiv; prepared as described in I. Kompis and A. Wick *Helv. Chim. Acta* 1977, 60, 3025-3034) in heptane (10 mL) and conc. acetic acid (0.2 mL) was added 2,5-dimethoxy-tetrahydro-furan (1.88 g, 14.21 mmol, 1.2 equiv). After heating to reflux for 5 h, a Dean-Stark apparatus was attached and the reaction mixture heated for an additional time period of 5 h. Filtration of the crude reaction mixture and crystallization at 0° C. from heptane provided 2.94 g (82%) of the title compound. $^1$H NMR (300 MHz, DMSO): δ 1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H). $^{13}$C NMR (75 MHz, DMSO): δ 14.11, 14.35, 61.06, 64.57, 106.87, 107.64, 122.61, 123.33, 129.29, 153.75, 165.06. MS (ISP): 303.4 [M+H]$^+$.

Step 2: 3,5-Diethoxy-4-pyrrol-1-yl-benzaldehyde

To a solution of 3,5-diethoxy-4-pyrrol-1-yl-benzoic acid ethyl ester (1.51 g, 4.98 mmol, 1.0 equiv) in toluene (5 mL) was added slowly over a time period of 15 min under slight cooling to 20° C. a solution of diisobutylaluminium hydride (8.9 mL, 12.45 mmol, 2.5 equiv; 20% solution in toluene). After 1 h the excess hydride was quenched by cautious addition of water (10 mL) and a 28% solution of NaOH (2 mL). The mixture was stirred for 30 min and the organic phase filtered over Hyflo Super Cel. The aqueous layer was extracted with toluene (2×50 mL), the combined organic phases washed with a sat. solution of NaCl (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL) and activated MnO$_2$ (7.79 g, 89.5 mmol, 18.0 equiv) was added. The reaction mixture was heated to reflux for 7 h, after which time the reaction mixture was filtered through Hyflo Super Cel and concentrated yielding 1.15 g (89% yield) of the title compound. $^1$H NMR (300 MHz, DMSO): δ 1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H). MS (ISP): 260.1 [M+H]+.

Intermediate E10

3-Ethoxy-4-methyl-benzaldehyde [CAS RN 157143-20-9]

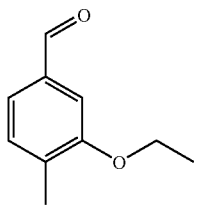

The title compound was prepared by reaction of commercially available 3-hydroxy-4-methyl-benzaldehyde with ethyl iodide in DMF using $K_2CO_3$ as base in analogy to the procedure described in M. J. Ashton, D. C. Cook, G. Fenton, J.-A. Karlsson, M. N. Palfreyman, D. Raeburn, A. J. Ratcliffe, J. E. Souness, S. Thurairatnam and N. Vicker *J. Med. Chem.* 1994, 37, 1696-1703.

Intermediate E11

4-Methoxy-3-propoxy-benzaldehyde [CAS RN 5922-56-5]

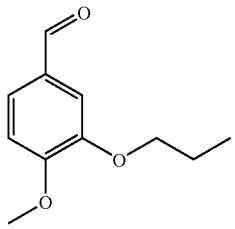

The title compound was prepared by reaction of isovanillin with propyl iodide in DMF using $K_2CO_3$ as base in analogy to the preparation of 3-ethoxy-4-methyl-benzaldehyde (intermediate E10).

Intermediate E12

3-Isobutoxy-4-methoxy-benzaldehyde [CAS RN 57724-26-2]

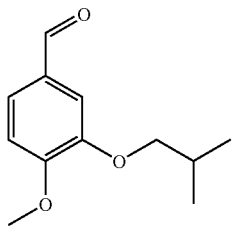

The title compound was prepared by reaction of isovanillin with 1-bromo-2-methyl propane as described in WO 04/000 806 A1 (Elbion AG).

Intermediate E13

3,5-Diethoxy-4-iodo-benzaldehyde [CAS RN 338454-05-0]

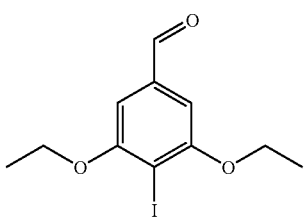

The title compound was prepared as described in WO 01/326 33 A1 (F. Hoffmann-La Roche AG).

Intermediate E14

3-Ethoxy-4-iodo-5-methoxymethoxy-benzaldehyde [CAS RN 338451-02-8]

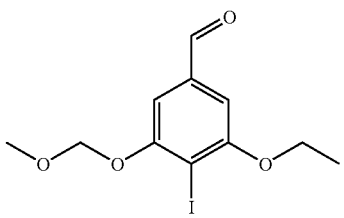

The title compound was prepared as described in WO 01/032 633 A1 (F. Hoffmann-La Roche AG).

Intermediate E15

3-Ethoxy-4-(1-ethyl-propoxy)-benzaldehyde

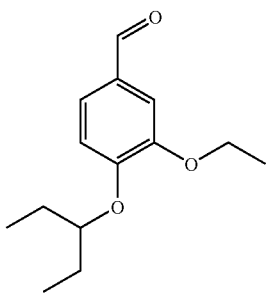

The title compound was prepared analogously to 3-ethoxy-4-methyl-benzaldehyde (intermediate E10) by reaction of 3-ethoxy-4-hydroxy-benzaldehyde with 3-bromo-pentane in DMF using $K_2CO_3$ as base. MS (ISP): 237.1 $[M+H]^+$.

Intermediate E16

3-Allyloxy-4-methoxy-benzaldehyde [CAS RN 225939-36-6]

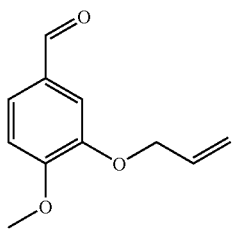

The title compound was prepared analogously to 3-ethoxy-4-methyl-benzaldehyde (intermediate E10) by reaction of 3-hydroxy-4-methoxy-benzaldehyde with allylbromide in DMF using $K_2CO_3$ as base (see also A. W. White, R. Almassy, A. H. Calvert, N. J. Curtin, R. J. Griffin, Z. Hostomsky, K. Maegley, D. R. Newell, S. Srinivasan and B. T. Golding *J. Med. Chem.* 2000, 43, 4084-4097).

Intermediate E17

3-Butoxy-4-methoxy-benzaldehyde

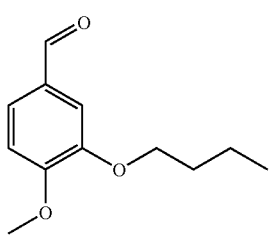

The title compound was prepared analogously to 3-ethoxy-4-methyl-benzaldehyde (intermediate E10) by reaction of 3-hydroxy-4-methoxy-benzaldehyde with 4-bromo-butane in DMF using $K_2CO_3$ as base. MS (ISP): 209.1 $[M+H]^+$.

Intermediate E18

8-Ethoxy-2,2-dimethyl-2H-chromene-6-carbaldehyde [CAS RN 210404-30-9]

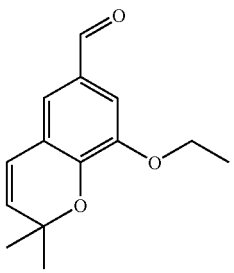

The title compound was prepared according to WO 01/083 476 A1 (Hoffmann-La Roche AG).

Intermediate E19

3-Hydroxy-5-isopropoxy-benzaldehyde

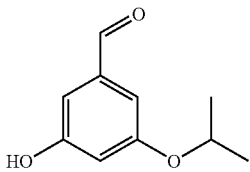

Isolated as a side-product in the synthesis of 3,5-diisopropoxy-benzaldehyde (intermediate E4). $^1$H NMR (300 MHz, $CDCl_3$): δ 1.34 (d, J=6.1 Hz, 6H), 4.58 (hept, J=6.1 Hz, 1H), 6.28 (br s, 1H), 6.68-6.69 (m, 1H), 6.95-6.98 (m, 2H), 9.85 (s, 1H). MS (ISN): 179.1 $[M-H]^-$.

Intermediate E20

2,6-Diethoxy-4-formyl-benzoic acid ethyl ester [CAS RN 55687-55-3]

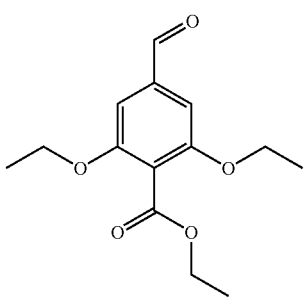

The title compound was prepared as described in DE 243 59 34 (F. Hoffmann-La Roche AG).

Intermediate E21

3-(2-Fluoro-ethoxy)-4-methoxy-benzaldehyde

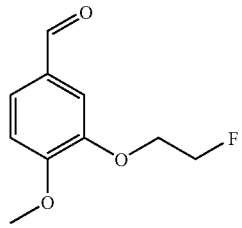

To a solution of 3-hydroxy-4-methoxy-benzaldehyde (10.0 g, 66.0 mmol, 1.0 equiv; commercially available) in anhydrous DMF (40 mL) was added $K_2CO_3$ (13.6 g, 99.0 mmol, 1.5 equiv) and 1-bromo-2-fluoro-ethane (9.2 mg, 72.0 mmol, 1.1 equiv) and the mixture stirred at rt for 48 h. The $K_2CO_3$ was removed by filtration and the organic phase concentrated under reduced pressure. To the residue was added a sat. solution of NaCl (100 mL) and the solution extracted with ethyl acetate (3×100 mL). The combined organic phases were dried over $MgSO_4$ and the product crystallized from a mixture of isopropanol/diethylether to yield 12.69 g (97%) of the title compound. $^1$H NMR (300 MHz, DMSO): δ 3.89 (s, 3H), 4.24-4.27 (m, 1H), 4.34-4.37 (m, 1H), 4.67-4.70 (m, 1H), 4.83-4.86 (m, 1H), 7.20 (d, J=8.4 Hz, 1H), 7.43 (d, J=1.9 Hz, 1H), 7.59 (dd, J=8.4 Hz, J=1.9 Hz, 1H), 9.84 (s, 1H). MS (ISP): 198.6 [M+H]$^+$.

Examples 39 to 188

According to the procedure described for the synthesis of example 38/step 3 further pyridine, quinoline, isoquinoline and pyrazine derivatives have been synthesized from 6-(piperidin-4-ylamino)-nicotinonitrile dihydrochloride (intermediate B2), 6-(piperidin-4-ylamino)-nicotinamide dihydrochloride (intermediate B3), 6-(piperidin-4-ylamino)-nicotinic acid dihydrochloride (intermediate B4), piperidin-4-yl-[5-(1H-tetrazol-5-yl)-pyridin-2-yl]-amine dihydrochloride (intermediate B5), piperidin-4-yl-(5-trifluoromethyl-pyridin-2-yl)-amine dihydrochloride (intermediate B6), 6-(piperidin-4-ylamino)-4-trifluoromethyl-nicotinic acid methyl ester dihydrochloride (intermediate B7), piperidin-4-yl-quinolin-2-yl-amine dihydrochloride (intermediate B8), (4-methyl-quinolin-2-yl)-piperidin-4-yl-amine dihydrochloride (intermediate B9), (4-chloro-quinolin-2-yl)-piperidin-4-yl-amine dihydrochloride (intermediate B10), (8-chloro-quinolin-2-yl)-piperidin-4-yl-amine dihydrochloride (intermediate B11), isoquinolin-1-yl-piperidin-4-yl-amine dihydrochloride (intermediate B12), (3-chloro-isoquinolin-1-yl)-piperidin-4-yl-amine dihydrochloride (intermediate B13) and 5-(piperidin-4-ylamino)-pyrazine-2-carboxylic acid methyl ester dihydrochloride (intermediate B14) and the respective benzaldehyde intermediate as indicated in Table 4. The results are compiled in Table 4 and comprise example 39 to example 188.

TABLE 4

| No | MW | Compound Name | Starting Materials | ISP [M + H]$^+$ or M − H]$^-$ found |
|---|---|---|---|---|
| 39 | 354.43 | 6-[1-(3-ethoxy-4-fluoro-benzyl)-piperidin-4-ylamino]-nicotinonitrile | 6-(piperidin-4-ylamino)-nicotinonitrile dihydrochloride (intermediate B2) and 3-ethoxy-4-fluoro-benzaldehyde (intermediate E1) | [M + H]$^+$ 355.4 |
| 40 | 370.88 | 6-[1-(4-chloro-3-ethoxy-benzyl)-piperidin-4-ylamino]-nicotinonitrile | 6-(piperidin-4-ylamino)-nicotinonitrile dihydrochloride (intermediate B2) and 4-chloro-3-ethoxy-benzaldehyde (intermediate E2) | [M + H]$^+$ 371.2 |
| 41 | 352.44 | 6-[1-(3-ethoxy-4-hydroxy-benzyl)-piperidin-4-ylamino]-nicotinonitrile | 6-(piperidin-4-ylamino)-nicotinonitrile dihydrochloride (intermediate B2) and 3-ethoxy-4-hydroxy-benzaldehyde (commercially available) | [M + H]$^+$ 352.6 |
| 42 | 380.49 | 6-[1-(3,5-diethoxy-benzyl)-piperidin-4-ylamino]-nicotinonitrile | 6-(piperidin-4-ylamino)-nicotinonitrile dihydrochloride (intermediate B2) and 3,5-diethoxy-benzaldehyde (intermediate E3) | [M + H]$^+$ 380.7 |
| 43 | 408.55 | 6-[1-(3,5-diisopropoxy-benzyl)-piperidin-4-ylamino]-nicotinonitrile | 6-(piperidin-4-ylamino)-nicotinonitrile dihydrochloride (intermediate B2) and 3,5-diisopropoxy-benzaldehyde (intermediate E4) | [M + H]$^+$ 409.4 |
| 44 | 398.48 | 6-[1-(3,5-diethoxy-4-fluoro-benzyl)-piperidin-4-ylamino]-nicotinonitrile | 6-(piperidin-4-ylamino)-nicotinonitrile dihydrochloride (intermediate B2) and 3,5-diethoxy-4-fluoro-benzaldehyde (intermediate E5) | [M + H]$^+$ 399.1 |
| 45 | 414.94 | 6-[1-(4-chloro-3,5-diethoxy-benzyl)-piperidin-4-ylamino]- | 6-(piperidin-4-ylamino)-nicotinonitrile dihydrochloride (intermediate B2) and 4-chloro- | [M + H]$^+$ 414.7 |

TABLE 4-continued

| No | MW | Compound Name | Starting Materials | ISP [M + H]+ or M − H]− found |
|---|---|---|---|---|
| | | nicotinonitrile | 3,5-diethoxy-benzaldehyde (intermediate E6) | |
| 46 | 459.39 | 6-[1-(4-bromo-3,5-diethoxy-benzyl)-piperidin-4-ylamino]-nicotinonitrile | 6-(piperidin-4-ylamino)-nicotinonitrile dihydrochloride (intermediate B2) and 4-bromo-3,5-diethoxy-benzaldehyde (intermediate E7) | [M + H]+ 459.2 |
| 47 | 395.51 | 6-[1-(4-amino-3,5-diethoxy-benzyl)-piperidin-4-ylamino]-nicotinonitrile | 6-(piperidin-4-ylamino)-nicotinonitrile dihydrochloride (intermediate B2) and 4-amino-3,5-diethoxy-benzaldehyde (intermediate E8) | [M + H]+ 396.3 |
| 48 | 445.57 | 6-[1-(3,5-diethoxy-4-pyrrol-1-yl-benzyl)-piperidin-4-ylamino]-nicotinonitrile | 6-(piperidin-4-ylamino)-nicotinonitrile dihydrochloride (intermediate B2) and 3,5-diethoxy-4-pyrrol-1-yl-benzaldehyde (intermediate E9) | [M + H]+ 445.8 |
| 49 | 368.48 | 6-[1-(3-ethoxy-4-methyl-benzyl)-piperidin-4-ylamino]-nicotinamide | 6-(piperidin-4-ylamino)-nicotinamide dihydrochloride (intermediate B3) and 3-ethoxy-4-methyl-benzaldehyde (intermediate E10) | [M + H]+ 368.7 |
| 50 | 372.44 | 6-[1-(3-ethoxy-4-fluoro-benzyl)-piperidin-4-ylamino]-nicotinamide | 6-(piperidin-4-ylamino)-nicotinamide dihydrochloride (intermediate B3) and 3-ethoxy-4-fluoro-benzaldehyde (intermediate E1) | [M + H]+ 372.6 |
| 51 | 388.17 | 6-[1-(4-chloro-3-ethoxy-benzyl)-piperidin-4-ylamino]-nicotinamide | 6-(piperidin-4-ylamino)-nicotinamide dihydrochloride (intermediate B3) and 4-chloro-3-ethoxy-benzaldehyde (intermediate E2) | [M + H]+ 389.3 |
| 52 | 370.45 | 6-[1-(3-ethoxy-4-hydroxy-benzyl)-piperidin-4-ylamino]-nicotinamide | 6-(piperidin-4-ylamino)-nicotinamide dihydrochloride (intermediate B3) and 3-ethoxy-4-hydroxy-benzaldehyde (commercially available) | [M + H]+ 370.7 |
| 53 | 384.48 | 6-[1-(3-ethoxy-4-methoxy-benzyl)-piperidin-4-ylamino]-nicotinamide | 6-(piperidin-4-ylamino)-nicotinamide dihydrochloride (intermediate B3) and 3-ethoxy-4-methoxy-benzaldehyde (commercially available) | [M + H]+ 384.6 |
| 54 | 398.51 | 6-[1-(4-methoxy-3-propoxy-benzyl)-piperidin-4-ylamino]-nicotinamide | 6-(piperidin-4-ylamino)-nicotinamide dihydrochloride (intermediate B3) and 4-methoxy-3-propoxy-benzaldehyde (intermediate E11) | [M + H]+ 399.4 |
| 55 | 412.53 | 6-[1-(3-isobutoxy-4-methoxy-benzyl)-piperidin-4-ylamino]-nicotinamide | 6-(piperidin-4-ylamino)-nicotinamide dihydrochloride (intermediate B3) and 3-isobutoxy-4-methoxy-benzaldehyde (intermediate E12) | [M + H]+ 413.4 |
| 56 | 398.51 | 6-[1-(3,5-diethoxy-benzyl)-piperidin-4-ylamino]-nicotinamide | 6-(piperidin-4-ylamino)-nicotinamide dihydrochloride (intermediate B3) and 3,5-diethoxy-benzaldehyde (intermediate E3) | [M + H]+ 398.7 |
| 57 | 426.56 | 6-[1-(3,5-diisopropoxy-benzyl)-piperidin-4-ylamino]-nicotinamide | 6-(piperidin-4-ylamino)-nicotinamide dihydrochloride (intermediate B3) and 3,5-diisopropoxy-benzaldehyde (intermediate E4) | [M + H]+ 426.8 |
| 58 | 416.22 | 6-[1-(3,5-diethoxy-4-fluoro-benzyl)-piperidin-4-ylamino]-nicotinamide | 6-(piperidin-4-ylamino)-nicotinamide dihydrochloride (intermediate B3) and 3,5-diethoxy-4-fluoro-benzaldehyde (intermediate E5) | [M + H]+ 417.3 |
| 59 | 432.95 | 6-[1-(4-chloro-3,5-diethoxy-benzyl)-piperidin-4-ylamino]-nicotinamide | 6-(piperidin-4-ylamino)-nicotinamide dihydrochloride (intermediate B3) and 4-chloro-3,5-diethoxy-benzaldehyde (intermediate E6) | [M + H]+ 432.7 |
| 60 | 413.52 | 6-[1-(4-amino-3,5-diethoxy-benzyl)- | 6-(piperidin-4-ylamino)-nicotinamide dihydrochloride | [M + H]+ 413.7 |

TABLE 4-continued

| No | MW | Compound Name | Starting Materials | ISP [M + H]+ or M − H]− found |
|---|---|---|---|---|
| | | piperidin-4-ylamino]-nicotinamide | (intermediate B3) and 4-amino-3,5-diethoxy-benzaldehyde (intermediate E8) | |
| 61 | 463.58 | 6-[1-(3,5-diethoxy-4-pyrrol-1-yl-benzyl)-piperidin-4-ylamino]-nicotinamide | 6-(piperidin-4-ylamino)-nicotinamide dihydrochloride (intermediate B3) and 3,5-diethoxy-4-pyrrol-1-yl-benzaldehyde (intermediate E9) | [M + H]+ 464.3 |
| 62 | 369.46 | 6-[1-(3-ethoxy-4-methyl-benzyl)-piperidin-4-ylamino]-nicotinic acid | 6-(piperidin-4-ylamino)-nicotinamide dihydrochloride (intermediate B3) and 3-ethoxy-4-methyl-benzaldehyde (intermediate E10) | [M + H]+ 369.7 |
| 63 | 373.43 | 6-[1-(3-ethoxy-4-fluoro-benzyl)-piperidin-4-ylamino]-nicotinic acid | 6-(piperidin-4-ylamino)-nicotinic acid dihydrochloride (intermediate B4) and 3-ethoxy-4-fluoro-benzaldehyde (intermediate E1) | [M + H]+ 373.6 |
| 64 | 389.88 | 6-[1-(4-chloro-3-ethoxy-benzyl)-piperidin-4-ylamino]-nicotinic acid | 6-(piperidin-4-ylamino)-nicotinic acid dihydrochloride (intermediate B4) and 4-chloro-3-ethoxy-benzaldehyde (intermediate E2) | [M + H]+ 389.6 |
| 65 | 371.44 | 6-[1-(3-ethoxy-4-hydroxy-benzyl)-piperidin-4-ylamino]-nicotinic acid | 6-(piperidin-4-ylamino)-nicotinic acid dihydrochloride (intermediate B4) and 3-ethoxy-4-hydroxy-benzaldehyde (commercially available) | [M + H]+ 371.6 |
| 66 | 385.46 | 6-[1-(3-ethoxy-4-methoxy-benzyl)-piperidin-4-ylamino]-nicotinic acid | 6-(piperidin-4-ylamino)-nicotinic acid dihydrochloride (intermediate B4) and 3-ethoxy-4-methoxy-benzaldehyde (commercially available) | [M + H]+ 385.6 |
| 67 | 399.49 | 6-[1-(3,5-diethoxy-benzyl)-piperidin-4-ylamino]-nicotinic acid | 6-(piperidin-4-ylamino)-nicotinic acid dihydrochloride (intermediate B4) and 3,5-diethoxy-benzaldehyde (intermediate E3) | [M + H]+ 399.7 |
| 68 | 427.54 | 6-[1-(3,5-diisopropoxy-benzyl)-piperidin-4-ylamino]-nicotinic acid | 6-(piperidin-4-ylamino)-nicotinic acid dihydrochloride (intermediate B4) and 3,5-diisopropoxy-benzaldehyde (intermediate E4) | [M + H]+ 427.7 |
| 69 | 417.48 | 6-[1-(3,5-diethoxy-4-fluoro-benzyl)-piperidin-4-ylamino]-nicotinic acid | 6-(piperidin-4-ylamino)-nicotinic acid dihydrochloride (intermediate B4) and 3,5-diethoxy-4-fluoro-benzaldehyde (intermediate E5) | [M + H]+ 417.7 |
| 70 | 433.93 | 6-[1-(4-chloro-3,5-diethoxy-benzyl)-piperidin-4-ylamino]-nicotinic acid | 6-(piperidin-4-ylamino)-nicotinic acid dihydrochloride (intermediate B4) and 4-chloro-3,5-diethoxy-benzaldehyde (intermediate E6) | [M + H]+ 433.9 |
| 71 | 413.17 | [1-(4-chloro-3-ethoxy-benzyl)-piperidin-4-yl]-[5-(1H-tetrazol-5-yl)-pyridin-2-yl]-amine | piperidin-4-yl-[5-(1H-tetrazol-5-yl)-pyridin-2-yl]-amine dihydrochloride (intermediate B5) and 4-chloro-3-ethoxy-benzaldehyde (intermediate E2) | [M + H]+ 414.3 |
| 72 | 409.22 | [1-(3-ethoxy-4-methoxy-benzyl)-piperidin-4-yl]-[5-(1H-tetrazol-5-yl)-pyridin-2-yl]-amine | piperidin-4-yl-[5-(1H-tetrazol-5-yl)-pyridin-2-yl]-amine dihydrochloride (intermediate B5) and 3-ethoxy-4-methoxy-benzaldehyde (commercially available) | [M + H]+ 410.4 |
| 73 | 451.27 | [1-(3,5-diisopropoxy-benzyl)-piperidin-4-yl]-[5-(1H-tetrazol-5-yl)-pyridin-2-yl]-amine | piperidin-4-yl-[5-(1H-tetrazol-5-yl)-pyridin-2-yl]-amine dihydrochloride (intermediate B5) and 3,5-diisopropoxy-benzaldehyde (intermediate E4) | [M + H]+ 452.3 |
| 74 | 441.23 | [1-(3,5-diethoxy-4-fluoro-benzyl)-piperidin-4-yl]-[5-(1H-tetrazol-5-yl)-pyridin-2-yl]-amine | piperidin-4-yl-[5-(1H-tetrazol-5-yl)-pyridin-2-yl]-amine dihydrochloride (intermediate B5) and 3,5-diethoxy-4-fluoro-benzaldehyde (intermediate E5) | [M + H]+ 442.4 |

TABLE 4-continued

| No | MW | Compound Name | Starting Materials | ISP [M + H]+ or M − H]− found |
|---|---|---|---|---|
| 75 | 501.15 | [1-(4-bromo-3,5-diethoxy-benzyl)-piperidin-4-yl]-[5-(1H-tetrazol-5-yl)-pyridin-2-yl]-amine | piperidin-4-yl-[5-(1H-tetrazol-5-yl)-pyridin-2-yl]-amine dihydrochloride (intermediate B5) and 4-bromo-3,5-diethoxy-benzaldehyde (intermediate E7) | [M + H]+ 502.5 |
| 76 | 393.45 | [1-(3-ethoxy-4-methyl-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 3-ethoxy-4-methyl-benzaldehyde (intermediate E10) | [M + H]+ 394.3 |
| 77 | 413.87 | [1-(4-chloro-3-ethoxy-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 4-chloro-3-ethoxy-benzaldehyde (intermediate E2) | [M + H]+ 414.3 |
| 78 | 409.45 | [1-(3-ethoxy-4-methoxy-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 3-ethoxy-4-methoxy-benzaldehyde (commercially available) | [M + H]+ 410.3 |
| 79 | 423.48 | [1-(4-methoxy-3-propoxy-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 4-methoxy-3-propoxy-benzaldehyde (intermediate E11) | [M + H]+ 424.3 |
| 80 | 423.48 | [1-(3,5-diethoxy-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 3,5-diethoxy-benzaldehyde (intermediate E3) | [M + H]+ 424.3 |
| 81 | 441.47 | [1-(3,5-diethoxy-4-fluoro-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 3,5-diethoxy-4-fluoro-benzaldehyde (intermediate E5) | [M + H]+ 442.4 |
| 82 | 549.37 | [1-(3,5-diethoxy-4-iodo-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 3,5-diethoxy-4-iodo-benzaldehyde (intermediate E13) | [M + H]+ 550.3 |
| 83 | 565.37 | [1-(3-ethoxy-4-iodo-5-methoxymethoxy-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 3-ethoxy-4-iodo-5-methoxymethoxy-benzaldehyde (intermediate E14) | [M + H]+ 566.2 |
| 84 | 488.55 | [1-(3,5-diethoxy-4-pyrrol-1-yl-benzyl)-piperidin-4-yl]-(5-trifluoromethyl-pyridin-2-yl)-amine | piperidin-4-yl-(5-trifluoromethyl-pyridin-2-yl)-amine dihydrochloride (intermediate B6) and 3,5-diethoxy-4-pyrrol-1-yl-benzaldehyde (intermediate E9) | [M + H]+ 489.4 |
| 85 | 471.91 | 6-[1-(4-chloro-3-ethoxy-benzyl)-piperidin-4-ylamino]-4-trifluoromethyl-nicotinic acid methyl ester | 6-(piperidin-4-ylamino)-4-trifluoromethyl-nicotinic acid methyl ester dihydrochloride (intermediate B7) and 4-chloro-3-ethoxy-benzaldehyde (intermediate E2) | [M + H]+ 472.2 |
| 86 | 453.46 | 6-[1-(3-ethoxy-4-hydroxy-benzyl)-piperidin-4-ylamino]-4-trifluoromethyl-nicotinic acid methyl ester | 6-(piperidin-4-ylamino)-4-trifluoromethyl-nicotinic acid methyl ester dihydrochloride (intermediate B7) and 3-ethoxy-4-hydroxy-benzaldehyde (commercially available) | [M + H]+ 454.2 |
| 87 | 467.49 | 6-[1-(3-ethoxy-4-methoxy-benzyl)-piperidin-4-ylamino]-4-trifluoromethyl-nicotinic acid methyl ester | 6-(piperidin-4-ylamino)-4-trifluoromethyl-nicotinic acid methyl ester dihydrochloride (intermediate B7) and 3-ethoxy-4-methoxy-benzaldehyde (commercially available) | [M + H]+ 468.3 |
| 88 | 481.51 | 6-[1-(4-methoxy-3-propoxy-benzyl)-piperidin-4-ylamino]-4-trifluoromethyl- | 6-(piperidin-4-ylamino)-4-trifluoromethyl-nicotinic acid methyl ester dihydrochloride (intermediate B7) and 4-methoxy- | [M + H]+ 482.3 |

TABLE 4-continued

| No | MW | Compound Name | Starting Materials | ISP [M + H]+ or M − H]− found |
|---|---|---|---|---|
| | | nicotinic acid methyl ester | 3-propoxy-benzaldehyde (intermediate E11) | |
| 89 | 495.54 | 6-[1-(3-isobutoxy-4-methoxy-benzyl)-piperidin-4-ylamino]-4-trifluoromethyl-nicotinic acid methyl ester | 6-(piperidin-4-ylamino)-4-trifluoromethyl-nicotinic acid methyl ester dihydrochloride (intermediate B7) and 3-isobutoxy-4-methoxy-benzaldehyde (intermediate E12) | [M + H]+ 496.3 |
| 90 | 375.52 | [1-(3-ethoxy-4-methyl-benzyl)-piperidin-4-yl]-quinolin-2-yl-amine | piperidin-4-yl-quinolin-2-yl-amine dihydrochloride (intermediate B8) and 3-ethoxy-4-methyl-benzaldehyde (intermediate E10) | [M + H]+ 376.4 |
| 91 | 379.48 | [1-(3-ethoxy-4-fluoro-benzyl)-piperidin-4-yl]-quinolin-2-yl-amine | piperidin-4-yl-quinolin-2-yl-amine dihydrochloride (intermediate B8) and 3-ethoxy-4-fluoro-benzaldehyde (intermediate E1) | [M + H]+ 380.4 |
| 92 | 395.93 | [1-(4-chloro-3-ethoxy-benzyl)-piperidin-4-yl]-quinolin-2-yl-amine | piperidin-4-yl-quinolin-2-yl-amine dihydrochloride (intermediate B8) and 4-chloro-3-ethoxy-benzaldehyde (intermediate E2) | [M + H]+ 396.3 |
| 93 | 391.51 | [1-(3-ethoxy-4-methoxy-benzyl)-piperidin-4-yl]-quinolin-2-yl-amine | piperidin-4-yl-quinolin-2-yl-amine dihydrochloride (intermediate B8) and 3-ethoxy-4-methoxy-benzaldehyde (commercially available) | [M + H]+ 392.2 |
| 94 | 447.62 | {1-[3-ethoxy-4-(1-ethyl-propoxy)-benzyl]-piperidin-4-yl}-quinolin-2-yl-amine | piperidin-4-yl-quinolin-2-yl-amine dihydrochloride (intermediate B8) and 3-ethoxy-4-(1-ethyl-propoxy)-benzaldehyde (intermediate E15) | [M + H]+ 448.2 |
| 95 | 405.54 | [1-(4-methoxy-3-propoxy-benzyl)-piperidin-4-yl]-quinolin-2-yl-amine | piperidin-4-yl-quinolin-2-yl-amine dihydrochloride (intermediate B8) and 4-methoxy-3-propoxy-benzaldehyde (intermediate E11) | [M + H]+ 406.4 |
| 96 | 403.53 | [1-(3-allyloxy-4-methoxy-benzyl)-piperidin-4-yl]-quinolin-2-yl-amine | piperidin-4-yl-quinolin-2-yl-amine dihydrochloride (intermediate B8) and 3-allyloxy-4-methoxy-benzaldehyde (intermediate E16) | [M + H]+ 404.5 |
| 97 | 419.57 | [1-(3-butoxy-4-methoxy-benzyl)-piperidin-4-yl]-quinolin-2-yl-amine | piperidin-4-yl-quinolin-2-yl-amine dihydrochloride (intermediate B8) and 3-butoxy-4-methoxy-benzaldehyde (intermediate E17) | [M + H]+ 420.3 |
| 98 | 419.57 | [1-(3-isobutoxy-4-methoxy-benzyl)-piperidin-4-yl]-quinolin-2-yl-amine | piperidin-4-yl-quinolin-2-yl-amine dihydrochloride (intermediate B8) and 3-isobutoxy-4-methoxy-benzaldehyde (intermediate E12) | [M + H]+ 420.4 |
| 99 | 443.59 | [1-(8-ethoxy-2,2-dimethyl-2H-chromen-6-ylmethyl)-piperidin-4-yl]-quinolin-2-yl-amine | piperidin-4-yl-quinolin-2-yl-amine dihydrochloride (intermediate B8) and 8-ethoxy-2,2-dimethyl-2H-chromene-6-carbaldehyde (intermediate E18) | [M + H]+ 444.4 |
| 100 | 405.54 | [1-(3,5-diethoxy-benzyl)-piperidin-4-yl]-quinolin-2-yl-amine | piperidin-4-yl-quinolin-2-yl-amine dihydrochloride (intermediate B8) and 3,5-diethoxy-benzaldehyde (intermediate E3) | [M + H]+ 406.4 |
| 101 | 391.51 | 3-isopropoxy-5-[4-(quinolin-2-ylamino)-piperidin-1-ylmethyl]-phenol | piperidin-4-yl-quinolin-2-yl-amine dihydrochloride (intermediate B8) and 3-hydroxy-5-isopropoxy-benzaldehyde (intermediate E19) | [M + H]+ 392.2 |
| 102 | 433.60 | [1-(3,5-diisopropoxy-benzyl)-piperidin-4-yl]-quinolin-2-yl-amine | piperidin-4-yl-quinolin-2-yl-amine dihydrochloride (intermediate B8) and 3,5-diisopropoxy-benzaldehyde (intermediate E4) | [M + H]+ 434.4 |

TABLE 4-continued

| No | MW | Compound Name | Starting Materials | ISP [M + H]+ or M − H]− found |
|---|---|---|---|---|
| 103 | 423.53 | [1-(3,5-diethoxy-4-fluoro-benzyl)-piperidin-4-yl]-quinolin-2-yl-amine | piperidin-4-yl-quinolin-2-yl-amine dihydrochloride (intermediate B8) and 3,5-diethoxy-4-fluoro-benzaldehyde (intermediate E5) | [M + H]+ 424.3 |
| 104 | 439.99 | [1-(4-chloro-3,5-diethoxy-benzyl)-piperidin-4-yl]-quinolin-2-yl-amine | piperidin-4-yl-quinolin-2-yl-amine dihydrochloride (intermediate B8) and 4-chloro-3,5-diethoxy-benzaldehyde (intermediate E6) | [M + H]+ 440.4 |
| 105 | 484.44 | [1-(4-bromo-3,5-diethoxy-benzyl)-piperidin-4-yl]-quinolin-2-yl-amine | piperidin-4-yl-quinolin-2-yl-amine dihydrochloride (intermediate B8) and 4-bromo-3,5-diethoxy-benzaldehyde (intermediate E7) | [M + H]+ 484.3 |
| 106 | 420.56 | [1-(4-amino-3,5-diethoxy-benzyl)-piperidin-4-yl]-quinolin-2-yl-amine | piperidin-4-yl-quinolin-2-yl-amine dihydrochloride (intermediate B8) and 4-amino-3,5-diethoxy-benzaldehyde (intermediate E8) | [M + H]+ 421.3 |
| 107 | 470.62 | [1-(3,5-diethoxy-4-pyrrol-1-yl-benzyl)-piperidin-4-yl]-quinolin-2-yl-amine | piperidin-4-yl-quinolin-2-yl-amine dihydrochloride (intermediate B8) and 3,5-diethoxy-4-pyrrol-1-yl-benzaldehyde (intermediate E9) | [M + H]+ 471.4 |
| 108 | 389.54 | [1-(3-ethoxy-4-methyl-benzyl)-piperidin-4-yl]-(4-methyl-quinolin-2-yl)-amine | (4-methyl-quinolin-2-yl)-piperidin-4-yl-amine dihydrochloride (intermediate B9) and 3-ethoxy-4-methyl-benzaldehyde (intermediate E10) | [M + H]+ 390.4 |
| 109 | 393.51 | [1-(3-ethoxy-4-fluoro-benzyl)-piperidin-4-yl]-(4-methyl-quinolin-2-yl)-amine | (4-methyl-quinolin-2-yl)-piperidin-4-yl-amine dihydrochloride (intermediate B9) and 3-ethoxy-4-fluoro-benzaldehyde (intermediate E1) | [M + H]+ 394.4 |
| 110 | 409.96 | [1-(4-chloro-3-ethoxy-benzyl)-piperidin-4-yl]-(4-methyl-quinolin-2-yl)-amine | (4-methyl-quinolin-2-yl)-piperidin-4-yl-amine dihydrochloride (intermediate B9) and 4-chloro-3-ethoxy-benzaldehyde (intermediate E2) | [M + H]+ 410.4 |
| 111 | 405.54 | [1-(3-ethoxy-4-methoxy-benzyl)-piperidin-4-yl]-(4-methyl-quinolin-2-yl)-amine | (4-methyl-quinolin-2-yl)-piperidin-4-yl-amine dihydrochloride (intermediate B9) and 3-ethoxy-4-methoxy-benzaldehyde (commercially available) | [M + H]+ 406.5 |
| 112 | 405.54 | 3-isopropoxy-5-[4-(4-methyl-quinolin-2-ylamino)-piperidin-1-ylmethyl]-phenol | (4-methyl-quinolin-2-yl)-piperidin-4-yl-amine dihydrochloride (intermediate B9) and 3-hydroxy-5-isopropoxy-benzaldehyde (intermediate E19) | [M + H]+ 406.5 |
| 113 | 447.62 | [1-(3,5-diisopropoxy-benzyl)-piperidin-4-yl]-(4-methyl-quinolin-2-yl)-amine | (4-methyl-quinolin-2-yl)-piperidin-4-yl-amine dihydrochloride (intermediate B9) and 3,5-diisopropoxy-benzaldehyde (intermediate E4) | [M + H]+ 448.2 |
| 114 | 437.56 | [1-(3,5-diethoxy-4-fluoro-benzyl)-piperidin-4-yl]-(4-methyl-quinolin-2-yl)-amine | (4-methyl-quinolin-2-yl)-piperidin-4-yl-amine dihydrochloride (intermediate B9) and 3,5-diethoxy-4-fluoro-benzaldehyde (intermediate E5) | [M + H]+ 438.4 |
| 115 | 454.01 | [1-(4-chloro-3,5-diethoxy-benzyl)-piperidin-4-yl]-(4-methyl-quinolin-2-yl)-amine | (4-methyl-quinolin-2-yl)-piperidin-4-yl-amine dihydrochloride (intermediate B9) and 4-chloro-3,5-diethoxy-benzaldehyde (intermediate E6) | [M + H]+ 454.3 |
| 116 | 498.47 | [1-(4-bromo-3,5-diethoxy-benzyl)-piperidin-4-yl]-(4-methyl-quinolin-2-yl)-amine | (4-methyl-quinolin-2-yl)-piperidin-4-yl-amine dihydrochloride (intermediate B9) and 4-bromo-3,5-diethoxy-benzaldehyde (intermediate E7) | [M + H]+ 498.3 |
| 117 | 434.58 | [1-(4-amino-3,5-diethoxy-benzyl)-piperidin-4-yl]-(4- | (4-methyl-quinolin-2-yl)-piperidin-4-yl-amine dihydrochloride (intermediate B9) | [M + H]+ 435.5 |

TABLE 4-continued

| No | MW | Compound Name | Starting Materials | ISP [M + H]+ or M − H]− found |
|---|---|---|---|---|
| | | methyl-quinolin-2-yl)-amine | and 4-amino-3,5-diethoxy-benzaldehyde (intermediate E8) | |
| 118 | 484.64 | [1-(3,5-diethoxy-4-pyrrol-1-yl-benzyl)-piperidin-4-yl]-(4-methyl-quinolin-2-yl)-amine | (4-methyl-quinolin-2-yl)-piperidin-4-yl-amine dihydrochloride (intermediate B9) and 3,5-diethoxy-4-pyrrol-1-yl-benzaldehyde (intermediate E9) | [M + H]+ 485.5 |
| 119 | 409.96 | (4-chloro-quinolin-2-yl)-[1-(3-ethoxy-4-methyl-benzyl)-piperidin-4-yl]-amine | (4-chloro-quinolin-2-yl)-piperidin-4-yl-amine dihydrochloride (intermediate B10) and 3-ethoxy-4-methyl-benzaldehyde (intermediate E10) | [M + H]+ 410.4 |
| 120 | 430.38 | [1-(4-chloro-3-ethoxy-benzyl)-piperidin-4-yl]-(4-chloro-quinolin-2-yl)-amine | (4-chloro-quinolin-2-yl)-piperidin-4-yl-amine dihydrochloride (intermediate B10) and 4-chloro-3-ethoxy-benzaldehyde (intermediate E2) | [M + H]+ 430.4 |
| 121 | 474.43 | [1-(4-chloro-3,5-diethoxy-benzyl)-piperidin-4-yl]-(4-chloro-quinolin-2-yl)-amine | (4-chloro-quinolin-2-yl)-piperidin-4-yl-amine dihydrochloride (intermediate B10) and 4-chloro-3,5-diethoxy-benzaldehyde (intermediate E6) | [M + H]+ 474.2 |
| 122 | 455.00 | [1-(4-amino-3,5-diethoxy-benzyl)-piperidin-4-yl]-(4-chloro-quinolin-2-yl)-amine | (4-chloro-quinolin-2-yl)-piperidin-4-yl-amine dihydrochloride (intermediate B10) and 4-amino-3,5-diethoxy-benzaldehyde (intermediate E8) | [M + H]+ 455.3 |
| 123 | 409.96 | (8-chloro-quinolin-2-yl)-[1-(3-ethoxy-4-methyl-benzyl)-piperidin-4-yl]-amine | (8-chloro-quinolin-2-yl)-piperidin-4-yl-amine dihydrochloride (intermediate B11) and 3-ethoxy-4-methyl-benzaldehyde (intermediate E10) | [M + H]+ 410.3 |
| 124 | 430.38 | [1-(4-chloro-3-ethoxy-benzyl)-piperidin-4-yl]-(8-chloro-quinolin-2-yl)-amine | (8-chloro-quinolin-2-yl)-piperidin-4-yl-amine dihydrochloride (intermediate B11) and 4-chloro-3-ethoxy-benzaldehyde (intermediate E2) | [M + H]+ 430.3 |
| 125 | 411.93 | 4-[4-(8-chloro-quinolin-2-ylamino)-piperidin-1-ylmethyl]-2-ethoxy-phenol | (8-chloro-quinolin-2-yl)-piperidin-4-yl-amine dihydrochloride (intermediate B11) and 3-ethoxy-4-hydroxy-benzaldehyde (commercially available) | [M + H]+ 412.2 |
| 126 | 425.96 | (8-chloro-quinolin-2-yl)-[1-(3-ethoxy-4-methoxy-benzyl)-piperidin-4-yl]-amine | (8-chloro-quinolin-2-yl)-piperidin-4-yl-amine dihydrochloride (intermediate B11) and 3-ethoxy-4-methoxy-benzaldehyde (commercially available) | [M + H]+ 426.2 |
| 127 | 482.07 | (8-chloro-quinolin-2-yl)-{1-[3-ethoxy-4-(1-ethyl-propoxy)-benzyl]-piperidin-4-yl}-amine | (8-chloro-quinolin-2-yl)-piperidin-4-yl-amine dihydrochloride (intermediate B11) and 3-ethoxy-4-(1-ethyl-propoxy)-benzaldehyde (intermediate E15) | [M + H]+ 482.4 |
| 128 | 439.99 | (8-chloro-quinolin-2-yl)-[1-(4-methoxy-3-propoxy-benzyl)-piperidin-4-yl]-amine | (8-chloro-quinolin-2-yl)-piperidin-4-yl-amine dihydrochloride (intermediate B11) and 4-methoxy-3-propoxy-benzaldehyde (intermediate E11) | [M + H]+ 440.3 |
| 129 | 437.97 | [1-(3-allyloxy-4-methoxy-benzyl)-piperidin-4-yl]-(8-chloro-quinolin-2-yl)-amine | (8-chloro-quinolin-2-yl)-piperidin-4-yl-amine dihydrochloride (intermediate B11) and 3-allyloxy-4-methoxy-benzaldehyde (intermediate E16) | [M + H]+ 438.2 |
| 130 | 454.01 | [1-(3-butoxy-4-methoxy-benzyl)-piperidin-4-yl]-(8-chloro-quinolin-2-yl)-amine | (8-chloro-quinolin-2-yl)-piperidin-4-yl-amine dihydrochloride (intermediate B11) and 3-butoxy-4-methoxy-benzaldehyde (intermediate E17) | [M + H]+ 454.4 |
| 131 | 454.01 | (8-chloro-quinolin-2-yl)-[1-(3-isobutoxy-4-methoxy-benzyl)- | (8-chloro-quinolin-2-yl)-piperidin-4-yl-amine dihydrochloride (intermediate | [M + H]+ 454.4 |

TABLE 4-continued

| No | MW | Compound Name | Starting Materials | ISP [M + H]+ or M − H]− found |
|---|---|---|---|---|
| | | piperidin-4-yl]-amine | B11) and 3-isobutoxy-4-methoxy-benzaldehyde (intermediate E12) | |
| 132 | 478.04 | (8-chloro-quinolin-2-yl)-[1-(8-ethoxy-2,2-dimethyl-2H-chromen-6-ylmethyl)-piperidin-4-yl]-amine | (8-chloro-quinolin-2-yl)-piperidin-4-yl-amine dihydrochloride (intermediate B11) and 8-ethoxy-2,2-dimethyl-2H-chromene-6-carbaldehyde (intermediate E18) | [M + H]+ 478.2 |
| 133 | 439.99 | (8-chloro-quinolin-2-yl)-[1-(3,5-diethoxy-benzyl)-piperidin-4-yl]-amine | (8-chloro-quinolin-2-yl)-piperidin-4-yl-amine dihydrochloride (intermediate B11) and 3,5-diethoxy-benzaldehyde (intermediate E3) | [M + H]+ 440.3 |
| 134 | 512.05 | 4-[4-(8-chloro-quinolin-2-ylamino)-piperidin-1-ylmethyl]-2,6-diethoxy-benzoic acid ethyl ester | (8-chloro-quinolin-2-yl)-piperidin-4-yl-amine dihydrochloride (intermediate B11) and 2,6-diethoxy-4-formyl-benzoic acid ethyl ester (intermediate E20) | [M + H]+ 512.3 |
| 135 | 457.98 | (8-chloro-quinolin-2-yl)-[1-(3,5-diethoxy-4-fluoro-benzyl)-piperidin-4-yl]-amine | (8-chloro-quinolin-2-yl)-piperidin-4-yl-amine dihydrochloride (intermediate B11) and 3,5-diethoxy-4-fluoro-benzaldehyde (intermediate E5) | [M + H]+ 458.2 |
| 136 | 518.89 | [1-(4-bromo-3,5-diethoxy-benzyl)-piperidin-4-yl]-(8-chloro-quinolin-2-yl)-amine | (8-chloro-quinolin-2-yl)-piperidin-4-yl-amine dihydrochloride (intermediate B11) and 4-bromo-3,5-diethoxy-benzaldehyde (intermediate E7) | [M + H]+ 520.2 |
| 137 | 505.06 | (8-chloro-quinolin-2-yl)-[1-(3,5-diethoxy-4-pyrrol-1-yl-benzyl)-piperidin-4-yl]-amine | (8-chloro-quinolin-2-yl)-piperidin-4-yl-amine dihydrochloride (intermediate B11) and 3,5-diethoxy-4-pyrrol-1-yl-benzaldehyde (intermediate E9) | [M + H]+ 505.2 |
| 138 | 375.52 | [1-(3-ethoxy-4-methyl-benzyl)-piperidin-4-yl]-isoquinolin-1-yl-amine | isoquinolin-1-yl-piperidin-4-yl-amine dihydrochloride (intermediate B12) and 3-ethoxy-4-methyl-benzaldehyde (intermediate E10) | [M + H]+ 376.4 |
| 139 | 379.48 | [1-(3-ethoxy-4-fluoro-benzyl)-piperidin-4-yl]-isoquinolin-1-yl-amine | isoquinolin-1-yl-piperidin-4-yl-amine dihydrochloride (intermediate B12) and 3-ethoxy-4-fluoro-benzaldehyde (intermediate E1) | [M + H]+ 380.4 |
| 140 | 395.93 | [1-(4-chloro-3-ethoxy-benzyl)-piperidin-4-yl]-isoquinolin-1-yl-amine | isoquinolin-1-yl-piperidin-4-yl-amine dihydrochloride (intermediate B12) and 4-chloro-3-ethoxy-benzaldehyde (intermediate E2) | [M + H]+ 396.3 |
| 141 | 391.51 | [1-(3-ethoxy-4-methoxy-benzyl)-piperidin-4-yl]-isoquinolin-1-yl-amine | isoquinolin-1-yl-piperidin-4-yl-amine dihydrochloride (intermediate B12) and 3-ethoxy-4-methoxy-benzaldehyde (commercially available) | [M + H]+ 392.2 |
| 142 | 405.54 | isoquinolin-1-yl-[1-(4-methoxy-3-propoxy-benzyl)-piperidin-4-yl]-amine | isoquinolin-1-yl-piperidin-4-yl-amine dihydrochloride (intermediate B12) and 4-methoxy-3-propoxy-benzaldehyde (intermediate E11) | [M + H]+ 406.4 |
| 143 | 403.53 | [1-(3-allyloxy-4-methoxy-benzyl)-piperidin-4-yl]-isoquinolin-1-yl-amine | isoquinolin-1-yl-piperidin-4-yl-amine dihydrochloride (intermediate B12) and 3-allyloxy-4-methoxy-benzaldehyde (intermediate E16) | [M + H]+ 404.5 |
| 144 | 419.57 | [1-(3-butoxy-4-methoxy-benzyl)-piperidin-4-yl]-isoquinolin-1-yl-amine | isoquinolin-1-yl-piperidin-4-yl-amine dihydrochloride (intermediate B12) and 3-butoxy-4-methoxy-benzaldehyde (intermediate E17) | [M + H]+ 420.4 |
| 145 | 419.57 | [1-(3-isobutoxy-4-methoxy-benzyl)-piperidin-4-yl]-isoquinolin-1-yl-amine | isoquinolin-1-yl-piperidin-4-yl-amine dihydrochloride (intermediate B12) and 3-isobutoxy-4-methoxy-benzaldehyde (intermediate E12) | [M + H]+ 420.4 |

TABLE 4-continued

| No | MW | Compound Name | Starting Materials | ISP [M + H]+ or M − H− found |
|---|---|---|---|---|
| 146 | 443.59 | [1-(8-ethoxy-2,2-dimethyl-2H-chromen-6-ylmethyl)-piperidin-4-yl]-isoquinolin-1-yl-amine | isoquinolin-1-yl-piperidin-4-yl-amine dihydrochloride (intermediate B12) and 8-ethoxy-2,2-dimethyl-2H-chromene-6-carbaldehyde (intermediate E18) | [M + H]+ 444.4 |
| 147 | 405.54 | [1-(3,5-diethoxy-benzyl)-piperidin-4-yl]-isoquinolin-1-yl-amine | isoquinolin-1-yl-piperidin-4-yl-amine dihydrochloride (intermediate B12) and 3,5-diethoxy-benzaldehyde (intermediate E3) | [M + H]+ 406.4 |
| 148 | 391.51 | 3-isopropoxy-5-[4-(isoquinolin-1-ylamino)-piperidin-1-ylmethyl]-phenol | isoquinolin-1-yl-piperidin-4-yl-amine dihydrochloride (intermediate B12) and 3-hydroxy-5-isopropoxy-benzaldehyde (intermediate E19) | [M + H]+ 392.2 |
| 149 | 433.60 | [1-(3,5-diisopropoxy-benzyl)-piperidin-4-yl]-isoquinolin-1-yl-amine | isoquinolin-1-yl-piperidin-4-yl-amine dihydrochloride (intermediate B12) and 3,5-diisopropoxy-benzaldehyde (intermediate E4) | [M + H]+ 434.4 |
| 150 | 423.53 | [1-(3,5-diethoxy-4-fluoro-benzyl)-piperidin-4-yl]-isoquinolin-1-yl-amine | isoquinolin-1-yl-piperidin-4-yl-amine dihydrochloride (intermediate B12) and 3,5-diethoxy-4-fluoro-benzaldehyde (intermediate E5) | [M + H]+ 424.3 |
| 151 | 439.99 | [1-(4-chloro-3,5-diethoxy-benzyl)-piperidin-4-yl]-isoquinolin-1-yl-amine | isoquinolin-1-yl-piperidin-4-yl-amine dihydrochloride (intermediate B12) and 4-chloro-3,5-diethoxy-benzaldehyde (intermediate E6) | [M + H]+ 440.4 |
| 152 | 484.44 | [1-(4-bromo-3,5-diethoxy-benzyl)-piperidin-4-yl]-isoquinolin-1-yl-amine | isoquinolin-1-yl-piperidin-4-yl-amine dihydrochloride (intermediate B12) and 4-bromo-3,5-diethoxy-benzaldehyde (intermediate E7) | [M + H]+ 484.3 |
| 153 | 470.62 | [1-(3,5-diethoxy-4-pyrrol-1-yl-benzyl)-piperidin-4-yl]-isoquinolin-1-yl-amine | isoquinolin-1-yl-piperidin-4-yl-amine dihydrochloride (intermediate B12) and 3,5-diethoxy-4-pyrrol-1-yl-benzaldehyde (intermediate E9) | [M + H]+ 471.4 |
| 154 | 409.96 | (3-chloro-isoquinolin-1-yl)-[1-(3-ethoxy-4-methyl-benzyl)-piperidin-4-yl]-amine | (3-chloro-isoquinolin-1-yl)-piperidin-4-yl-amine dihydrochloride (intermediate B13) and 3-ethoxy-4-methyl-benzaldehyde (intermediate E10) | [M + H]+ 410.4 |
| 155 | 413.92 | (3-chloro-isoquinolin-1-yl)-[1-(3-ethoxy-4-fluoro-benzyl)-piperidin-4-yl]-amine | (3-chloro-isoquinolin-1-yl)-piperidin-4-yl-amine dihydrochloride (intermediate B13) and 3-ethoxy-4-fluoro-benzaldehyde (intermediate E1) | [M + H]+ 414.3 |
| 156 | 430.38 | [1-(4-chloro-3-ethoxy-benzyl)-piperidin-4-yl]-(3-chloro-isoquinolin-1-yl)-amine | (3-chloro-isoquinolin-1-yl)-piperidin-4-yl-amine dihydrochloride (intermediate B13) and 4-chloro-3-ethoxy-benzaldehyde (intermediate E2) | [M + H]+ 430.4 |
| 157 | 411.93 | 4-[4-(3-chloro-isoquinolin-1-ylamino)-piperidin-1-ylmethyl]-2-ethoxy-phenol | (3-chloro-isoquinolin-1-yl)-piperidin-4-yl-amine dihydrochloride (intermediate B13) and 3-ethoxy-4-hydroxy-benzaldehyde (commercially available) | [M + H]+ 412.5 |
| 158 | 425.96 | (3-chloro-isoquinolin-1-yl)-[1-(3-ethoxy-4-methoxy-benzyl)-piperidin-4-yl]-amine | (3-chloro-isoquinolin-1-yl)-piperidin-4-yl-amine dihydrochloride (intermediate B13) and 3-ethoxy-4-methoxy-benzaldehyde (commercially available) | [M + H]+ 426.3 |
| 159 | 461.94 | (3-chloro-isoquinolin-1-yl)-[1-(4-difluoromethoxy-3-ethoxy-benzyl)-piperidin-4-yl]-amine | (3-chloro-isoquinolin-1-yl)-piperidin-4-yl-amine dihydrochloride (intermediate B13) and 4-difluoromethoxy-3-ethoxy-benzaldehyde (commercially available) | [M + H]+ 462.4 |

TABLE 4-continued

| No | MW | Compound Name | Starting Materials | ISP [M + H]+ or M − H]− found |
|---|---|---|---|---|
| 160 | 454.01 | (3-chloro-isoquinolin-1-yl)-[1-(3-ethoxy-4-isopropoxy-benzyl)-piperidin-4-yl]-amine | (3-chloro-isoquinolin-1-yl)-piperidin-4-yl-amine dihydrochloride (intermediate B13) and 3-ethoxy-4-isopropoxy-benzaldehyde (commercially available) | [M + H]+ 454.3 |
| 161 | 468.04 | (3-chloro-isoquinolin-1-yl)-[1-(3-ethoxy-4-isobutoxy-benzyl)-piperidin-4-yl]-amine | (3-chloro-isoquinolin-1-yl)-piperidin-4-yl-amine dihydrochloride (intermediate B13) and 3-ethoxy-4-isobutoxy-benzaldehyde (commercially available) | [M + H]+ 468.4 |
| 162 | 439.99 | (3-chloro-isoquinolin-1-yl)-[1-(4-methoxy-3-propoxy-benzyl)-piperidin-4-yl]-amine | (3-chloro-isoquinolin-1-yl)-piperidin-4-yl-amine dihydrochloride (intermediate B13) and 4-methoxy-3-propoxy-benzaldehyde (intermediate E11) | [M + H]+ 440.4 |
| 163 | 437.97 | [1-(3-allyloxy-4-methoxy-benzyl)-piperidin-4-yl]-(3-chloro-isoquinolin-1-yl)-amine | (3-chloro-isoquinolin-1-yl)-piperidin-4-yl-amine dihydrochloride (intermediate B13) and 3-allyloxy-4-methoxy-benzaldehyde (intermediate E16) | [M + H]+ 438.3 |
| 164 | 454.01 | [1-(3-butoxy-4-methoxy-benzyl)-piperidin-4-yl]-(3-chloro-isoquinolin-1-yl)-amine | (3-chloro-isoquinolin-1-yl)-piperidin-4-yl-amine dihydrochloride (intermediate B13) and 3-butoxy-4-methoxy-benzaldehyde (intermediate E17) | [M + H]+ 454.2 |
| 165 | 454.01 | (3-chloro-isoquinolin-1-yl)-[1-(3-isobutoxy-4-methoxy-benzyl)-piperidin-4-yl]-amine | (3-chloro-isoquinolin-1-yl)-piperidin-4-yl-amine dihydrochloride (intermediate B13) and 3-isobutoxy-4-methoxy-benzaldehyde (intermediate E12) | [M + H]+ 454.3 |
| 166 | 478.04 | (3-chloro-isoquinolin-1-yl)-[1-(8-ethoxy-2,2-dimethyl-2H-chromen-6-ylmethyl)-piperidin-4-yl]-amine | (3-chloro-isoquinolin-1-yl)-piperidin-4-yl-amine dihydrochloride (intermediate B13) and 8-ethoxy-2,2-dimethyl-2H-chromene-6-carbaldehyde (intermediate E18) | [M + H]+ 478.2 |
| 167 | 439.99 | (3-chloro-isoquinolin-1-yl)-[1-(3,5-diethoxy-benzyl)-piperidin-4-yl]-amine | (3-chloro-isoquinolin-1-yl)-piperidin-4-yl-amine dihydrochloride (intermediate B13) and 3,5-diethoxy-benzaldehyde (intermediate E3) | [M + H]+ 440.4 |
| 168 | 457.98 | (3-chloro-isoquinolin-1-yl)-[1-(3,5-diethoxy-4-fluoro-benzyl)-piperidin-4-yl]-amine | (3-chloro-isoquinolin-1-yl)-piperidin-4-yl-amine dihydrochloride (intermediate B13) and 3,5-diethoxy-4-fluoro-benzaldehyde (intermediate E5) | [M + H]+ 458.4 |
| 169 | 474.43 | [1-(4-chloro-3,5-diethoxy-benzyl)-piperidin-4-yl]-(3-chloro-isoquinolin-1-yl)-amine | (3-chloro-isoquinolin-1-yl)-piperidin-4-yl-amine dihydrochloride (intermediate B13) and 4-chloro-3,5-diethoxy-benzaldehyde (intermediate E6) | [M + H]+ 474.2 |
| 170 | 518.89 | [1-(4-bromo-3,5-diethoxy-benzyl)-piperidin-4-yl]-(3-chloro-isoquinolin-1-yl)-amine | (3-chloro-isoquinolin-1-yl)-piperidin-4-yl-amine dihydrochloride (intermediate B13) and 4-bromo-3,5-diethoxy-benzaldehyde (intermediate E7) | [M + H]+ 520.2 |
| 171 | 455.00 | [1-(4-amino-3,5-diethoxy-benzyl)-piperidin-4-yl]-(3-chloro-isoquinolin-1-yl)-amine | (3-chloro-isoquinolin-1-yl)-piperidin-4-yl-amine dihydrochloride (intermediate B13) and 4-amino-3,5-diethoxy-benzaldehyde (intermediate E8) | [M + H]+ 455.4 |
| 172 | 384.48 | 5-[1-(3-ethoxy-4-methyl-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3-ethoxy-4-methyl-benzaldehyde (intermediate E10) | [M + H]+ 384.4 |
| 173 | 388.44 | 5-[1-(3-ethoxy-4-fluoro-benzyl)-piperidin-4-ylamino]-pyrazine-2-carboxylic | 5-(piperidin-4-ylamino)-pyrazine-2-carboxylic acid methyl ester dihydrochloride (intermediate B14) and 3-ethoxy- | [M + H]+ 389.3 |

TABLE 4-continued

| No | MW | Compound Name | Starting Materials | ISP [M + H]+ or M − H]− found |
|---|---|---|---|---|
| | | acid methyl ester | 4-fluoro-benzaldehyde (intermediate E1) | |
| 174 | 404.90 | 5-[1-(4-chloro-3-ethoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 4-chloro-3-ethoxy-benzaldehyde (intermediate E2) | [M + H]+ 405.8 |
| 175 | 386.45 | 5-[1-(3-ethoxy-4-hydroxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3-ethoxy-4-hydroxy-benzaldehyde (commercially available) | [M + H]+ 387.3 |
| 176 | 400.48 | 5-[1-(3-ethoxy-4-methoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3-ethoxy-4-methoxy-benzaldehyde (commercially available) | [M + H]+ 401.3 |
| 177 | 428.53 | 5-[1-(3-ethoxy-4-isopropoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3-ethoxy-4-isopropoxy-benzaldehyde (commercially available) | [M + H]+ 429.4 |
| 178 | 414.51 | 5-[1-(4-methoxy-3-propoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 4-methoxy-3-propoxy-benzaldehyde (intermediate E11) | [M + H]+ 415.4 |
| 179 | 418.47 | 5-{1-[3-(2-fluoro-ethoxy)-4-methoxy-benzyl]-piperidin-4-ylamino}-pyrazine-2-carboxylic acid methyl ester | 5-(piperidin-4-ylamino)-pyrazine-2-carboxylic acid methyl ester dihydrochloride (intermediate B14) and 3-(2-fluoro-ethoxy)-4-methoxy-benzaldehyde (intermediate E21) | [M + H]+ 419.2 |
| 180 | 428.53 | 5-[1-(3-isobutoxy-4-methoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3-isobutoxy-4-methoxy-benzaldehyde (intermediate E12) | [M + H]+ 429.4 |
| 181 | 452.55 | 5-[1-(8-ethoxy-2,2-dimethyl-2H-chromen-6-ylmethyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 8-ethoxy-2,2-dimethyl-2H-chromene-6-carbaldehyde (intermediate E18) | [M + H]+ 453.2 |
| 182 | 414.51 | 5-[1-(3,5-diethoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3,5-diethoxy-benzaldehyde (intermediate E3) | [M + H]+ 415.4 |
| 183 | 442.56 | 5-[1-(3,5-diisopropoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3,5-diisopropoxy-benzaldehyde (intermediate E4) | [M + H]+ 443.4 |
| 184 | 432.50 | 5-[1-(3,5-diethoxy-4-fluoro-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3,5-diethoxy-4-fluoro-benzaldehyde (intermediate E5) | [M + H]+ 433.3 |
| 185 | 448.95 | 5-[1-(4-chloro-3,5-diethoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 4-chloro-3,5-diethoxy-benzaldehyde (intermediate E6) | [M + H]+ 449.2 |

TABLE 4-continued

| No | MW | Compound Name | Starting Materials | ISP [M + H]+ or M − H]− found |
|---|---|---|---|---|
| 186 | 493.41 | 5-[1-(4-bromo-3,5-diethoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 4-bromo-3,5-diethoxy-benzaldehyde (intermediate E7) | [M + H]+ 495.3 |
| 187 | 429.52 | 5-[1-(4-amino-3,5-diethoxy-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 4-amino-3,5-diethoxy-benzaldehyde (intermediate E8) | [M + H]+ 430.4 |
| 188 | 479.58 | 5-[1-(3,5-diethoxy-4-pyrrol-1-yl-benzyl)-piperidin-4-ylamino]-pyrazine-2-carboxylic acid methyl ester | 5-(piperidin-4-ylamino)-pyrazine-2-carboxylic acid methyl ester dihydrochloride (intermediate B14) and 3,5-diethoxy-4-pyrrol-1-yl-benzaldehyde (intermediate E9) | [M + H]+ 480.3 |

Example 189

2-[1-(3-Ethoxy-4-methyl-benzyl)-piperidin-4-ylamino]-isonicotinonitrile

Step 1: 4-(4-Cyano-pyridin-2-ylamino)-piperidine-1-carboxylic acid tert-butyl ester A solution of 2-chloro-isonicotinonitrile (2.00 g, 14.43 mmol, 1.0 equiv; commercially available) and 4-amino-piperidine-1-carboxylic acid tert-butyl ester (3.18 g, 15.88 mmol, 1.1 equiv; commercially available) in DMAc (10 mL) was heated by microwave irradiation to 150° C. for 30 min. The solvent was evaporated under reduced pressure and the crude material purified with column chromatography on silica eluting with heptane/ethyl acetate (1:1) to yield 0.30 g (7%) of the title compound. $^1$H NMR (300 MHz, CDCl$_3$): δ 1.25-1.42 (m, 2H), 1.43 (s, 9H), 1.93-1.97 (m, 2H), 2.83-2.93 (m, 2H), 3.71-3.81 (m, 1H), 3.97-4.02 (m, 2H), 4.77 (d, J=8.1 Hz, 1H), 6.51 (s, 1H), 6.66 (d, J=5.2 Hz, 1H), 8.11 (d, J=5.2 Hz, 1H). MS (ISP): 303.0 [M+H]+.

Step 2: 2-(Piperidin-4-ylamino)-isonicotinonitrile dihydrochloride (Intermediate B15)

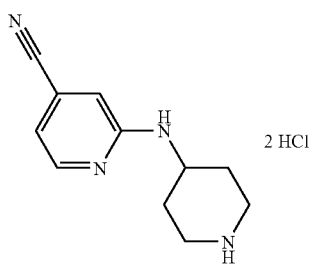

A solution of 4-(4-cyano-pyridin-2-ylamino)-piperidine-1-carboxylic acid tert-butyl ester (0.30 g, 1.00 mmol) in 4 M HCl in dioxane (15 mL) was stirred at rt for 1 h. The solvent was removed under reduced pressure and the crude product used in the consecutive step without further purification assuming quantitative deprotection and formation of the dihydrochloride salt. MS (ISP): 203.1 [M+H]+.

Step 3: 2-[1-(3-Ethoxy-4-methyl-benzyl)-piperidin-4-ylamino]-isonicotinonitrile

To a solution of 2-(piperidin-4-ylamino)-isonicotinonitrile dihydrochloride (43.0 mg, 0.18 mmol, 1.0 equiv; intermediate B15) in ethanol (2 mL), acetic acid (54.1 mg, 0.9 mmol, 5.0 equiv) and triethylamine (36.4 mg, 0.36 mmol, 2.0 equiv) was added 3-ethoxy-4-methyl-benzaldehyde (36.1 mg, 0.22 mmol, 1.2 equiv; intermediate E10) and the mixture stirred at 50° C. After 1 h, sodium cyanoborohydride (13.8 mg, 0.22 mmol, 1.2 equiv), dissolved in ethanol (0.5 mL), was added and the mixture stirred at 50° C. over night. Removal of the solvent under reduced pressure and purification by preparative HPLC on reversed phase eluting with a gradient of acetonitrile/water provided 1.8 mg (3%) of the title compound. MS (ISP): 351.5 [M+H]+.

Example 190

2-[1-(3-Ethoxy-4-methyl-benzyl)-piperidin-4-ylamino]-isonicotinamide

The title compound was isolated as a side-product in the synthesis of 2-[1-(3-ethoxy-4-methyl-benzyl)-piperidin-4-ylamino]-isonicotinonitrile (example 189) after purification by preparative HPLC on reversed phase eluting with a gradient of acetonitrile/water in a yield of 10.5 mg (16%). MS (ISP): 369.3 [M+H]+.

Example 191

2-[1-(4-Chloro-3-ethoxy-benzyl)-piperidin-4-ylamino]-isonicotinonitrile

The title compound was prepared in analogy to the synthesis of 2-[1-(3-ethoxy-4-methyl-benzyl)-piperidin-4-ylamino]-isonicotinonitrile (example 189) from 2-(piperidin-4-ylamino)-isonicotinonitrile dihydrochloride (intermediate B15) and 4-chloro-3-ethoxy-benzaldehyde (intermediate E2) in a yield of 3.8 mg (6%). MS (ISP): 371.1 [M+H]+.

Example 192

2-[1-(4-Chloro-3-ethoxy-benzyl)-piperidin-4-ylamino]-isonicotinamide

The title compound was isolated as a side-product in the synthesis of 2-[1-(4-chloro-3-ethoxy-benzyl)-piperidin-4-ylamino]-isonicotinonitrile (example 191) after purification by preparative HPLC on reversed phase eluting with a gradient of acetonitrile/water in a yield of 15.2 mg (22%). MS (ISP): 389.5 [M+]$^+$.

Example 193

2-[1-(3,5-Diisopropoxy-benzyl)-piperidin-4-ylamino]-isonicotinonitrile

The title compound was prepared in analogy to the synthesis of 2-[1-(3-ethoxy-4-methyl-benzyl)-piperidin-4-ylamino]-isonicotinonitrile (example 189) from 2-(piperidin-4-ylamino)-isonicotinonitrile dihydrochloride (intermediate B15) and 3,5-diisopropoxy-benzaldehyde (intermediate E4) in a yield of 3.6 mg (5%). MS (ISP): 409.5 [M+H]$^+$.

Example 194

2-[1-(3,5-Diisopropoxy-benzyl)-piperidin-4-ylamino]-isonicotinamide

The title compound was isolated as a side-product in the synthesis of 2-[1-(3,5-diisopropoxy-benzyl)-piperidin-4-ylamino]-isonicotinonitrile (example 193) after purification by preparative HPLC on reversed phase eluting with a gradient of acetonitrile/water in a yield of 11.4 mg (15%). MS (ISP): 427.5 [M+H]$^+$.

Example 195

2-[1-(3,5-Diethoxy-4-fluoro-benzyl)-piperidin-4-ylamino]-isonicotinonitrile

The title compound was prepared in analogy to the synthesis of 2-[1-(3-ethoxy-4-methyl-benzyl)-piperidin-4-ylamino]-isonicotinonitrile (example 189) from 2-(piperidin-4-ylamino)-isonicotinonitrile dihydrochloride (intermediate B15) and 3,5-diethoxy-4-fluoro-benzaldehyde (intermediate E5) in a yield of 4.3 mg (6%). MS (ISP): 399.3 [M+H]$^+$.

Example 196

2-[1-(3,5-Diethoxy-4-fluoro-benzyl)-piperidin-4-ylamino]-isonicotinamide

The title compound was isolated as a side-product in the synthesis of 2-[1-(3,5-diethoxy-4-fluoro-benzyl)-piperidin-4-ylamino]-isonicotinonitrile (example 195) after purification by preparative HPLC on reversed phase eluting with a gradient of acetonitrile/water in a yield of 19.1 mg (26%). MS (ISP): 417.5 [M+H]$^+$.

Example 197

6-[1-(4-Methoxy-3-propoxy-benzyl)-piperidin-4-ylamino]-4-trifluoromethyl-nicotinamide To a solution of 6-(piperidin-4-ylamino)-4-trifluoromethyl-nicotinic acid methyl ester dihydrochloride (56.42 mg, 0.15 mmol, 1.0 equiv; intermediate B7) in ethanol (2 mL), acetic acid (72.1 mg, 1.2 mmol, 8.0 equiv) and N-ethyl diisopropylamine (77.6 mg, 0.6 mmol, 4.0 equiv) was added 4-methoxy-3-propoxy-benzaldehyde (35.0 mg, 0.18 mmol, 1.2 equiv; intermediate E11) and the mixture stirred at 55° C. After 1 h, sodium cyanoborohydride (47.1 mg, 0.75 mmol, 5.0 equiv), dissolved in ethanol (0.5 mL), was added and the mixture stirred at 55° C. over night. The solvents were removed under reduced pressure and the residue taken up in DMAc (0.5 ml). Potassium cyanide (30.0 mg, 0.47 mmol, 3.1 equiv) and a conc. solution of NH$_4$OH (1 mL) was added and the reaction mixture heated by microwave irradiation to 100° C. for 8 h. Removal of the solvent under reduced pressure and purification by preparative HPLC on reversed phase eluting with a gradient of acetonitrile/water provided 26.5 mg (38%) of the title compound. MS (ISP): 468.4 [M+H]$^+$.

Example 198

6-[1-(3-Isobutoxy-4-methoxy-benzyl)-piperidin-4-ylamino]-4-trifluoromethyl-nicotinamide The title compound was prepared in analogy to the synthesis of 6-[1-(4-methoxy-3-propoxy-benzyl)-piperidin-4-ylamino]-4-trifluoromethyl-nicotinamide (example 197) from 6-(piperidin-4-ylamino)-4-trifluoromethyl-nicotinic acid methyl ester dihydrochloride (intermediate B7) and 3-isobutoxy-4-methoxy-benzaldehyde (intermediate E12) in a yield of 15.1 mg (21%). MS (ISP): 482.4 [M+H]$^+$.

Example 199

6-[1-(4-Chloro-3-ethoxy-benzyl)-piperidin-4-ylamino]-4-trifluoromethyl-nicotinamide The title compound was prepared in analogy to the synthesis of 6-[1-(4-methoxy-3-propoxy-benzyl)-piperidin-4-ylamino]-4-trifluoromethyl-nicotinamide (example 197) from 6-(piperidin-4-ylamino)-4-trifluoromethyl-nicotinic acid methyl ester dihydrochloride (intermediate B7) and 4-chloro-3-ethoxy-benzaldehyde (intermediate E2) in a yield of 13.1 mg (19%). MS (ISP): 458.3 [M+H]$^+$.

Example 200

6-[1-(3,5-Diethoxy-4-fluoro-benzyl)-piperidin-4-ylamino]-4-trifluoromethyl-nicotinamide The title compound was prepared in analogy to the synthesis of 6-[1-(4-methoxy-3-propoxy-benzyl)-piperidin-4-ylamino]-4-trifluoromethyl-nicotinamide (example 197) from 6-(piperidin-4-ylamino)-4-trifluoromethyl-nicotinic acid methyl ester dihydrochloride (intermediate B7) and 3,5-diethoxy-4-fluoro-benzaldehyde (intermediate E5) in a yield of 2.3 mg (3%). MS (ISP): 485.3 [M+H]$^+$.

Example 201

6-[1-(3-Ethoxy-4-hydroxy-benzyl)-piperidin-4-ylamino]-4-trifluoromethyl-nicotinic acid To a solution of 6-(piperidin-4-ylamino)-4-trifluoromethyl-nicotinic acid methyl ester dihydrochloride (56.42 mg, 0.15 mmol, 1.0 equiv; intermediate B7) in ethanol (2 mL), acetic acid (72.1 mg, 1.2 mmol, 8.0 equiv) and N-ethyl diisopropylamine (77.6 mg, 0.6 mmol, 4.0 equiv) was added 3-ethoxy-4-hydroxy-benzaldehyde (30.0 mg, 0.18 mmol, 1.2 equiv; commercially available) and the mixture stirred at 55° C. After 1 h, sodium cyanoborohydride (47.1 mg, 0.75 mmol, 5.0 equiv), dissolved in ethanol (0.5 mL), was added and the mixture stirred at 55° C. over night. A solution of 10 M NaOH (0.5 mL) was added and the reaction mixture heated by microwave irradiation to 100° C. for 15 min. Removal of the solvent under reduced pressure and purification by preparative HPLC on reversed phase eluting with a gradient of acetonitrile/water provided 4.3 mg (7%) of the title compound. MS (ISP): 440.3 [M+H]$^+$.

Example 202

6-[1-(3-Ethoxy-4-methoxy-benzyl)-piperidin-4-ylamino]-4-trifluoromethyl-nicotinic acid The title compound was prepared in analogy to the synthesis of 6-[1-(3-ethoxy-4-hydroxy-benzyl)-piperidin-4-ylamino]-4-trifluoromethyl-nicotinic acid (example 201) from 6-(piperidin-4-ylamino)-4-trifluoromethyl-nicotinic acid methyl ester dihydrochloride (intermediate B7) and 3-ethoxy-4-methoxy-benzaldehyde (commercially available) in a yield of 15.3 mg (22%). MS (ISP): 454.2 [M+H]$^+$.

Example 203

6-[1-(4-Methoxy-3-propoxy-benzyl)-piperidin-4-ylamino]-4-trifluoromethyl-nicotinic acid The title compound was prepared in analogy to the synthesis of 6-[1-(3-ethoxy-4-hydroxy-benzyl)-piperidin-4-ylamino]-4-trifluoromethyl-nicotinic acid (example 201) from 6-(piperidin-4-ylamino)-4-trifluoromethyl-nicotinic acid methyl ester dihydrochloride (intermediate B7) and 4-methoxy-3-propoxy-benzaldehyde (intermediate E11) in a yield of 16.4 mg (23%). MS (ISP): 468.3 [M+H]$^+$.

Example 204

6-[1-(3-Isobutoxy-4-methoxy-benzyl)-piperidin-4-ylamino]-4-trifluoromethyl-nicotinic acid The title compound was prepared in analogy to the synthesis of 6-[1-(3-ethoxy-4-hydroxy-benzyl)-piperidin-4-ylamino]-4-trifluoromethyl-nicotinic acid (example 201) from 6-(piperidin-4-ylamino)-4-trifluoromethyl-nicotinic acid methyl ester dihydrochloride (intermediate B7) and 3-isobutoxy-4-methoxy-benzaldehyde (intermediate E12) in a yield of 9.0 mg (12%). MS (ISP): 482.3 [M+H]$^+$.

Example 205

5-[1-(4-Chloro-3-ethoxy-benzyl)-piperidin-4-ylamino]-pyrazine-2-carboxylic acid amide The title compound was prepared in analogy to the synthesis of 6-[1-(4-methoxy-3-propoxy-benzyl)-piperidin-4-ylamino]-4-trifluoromethyl-nicotinamide (example 197) from 5-(piperidin-4-ylamino)-pyrazine-2-carboxylic acid methyl ester dihydrochloride (intermediate B14) and 4-chloro-3-ethoxy-benzaldehyde (intermediate E2) in a yield of 12.1 mg (21%). MS (ISP): 390.3 [M+H]$^+$.

Example 206

6-[1-(4-Chloro-3,5-diethoxy-benzyl)-piperidin-4-ylamino]-N-(2-hydroxy-ethyl)-nicotinamide To a mixture of 6-[1-(4-chloro-3,5-diethoxy-benzyl)-piperidin-4-ylamino]-nicotinic acid (65.09 mg, 0.15 mmol, 1.0 equiv; example 70) and 2-amino-ethanol (46.4 mg, 0.25 mmol, 1.67 equiv; commercially available) in dry DMF (2.0 mL) and N-ethyl diisopropylamine (0.3 mL) was added HATU (68.44 mg, 0.18 mmol, 1.2 quiv; commercially available) and the reaction stirred at 60° C. over night. Removal of the solvent under reduced pressure and purification by preparative HPLC on reversed phase eluting with a gradient of acetonitrile/water provided 30.1 mg (42%) of the title compound. MS (ISP): 477.3 [M+H]$^+$.

Examples 207 to 217

According to the procedure described for the synthesis of example 207 further nicotinamide derivatives have been synthesized from 6-[1-(4-chloro-3,5-diethoxy-benzyl)-piperidin-4-ylamino]-nicotinic acid (example 70) and the respective amine as indicated in Table 5. The results are compiled in Table 5 and comprise example 207 to example 217.

TABLE 5

| No | MW | Compound Name | Starting Materials | ISP [M + H]$^+$ found |
|---|---|---|---|---|
| 207 | 487.04 | 6-[1-(4-chloro-3,5-diethoxy-benzyl)-piperidin-4-ylamino]-N-cyclobutyl-nicotinamide | 6-[1-(4-chloro-3,5-diethoxy-benzyl)-piperidin-4-ylamino]-nicotinic acid (example 70) and cyclobutylamine (commercially available) | 487.4 |
| 208 | 490.99 | ({6-[1-(4-chloro-3,5-diethoxy-benzyl)-piperidin-4-ylamino]-pyridine-3-carbonyl}-amino)-acetic acid | 6-[1-(4-chloro-3,5-diethoxy-benzyl)-piperidin-4-ylamino]-nicotinic acid (example 70) and amino-acetic acid (commercially available) | 491.5 |
| 209 | 491.03 | 6-[1-(4-chloro-3,5-diethoxy-benzyl)-piperidin-4-ylamino]-N-(2-methoxy-ethyl)-nicotinamide | 6-[1-(4-chloro-3,5-diethoxy-benzyl)-piperidin-4-ylamino]-nicotinic acid (example 70) and 2-methoxy-ethylamine (commercially available) | 491.3 |
| 210 | 503.04 | {6-[1-(4-chloro-3,5-diethoxy-benzyl)-piperidin-4-ylamino]-pyridin-3-yl}-morpholin-4-yl-methanone | 6-[1-(4-chloro-3,5-diethoxy-benzyl)-piperidin-4-ylamino]-nicotinic acid (example 70) and morpholine (commercially available) | 503.3 |

TABLE 5-continued

| No | MW | Compound Name | Starting Materials | ISP [M + H]+ found |
|---|---|---|---|---|
| 211 | 503.04 | {6-[1-(4-Chloro-3,5-diethoxy-benzyl)-piperidin-4-ylamino]-pyridin-3-yl}-((R)-3-hydroxy-pyrrolidin-1-yl)-methanone | 6-[1-(4-chloro-3,5-diethoxy-benzyl)-piperidin-4-ylamino]-nicotinic acid (example 70) and (R)-pyrrolidin-3-ol (commercially available) | 503.3 |
| 212 | 507.03 | 6-[1-(4-chloro-3,5-diethoxy-benzyl)-piperidin-4-ylamino]-N-(2-hydroxy-1-hydroxymethyl-ethyl)-nicotinamide | 6-[1-(4-chloro-3,5-diethoxy-benzyl)-piperidin-4-ylamino]-nicotinic acid (example 70) and 2-(2-hydroxy-ethylamino)-ethanol (commercially available) | 507.4 |
| 213 | 514.98 | 6-[1-(4-chloro-3,5-diethoxy-benzyl)-piperidin-4-ylamino]-N-(2,2,2-trifluoro-ethyl)-nicotinamide | 6-[1-(4-chloro-3,5-diethoxy-benzyl)-piperidin-4-ylamino]-nicotinic acid (example 70) and 2,2,2-trifluoro-ethylamine (commercially available) | 515.4 |
| 214 | 518.06 | N-(2-acetylamino-ethyl)-6-[1-(4-chloro-3,5-diethoxy-benzyl)-piperidin-4-ylamino]-nicotinamide | 6-[1-(4-chloro-3,5-diethoxy-benzyl)-piperidin-4-ylamino]-nicotinic acid (example 70) and N-(2-amino-ethyl)-acetamide (commercially available) | 518.5 |
| 215 | 544.10 | 1-{6-[1-(4-chloro-3,5-diethoxy-benzyl)-piperidin-4-ylamino]-pyridine-3-carbonyl}-piperidine-4-carboxylic acid amide | 6-[1-(4-chloro-3,5-diethoxy-benzyl)-piperidin-4-ylamino]-nicotinic acid (example 70) and piperidine-4-carboxylic acid amide (commercially available) | 544.4 |
| 216 | 544.10 | 1-(4-{6-[1-(4-chloro-3,5-diethoxy-benzyl)-piperidin-4-ylamino]-pyridine-3-carbonyl}-piperazin-1-yl)-ethanone | 6-[1-(4-chloro-3,5-diethoxy-benzyl)-piperidin-4-ylamino]-nicotinic acid (example 70) and 1-piperazin-1-yl-ethanone (commercially available) | 544.4 |
| 217 | 545.08 | 1-{6-[1-(4-chloro-3,5-diethoxy-benzyl)-piperidin-4-ylamino]-pyridine-3-carbonyl}-piperidine-4-carboxylic acid | 6-[1-(4-chloro-3,5-diethoxy-benzyl)-piperidin-4-ylamino]-nicotinic acid (example 70) and piperidine-4-carboxylic acid (commercially available) | 545.4 |

Example 218

(3-Chloro-isoquinolin-1-yl)-[1-(2,6-diethoxy-4'-fluoro-biphenyl-4-ylmethyl)-piperidin-4-yl]-amine

Step 1: 2,6-Diethoxy-4'-fluoro-biphenyl-4-carbaldehyde (Intermediate E22)

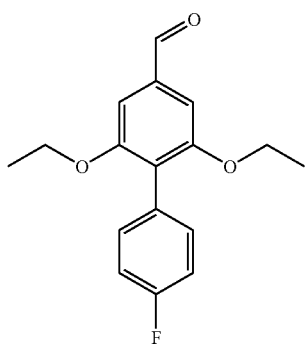

3,5-Diethoxy-4-iodo-benzaldehyde (14.05 g, 43.89 mmol, 1.0 equiv; intermediate E13) was dissolved under Ar in toluene (180 mL) and water (20 mL) and treated successively with 4-fluorophenyl boronic acid (12.28 g, 87.78 mmol, 2.0 equiv), $K_3PO_4$ (50.12 g, 236.12 mmol, 5.38 equiv), tricyclohexylphosphine (2.80 g, 9.66 mmol, 0.22 equiv), and palladium(II) acetate (1.08 g, 4.83 mmol, 0.11 equiv). The reaction mixture was heated to 100° C. for 18 h under scrupulous exclusion of oxygen, when GC indicated the absence of starting iodo-compound. The reaction mixture was poured on crashed ice/$NH_4Cl$, extracted with ethyl acetate (2×200 mL) and the combined organic phases washed with a sat. solution of NaCl (2×100 mL) and water (2×100 mL). The organic phase was dried over $Na_2SO_4$, concentrated by evaporation under reduced pressure and the crude material purified by silica column chromatography eluting with a mixture of hexane/ethyl acetate (9:1). Recrystallization from hexane/ethyl acetate provided 10.44 g (83%) of the title compound as white crystals. MS (EI): 288.2 [M]+.

Step 2: (3-Chloro-isoquinolin-1-yl)-[1-(2,6-diethoxy-4'-fluoro-biphenyl-4-ylmethyl)-piperidin-4-yl]-amine The title compound was prepared in analogy to the synthesis of 6-[1-(3-ethoxy-4-methyl-benzyl)-piperidin-4-ylamino]-nicotinonitrile (example 38/step 3) from (3-chloro-isoquinolin-1-yl)-piperidin-4-yl-amine dihydrochloride (intermediate B13) and 2,6-diethoxy-4'-fluoro-biphenyl-4-carbaldehyde (intermediate E22) in a yield of 8.9 mg (11%). MS (ISP): 534.5 [M+H]+.

Example 219

5-[1-(2,6-Diethoxy-4'-fluoro-biphenyl-4-ylmethyl)-piperidin-4-ylamino]-pyrazine-2-carboxylic acid methyl ester The title compound was prepared in analogy to the synthesis of 6-[1-(3-ethoxy-4-methyl-benzyl)-piperidin-4-ylamino]-nicotinonitrile (example 38/step 3) from 5-(piperidin-4-ylamino)-pyrazine-2-carboxylic acid methyl ester dihydrochloride (intermediate B14) and 2,6-diethoxy-4'-fluoro-biphenyl-4-carbaldehyde (intermediate E22) in a yield of 5.8 mg (7%). MS (ISP): 509.4 [M+H]+.

The pyridine piperidine intermediates B16 to B21 were prepared following literature precedents or as described below.

Synthesis of Pyridine Piperidine Intermediates B16 to B21 to be Used in Table 6

Intermediate B16

(5-Methanesulfonyl-pyridin-2-yl)-piperidin-4-yl-amine

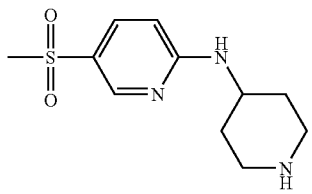

Step 1: 4-(5-Methanesulfonyl-pyridin-2-ylamino)-piperidine-1-carboxylic acid tert-butyl ester To a stirred solution of 2-bromo-5-methanesulfonyl-pyridine (0.24 g, 1.0 mmol, 1.0 equiv; prepared as described in EP 1298 116 A1 (Pfizer Products Inc., USA)) and 4-amino-piperidine-1-carboxylic acid tert-butyl ester (0.23 g, 1.1 mmol, 1.1 equiv) in acetonitrile (6.0 mL) was added N-ethyl diisopropylamine (0.87 mL, 0.66 g, 5.0 mmol, 5.0 equiv) drop by drop at rt and the reaction mixture heated to reflux for 19 h. The reaction mixture was poured into crashed ice and extracted twice with ethyl acetate. The combined organic layers were washed with brine and water, dried over MgSO4, filtered and concentrated by evaporation under reduced pressure. The crude product was purified by column chromatography on silica eluting with a gradient of dichloromethane/methanol to give 0.25 g (70%) of the title compound as light brown oil. MS (ISP): 356.1 [M+H]+.

Step 2: (5-Methanesulfonyl-pyridin-2-yl)-piperidin-4-yl-amine

To a stirred solution of 4-(5-methanesulfonyl-pyridin-2-ylamino)-piperidine-1-carboxylic acid tert-butyl ester (1.00 g, 2.8 mmol, 1.0 equiv) in ethanol (18 mL) was added 4 M HCl in dioxane (3.52 mL, 14.1 mmol, 5.0 equiv) drop by drop and the reaction mixture stirred at 50° C. for 2 h. It was then cooled down to rt, poured into ice water and the pH adjusted to 9-10 by addition of a sat. solution of potassium carbonate. The solution was extracted six times with a mixture of dichloromethane/isopropanol (4:1). The combined organic layers were concentrated by evaporation under reduced pressure and the crude product was purified by crystallization from heptane to give 0.53 g (74%) of the title compound as colorless solid. MS (ISP): 256.2 [M+H]+.

Intermediate B17

2-Chloro-6-(piperidin-4-ylamino)-isonicotinic acid methyl ester

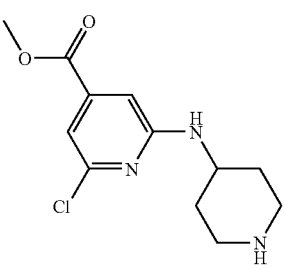

Step 1: 2-(1-tert-Butoxycarbonyl-piperidin-4-ylamino)-6-chloro-isonicotinic acid methyl ester A stirred suspension of 2,6-dichloro-isonicotinic acid methyl ester (4.52 g, 21.9 mmol 1.0 equiv), 4-amino-piperidine-1-carboxylic acid tert-butyl ester (4.39 g, 21.9 mmol, 1.0 equiv), palladium(II) acetate (0.50 g, 2.2 mmol, 0.1 equiv) and rac-2,2'-bis(diphenylphosphino)-1,1'-binaphthalene (1.39 g, 2.2 mmol, 0.1 equiv) in toluene (150 mL) was treated at rt with caesium carbonate (9.39 g, 28.5 mmol, 1.3 equiv) and then warmed to 80° C. After 6 h, the reaction mixture was poured into crashed ice and extracted twice with ethyl acetate. The combined organic layers were washed with brine and water, dried over MgSO4, filtered and concentrated by evaporation under reduced pressure. The crude product was purified by column chromatography on silica eluting with a gradient of dichloromethane/methanol to give 5.40 g (67%) of the title compound as a light yellow solid. MS (ISP): 370.1 [M+H]+.

Step 2: 2-Chloro-6-(piperidin-4-ylamino)-isonicotinic acid methyl ester

The title compound was prepared in analogy to the synthesis of (5-methanesulfonyl-pyridin-2-yl)-piperidin-4-yl-amine (intermediate B16/step 2) from 2-(1-tert-butoxycarbonyl-piperidin-4-ylamino)-6-chloro-isonicotinic acid methyl ester by cleavage of the BOC group with 4 M HCl in dioxane and ethanol at rt. MS (ISP): 270.1 [M+H]$^+$.

Intermediate B18

[6-(Piperidin-4-ylamino)-pyridin-3-yloxy]-acetonitrile

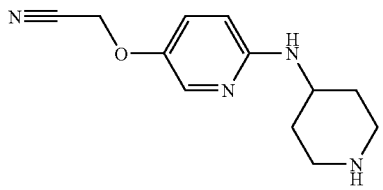

Step 1: 4-(5-Benzyloxy-pyridin-2-ylamino)-piperidine-1-carboxylic acid tert-butyl ester A stirred suspension of 5-benzyloxy-2-chloro-pyridine (12.4 g, 56.4 mmol, 1.0 equiv; prepared as described in WO 9728 128 A1 (Zeneca Ltd., UK)), 4-amino-piperidine-1-carboxylic acid tert-butyl ester (11.31 g, 56.4 mmol, 1.0 equiv), palladium(II) acetate (0.51 g, 2.3 mmol, 0.04 equiv) and rac-2,2'-bis(diphenylphosphino)-1,1'-binaphthalene (1.44 g, 2.3 mmol, 0.04 equiv) in toluene (250 mL) was treated at rt with KOtert-Bu (6.71 g, 67.7 mmol, 1.2 equiv) and subsequently warmed to 70° C. After 7 h, the reaction mixture was poured into crashed ice and filtered over dicalite and extracted twice with toluene. The combined organic layers were dried over MgSO$_4$, filtered and concentrated by evaporation under reduced pressure. The crude product was purified by column chromatography on silica eluting with a gradient of dichloromethane/methanol to give 18.73 g (87%) of the title compound as a light yellow solid. MS (ISP): 384.1 [M+H]$^+$.

Step 2: 4-(5-Hydroxy-pyridin-2-ylamino)-piperidine-1-carboxylic acid tert-butyl ester To a solution of 4-(5-benzyloxy-pyridin-2-ylamino)-piperidine-1-carboxylic acid tert-butyl ester (18.2 g, 47.5 mmol, 1.0 equiv) in methanol (200 mL) was added 10% Pd on activated carbon (2.53 g, 2.38 mmol 0.05 equiv) under an atmosphere of Ar. The reaction vessel was twice evacuated and ventilated with hydrogen gas and the well stirred reaction mixture was subsequently hydrogenated at rt and 1 bar H$_2$ for 3 h. After filtration over dicalite the crude reaction mixture was concentrated by evaporation under reduced pressure and purified by column chromatography on silica eluting with a gradient of dichloromethane/methanol to give 10.50 g (75%) of the title compound as a light yellow solid. MS (ISP): 294.2 [M+H]$^+$.

Step 3: 4-(5-tert-Butoxycarbonyloxy-pyridin-2-ylamino)-piperidine-1-carboxylic acid tert-butyl ester To a mechanically stirred suspension of 4-(5-hydroxy-pyridin-2-ylamino)-piperidine-1-carboxylic acid tert-butyl ester (9.86 g, 33.6 mmol, 1.0 equiv) and sodium bicarbonate (28.52 g, 33.6 mmol, 1.0 equiv) in a mixture of water and dioxane (1:1) (500 mL) at rt was added di-tert-butyl-dicarbonate (37.43 g, 168 mmol, 5.0 equiv) in several small portions and the mixture stirred for 24 h. The heterogeneous reaction mixture was subsequently poured into cold water, carefully acidified with 25% HCl to adjust the pH to around 3 and extracted twice with ethyl acetate. The combined organic layers were washed with brine and water, dried over MgSO$_4$, filtered and concentrated by evaporation under reduced pressure. The crude product was purified by column chromatography on silica eluting with a gradient of dichloromethane/methanol to give 13.64 g (100%) of the title compound as a light yellow solid. MS (ISP): 394.2 [M+H]$^+$.

Step 4: 4-[tert-Butoxycarbonyl-(5-tert-butoxycarbonyloxy-pyridin-2-yl)-amino]-piperidine-1-carboxylic acid tert-butyl ester To a well stirred suspension of 4-(5-tert-butoxycarbonyloxy-pyridin-2-ylamino)-piperidine-1-carboxylic acid tert-butyl ester (9.58 g, 24.3 mmol, 1.0 equiv) and N,N-dimethylpyridin-4-yl-amine (1.52 g, 12.2 mmol, 0.5 equiv) in acetonitrile (200 mL) at rt was added di-tert-butyl-dicarbonate (23.86 g, 107 mmol, 4.4 equiv) in several small portions and stirring continued for 44 h. The reaction mixture was then poured into cold water and extracted twice with ethyl acetate. The combined organic layers were washed with brine and water, dried over MgSO$_4$, filtered and concentrated by evaporation under reduced pressure. The crude product was purified by column chromatography on silica eluting with a gradient of heptane/ethyl acetate to give 6.17 g (51%) of the title compound as yellow solid. MS (ISP): 494.3 [M+H]$^+$.

Step 5: 4-[tert-Butoxycarbonyl-(5-hydroxy-pyridin-2-yl)-amino]-piperidine-1-carboxylic acid tert-butyl ester To a solution of 4-[tert-butoxycarbonyl-(5-tert-butoxycarbonyloxy-pyridin-2-yl)-amino]-piperidine-1-carboxylic acid tert-butyl ester (6.75 g, 13.7 mmol, 1.0 equiv) in a mixture of THF/methanol (1:1) (100 mL) at 3° C. was added drop by drop a solution of 1 M LiOH (34.2 mL, 34.5 mmol, 2.5 equiv) and after the addition was completed the mixture warmed up to rt. After 18 h, the reaction mixture was poured into cold water and extracted three times with dichloromethane. The combined organic layers were washed with brine and water, dried over MgSO$_4$, filtered and concentrated by evaporation under reduced pressure. The crude product was purified by column chromatography on silica eluting with a gradient of dichloromethane/methanol to give 4.31 g (80%) of the title compound as orange foam. MS (ISP): =394.1 [M+H]$^+$.

Step 6: 4-[tert-Butoxycarbonyl-(5-cyanomethoxy-pyridin-2-yl)-amino]-piperidine-1-carboxylic acid tert-butyl ester To a stirred solution of 4-[tert-butoxycarbonyl-(5-hydroxy-pyridin-2-yl)-amino]-piperidine-1-carboxylic acid tert-butyl ester (0.79 g, 2.0 mmol, 1.0 equiv) in acetonitrile (20 mL) was added potassium carbonate (0.84 g, 6.0 mmol, 3.0 equiv), followed by bromoacetonitrile (0.21 mL, 0.37 g, 3.0 mmol, 1.5 equiv). After stirring at rt for 16 h, the reaction mixture was poured into ice water and extracted twice with ethyl acetate. The combined organic layers were washed with water, dried over MgSO$_4$, filtered and concentrated by evaporation under reduced pressure. The crude product was purified by column chromatography on silica eluting with a gradient of dichloromethane/methanol to give 0.93 g (100%) of the title compound as light brown oil. MS (ISP): 433.3 [M+H]$^+$.

Step 7: [6-(Piperidin-4-ylamino)-pyridin-3-yloxy]-acetonitrile

To a stirred solution of 4-[tert-butoxycarbonyl-(5-cyanomethoxy-pyridin-2-yl)-amino]-piperidine-1-carboxylic acid tert-butyl ester (0.90 g, 2.1 mmol, 1.0 equiv) in dichloromethane (15 mL) was added 90% trifluoroacetic acid (1.69 mL, 2.37 g, 19 mmol, 9.0 equiv) drop by drop and the reaction mixture stirred at rt for 16 h. It was then poured into ice water and the pH adjusted to 9-10 by addition of a sat. solution of potassium carbonate. The solution was extracted three times with a mixture of dichloromethane/isopropanol (4:1). The combined organic layers were concentrated by evaporation under reduced pressure to give 0.15 g (30%) of the title compound as yellow oil. MS (ISP): 233.0 [M+H]$^+$.

Intermediate B19 rac-3-[6-(Piperidin-4-ylamino)-pyridin-3-yloxy]-propane-1,2-diol

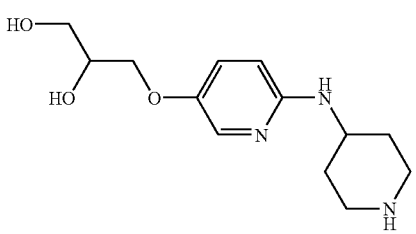

Step 1: rac-4-{tert-Butoxycarbonyl-[5-(2,2-dimethyl-[1,3]dioxolan-4-ylmethoxy)-pyridin-2-yl]amino}-piperidine-1-carboxylic acid tert-butyl ester To a stirred solution of 4-[tert-butoxycarbonyl-(5-hydroxy-pyridin-2-yl)-amino]-piperidine-1-carboxylic acid tert-butyl ester (intermediate B18/step 5) (0.79 g, 2.0 mmol, 1.0 equiv) in DMF (20 mL) was added potassium carbonate (0.62 g, 4.4 mmol, 2.2 equiv), followed by rac-toluene-4-sulfonic acid 2,2-dimethyl-[1,3]dioxolan-4-ylmethyl ester (0.65 g, 2.2 mmol, 1.1 equiv; commercially available). The reaction mixture was heated to 100° C. for 16 h and then poured into ice water and extracted twice with ether. The combined organic layers were washed with water, dried over MgSO$_4$, filtered and concentrated by evaporation under reduced pressure. The crude product was purified by column chromatography on silica eluting with a gradient of dichloromethane/methanol to give 0.99 g (97%) of the title compound as light yellow oil. MS (ISP): 508.3 [M+H]$^+$.

Step 2: rac-3-[6-(Piperidin-4-ylamino)-pyridin-3-yloxy]-propane-1,2-diol

The title compound was prepared in analogy to the procedure described for (5-methanesulfonyl-pyridin-2-yl)-piperidin-4-yl-amine (intermediate B16/step 2) from rac-4-{tert-butoxycarbonyl-[5-(2,2-dimethyl-[1,3]dioxolan-4-ylmethoxy)-pyridin-2-yl]-amino}-piperidine-1-carboxylic acid tert-butyl ester by cleavage of both the BOC and the isopropylidene group with 4 M HCl in dioxane and ethanol at rt followed by ion exchange chromatography on Q-Sepharose Fast Flow. MS (ISP): 268.2 [M+H]$^+$.

Intermediate B20

3-[6-(Piperidin-4-ylamino)-pyridin-3-yloxy]-propan-1-ol

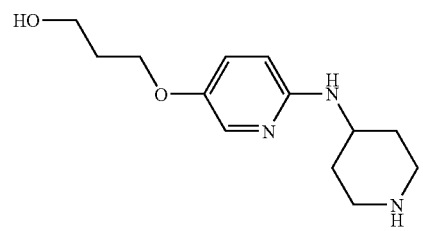

The title compound was prepared in analogy to the procedure described for rac-4-{tert-butoxycarbonyl-[5-(2,2-dimethyl-[1,3]dioxolan-4-ylmethoxy)-pyridin-2-yl]-amino}-piperidine-1-carboxylic acid tert-butyl ester (intermediate B19/step 1) from 4-[tert-butoxycarbonyl-(5-hydroxy-pyridin-2-yl)-amino]-piperidine-1-carboxylic acid tert-butyl ester (intermediate B18/step 5) by reaction with rac-2-(3-bromopropoxy)-tetrahydro-2H-pyran (commercially available) and potassium carbonate in DMF at rt, followed by BOC and THP cleavage with 4 M HCl in dioxane and ethanol at 70° C. in analogy to the synthesis of (5-methanesulfonyl-pyridin-2-yl)-piperidin-4-yl-amine (intermediate B16/step 2). MS (ISP): 252.1 [M+H]$^+$.

Intermediate B21

Methanesulfonic acid 6-(piperidin-4-ylamino)-pyridin-3-yl ester

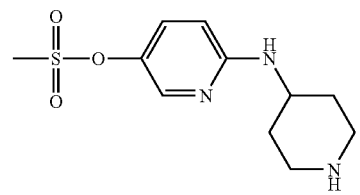

Step 1: 4-[tert-Butoxycarbonyl-(5-methanesulfonyloxy-pyridin-2-yl)-amino]-piperidine-1-carboxylic acid tert-butyl ester To a stirred solution of 4-[tert-butoxycarbonyl-(5-hydroxy-pyridin-2-yl)-amino]-piperidine-1-carboxylic acid tert-butyl ester (0.60 g, 1.5 mmol, 1.0 equiv; intermediate B18/step 5) and potassium carbonate (0.64 g, 4.6 mmol, 3.1 equiv) in DMF (15 mL) was added slowly methanesulfonyl chloride (0.18 mL, 0.27 g, 2.3 mmol, 1.5 equiv). After stirring at rt for 20 h, the reaction mixture was poured into ice water and extracted twice with diethyl ether. The combined organic layers were washed with water, dried over MgSO$_4$, filtered and concentrated by evaporation under reduced pressure. The crude product was purified by column chromatography on silica eluting with a gradient of dichloromethane/methanol to give 0.39 g (55%) of the title compound as light brown solid. MS (ISP): 472.2 [M+H]$^+$.

Step 2: Methanesulfonic acid 6-(piperidin-4-ylamino)-pyridin-3-yl ester

The title compound was prepared in analogy to the procedure described for (5-methanesulfonyl-pyridin-2-yl)-piperidin-4-yl-amine (intermediate B16/step 2) from 4-[tert-butoxycarbonyl-(5-methanesulfonyloxy-pyridin-2-yl)-amino]-piperidine-1-carboxylic acid tert-butyl ester by cleavage of the BOC group with 4 M HCl in dioxane and ethanol at 70° C. MS (ISP): 272.1 [M+H]$^+$.

Example 220

[1-(3,5-Diethoxy-4-fluoro-benzyl)-piperidin-4-yl]-(5-methanesulfonyl-pyridin-2-yl)-amine To a solution of (5-methanesulfonyl-pyridin-2-yl)-piperidin-4-yl-amine (0.12 g, 0.5 mmol, 1.0 equiv; intermediate B16) and 3,5-diethoxy-4-fluoro-benzaldehyde (0.11 g, 0.5 mmol, 1.0 equiv; intermediate E5) in ethanol (5 mL) under an atmosphere of Ar was added N-ethyl diisopropylamine (0.19 mL, 0.15 g, 1.2 mmol, 2.3 equiv) and glacial acetic acid (0.05 mL, 0.06 g, 1.0 mmol, 2.0 equiv) and the mixture heated to 50° C. for 2 h. After cooling down to 35° C., sodium cyanoborohydride (0.16 g, 2.5 mmol, 5.1 equiv) was added and the reaction mixture heated again to 50° C. for 1.5 h. It was then poured into crashed ice, the pH of the water phase adjusted to ~10 by addition of a sat. solution of sodium carbonate and the mixture extracted twice with dichloromethane. The combined organic phases were washed with water, dried over MgSO$_4$, filtered and concentrated by evaporation under reduced pressure. The crude product was purified by column chromatography on silica eluting with a gradient of dichloromethane/methanol to give 0.16 g (71%) of the title compound as colorless foam. MS (ISP): 452.1 [M+H]$^+$.

Examples 221 to 231

According to the procedure described for the synthesis of example 220 further pyridine derivatives have been synthesized from (5-methanesulfonyl-pyridin-2-yl)-piperidin-4-yl-amine (intermediate B16), 2-chloro-6-(piperidin-4-ylamino)-isonicotinic acid methyl ester (intermediate B17), [6-(piperidin-4-ylamino)-pyridin-3-yloxy]-acetonitrile (intermediate B18), rac-3-[6-(piperidin-4-ylamino)-pyridin-3-yloxy]-propane-1,2-diol (intermediate B19), 3-[6-(piperidin-4-ylamino)-pyridin-3-yloxy]-propan-1-ol (intermediate B20) and methanesulfonic acid 6-(piperidin-4-ylamino)-pyridin-3-yl ester (intermediate B21) and the respective benzaldehyde intermediates as indicated in Table 6. The results are compiled in Table 6 and comprise example 221 to example 231.

TABLE 6

| No. | MW | Compound Name | Starting Materials | ISP [M + H]$^+$ found |
|---|---|---|---|---|
| 221 | 468.02 | [1-(4-chloro-3,5-diethoxy-benzyl)-piperidin-4-yl]-(5-methanesulfonyl-pyridin-2-yl)-amine | (5-methanesulfonyl-pyridin-2-yl)-piperidin-4-yl-amine (intermediate B16) and 4-chloro-3,5-diethoxy-benzaldehyde (intermediate E6) | [M + H]$^+$ 468.1 |
| 222 | 527.66 | [1-(2,6-diethoxy-4'-fluoro-biphenyl-4-ylmethyl)-piperidin-4-yl]-(5-methanesulfonyl-pyridin-2-yl)-amine | (5-methanesulfonyl-pyridin-2-yl)-piperidin-4-yl-amine (intermediate B16) and 2,6-diethoxy-4'-fluoro-biphenyl-4-carbaldehyde (intermediate E22) | [M + H]$^+$ 528.2 |
| 223 | 465.95 | 2-chloro-6-[1-(3,5-diethoxy-4-fluoro-benzyl)-piperidin-4-ylamino]-isonicotinic acid methyl ester | 2-chloro-6-(piperidin-4-ylamino)-isonicotinic acid methyl ester (intermediate B17) and 3,5-diethoxy-4-fluoro-benzaldehyde (intermediate E5) | [M + H]$^+$ 466.2 |
| 224 | 482.41 | 2-chloro-6-[1-(4-chloro-3,5-diethoxy-benzyl)-piperidin-4-ylamino]-isonicotinic acid methyl ester | 2-chloro-6-(piperidin-4-ylamino)-isonicotinic acid methyl ester (intermediate B17) and 4-chloro-3,5-diethoxy-benzaldehyde (intermediate E6) | [M + H]$^+$ 482.2 |
| 225 | 542.05 | 2-chloro-6-[1-(2,6-diethoxy-4'-fluoro-biphenyl-4-ylmethyl)-piperidin-4-ylamino]-isonicotinic acid methyl ester | 2-chloro-6-(piperidin-4-ylamino)-isonicotinic acid methyl ester (intermediate B17) and 2,6-diethoxy-4'-fluoro-biphenyl-4-carbaldehyde (intermediate E22) | [M + H]$^+$ 542.2 |
| 226 | 504.60 | {6-[1-(2,6-diethoxy-4'-fluoro-biphenyl-4-ylmethyl)-piperidin-4-ylamino]-pyridin-3-yloxy}-acetonitrile | [6-(piperidin-4-ylamino)-pyridin-3-yloxy]-acetonitrile (intermediate B18) and 2,6-diethoxy-4'-fluoro-biphenyl-4-carbaldehyde (intermediate E22) | [M + H]$^+$ 505.3 |
| 227 | 480.00 | rac-3-{6-[1-(4-chloro-3,5-diethoxy-benzyl)- | rac-3-[6-(piperidin-4-ylamino)-pyridin-3-yloxy]- | [M + H]$^+$ 480.1 |

TABLE 6-continued

| No. | MW | Compound Name | Starting Materials | ISP [M + H]+ found |
|---|---|---|---|---|
| | | piperidin-4-ylamino]-pyridin-3-yloxy}-propane-1,2-diol | propane-1,2-diol (intermediate B19) and 4-chloro-3,5-diethoxy-benzaldehyde (intermediate E6) | |
| 228 | 539.64 | rac-3-{6-[1-(2,6-diethoxy-4'-fluoro-biphenyl-4-ylmethyl)-piperidin-4-ylamino]-pyridin-3-yloxy}-propane-1,2-diol | rac-3-[6-(piperidin-4-ylamino)-pyridin-3-yloxy]-propane-1,2-diol (intermediate B19) and 2,6-diethoxy-4'-fluoro-biphenyl-4-carbaldehyde (intermediate E22) | [M + H]+ 540.3 |
| 229 | 523.65 | 3-{6-[1-(2,6-diethoxy-4'-fluoro-biphenyl-4-ylmethyl)-piperidin-4-ylamino]-pyridin-3-yloxy}-propan-1-ol | 3-[6-(piperidin-4-ylamino)-pyridin-3-yloxy]-propan-1-ol (intermediate B20) and 2,6-diethoxy-4'-fluoro-biphenyl-4-carbaldehyde (intermediate E22) | [M + H]+ 524.2 |
| 230 | 464.00 | 3-{6-[1-(4-chloro-3,5-diethoxy-benzyl)-piperidin-4-ylamino]-pyridin-3-yloxy}-propan-1-ol | 3-[6-(piperidin-4-ylamino)-pyridin-3-yloxy]-propan-1-ol (intermediate B20) and 4-chloro-3,5-diethoxy-benzaldehyde (intermediate E6) | [M + H]+ 464.2 |
| 231 | 543.66 | methanesulfonic acid 6-[1-(2,6-diethoxy-4'-fluoro-biphenyl-4-ylmethyl)-piperidin-4-ylamino]-pyridin-3-yl ester | methanesulfonic acid 6-(piperidin-4-ylamino)-pyridin-3-yl ester (intermediate B21) and 2,6-diethoxy-4'-fluoro-biphenyl-4-carbaldehyde (intermediate E22) | [M + H]+ 544.3 |

Example 232

2-Chloro-6-[1-(4-chloro-3,5-diethoxy-benzyl)-piperidin-4-ylamino]-isonicotinic acid To a stirred solution of 2-chloro-6-[1-(4-chloro-3,5-diethoxy-benzyl)-piperidin-4-ylamino]-isonicotinic acid methyl ester (0.17 g, 0.35 mmol, 1.0 equiv; example 224) in THF/methanol (2:1) (15 mL) was added a solution of 1 M LiOH (0.87 mL, 0.87 mmol. 2.5 equiv) drop by drop. After 16 h, the reaction mixture was poured into ice water, the pH of the water phase adjusted to 3-4 with diluted HCl and the mixture extracted twice with dichloromethane. The organic phases were washed with water, dried over $MgSO_4$, filtered and concentrated by evaporation under reduced pressure. The crude product was purified by column chromatography on silica eluting with a gradient of dichloromethane/methanol to give 0.12 g (73%) of the title compound as colorless solid. MS (ISP): 468.3 [M+H]+.

Example 233

2-Chloro-6-[1-(2,6-diethoxy-4'-fluoro-biphenyl-4-ylmethyl)-piperidin-4-ylamino]-isonicotinic acid The title compound was prepared in analogy to the procedure described for 2-chloro-6-[1-(4-chloro-3,5-diethoxy-benzyl)-piperidin-4-ylamino]-isonicotinic acid (example 232) from 2-chloro-6-[1-(2,6-diethoxy-4'-fluoro-biphenyl-4-ylmethyl)-piperidin-4-ylamino]-isonicotinic acid methyl ester (example 225) and obtained as colorless solid. MS (ISN): 526.1 [M−H]−.

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims.

The invention claimed is:

1. A compound of formula (I):

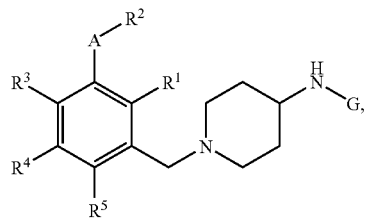

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, halogen-$C_{1-7}$-alkoxy, —C(O)OR$^6$, wherein $R^6$ is $C_{1-7}$-alkyl, amino, pyrrolyl, unsubstituted phenyl or phenyl substituted by one to three groups independently selected from $C_{1-7}$-alkyl, halogen and $C_{1-7}$-alkoxy;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—C(CH$_3$)$_2$—CH═CH—;

$R^5$ is selected from the group consisting of hydrogen, halogen and $C_{1-7}$-alkoxy;

G is selected from the groups

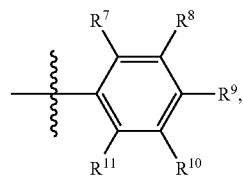

-continued

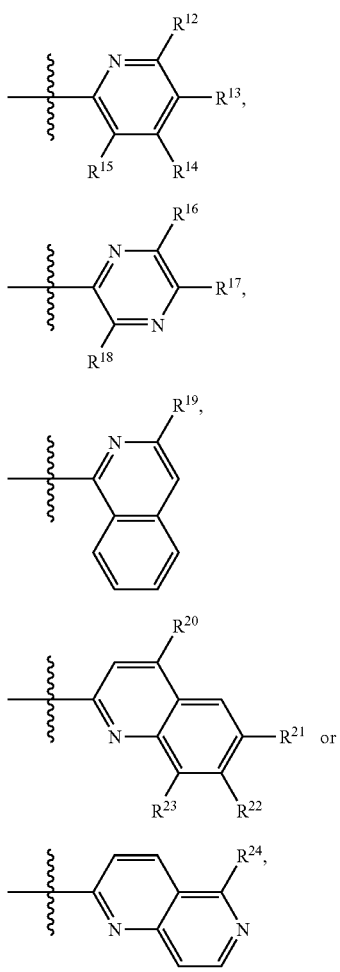

wherein
R⁷ and R¹¹ are hydrogen;
R⁸ and R¹⁰ independently from each other are hydrogen or —NH—C(O)—R²⁵, wherein R²⁵ is $C_{1-7}$-alkyl;
R⁹ is selected from the group consisting of hydrogen, $C_{1-7}$-alkyl, halogen, halogen-$C_{1-7}$-alkyl, cyano, —C(O)OR²⁶, wherein R²⁶ is hydrogen or $C_{1-7}$-alkyl, —(CH₂)$_m$—S(O)₂—NH—R²⁷, wherein m is 0 or 1 and R²⁷ is selected from $C_{1-7}$-alkyl, unsubstituted heteroaryl and heteroaryl substituted by $C_{1-7}$-alkyl; and —NH—S(O)₂—R²⁸, wherein R²⁸ is $C_{1-7}$-alkyl;
or R⁸ and R⁹ are bonded to each other to form a ring together with the carbon atoms they are attached to and R⁸ and R⁹ together are —CH₂—S(O)₂—CH₂—;
R¹² is selected from the group consisting of hydrogen, $C_{1-7}$-alkyl, halogen and amino;
R¹³ is selected from the group consisting of hydrogen, $C_{1-7}$-alkyl, halogen, halogen-$C_{1-7}$-alkyl, cyano, nitro, phenyl, tetrazolyl, benzoimidazolyl, —COOR²⁹, wherein R²⁹ is hydrogen or $C_{1-7}$-alkyl, hydroxy-$C_{1-7}$-alkoxy, cyano-$C_{1-7}$-alkoxy, —CONHR³⁰, wherein R³⁰ is selected from the group consisting of hydrogen, $C_{1-7}$-alkyl, $C_{3-7}$-cycloalkyl, hydroxy-$C_{1-7}$-alkyl, $C_{1-7}$-alkoxy-$C_{1-7}$-alkyl, halogen-$C_{1-7}$-alkyl, carboxy-$C_{1-7}$-alkyl, —(CH₂)$_n$—NH—C(O)—R³¹, wherein n is 1 or 2 and R³¹ is $C_{1-7}$-alkyl, —S(O)₂—R³³, wherein R³³ is $C_{1-7}$-alkyl, —O—S(O)₂—R³⁴, wherein R³⁴ is $C_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and $C_{1-7}$-alkanoyl;
R¹⁴ is selected from the group consisting of hydrogen, $C_{1-7}$-alkyl, $C_{1-7}$-alkoxy, $C_{1-7}$-alkoxy-$C_{1-7}$-alkyl, cyano, carbamoyl, —COOR³⁵, wherein R³⁵ is hydrogen or $C_{1-7}$-alkyl, halogen and halogen-$C_{1-7}$-alkyl;
R¹⁵ is selected from the group consisting of hydrogen, cyano, halogen and halogen-$C_{1-7}$-alkyl;
R¹⁶ and R¹⁸ are hydrogen;
R¹⁷ is carbamoyl or —COOR³², wherein R³² is hydrogen or $C_{1-7}$-alkyl;
R¹⁹ is hydrogen or halogen;
R²⁰ is selected from the group consisting of hydrogen, $C_{1-7}$-alkyl, $C_{1-7}$-alkoxy, $C_{1-7}$-alkoxy-$C_{1-7}$-alkyl and halogen;
R²¹, R²² and R²³ independently from each other are hydrogen or halogen;
R²⁴ is hydrogen or $C_{1-7}$-alkyl;
and pharmaceutically acceptable salts thereof.

2. The compound according to claim 1, wherein A is O.
3. The compound according to claim 1, wherein R¹ is hydrogen.
4. The compound according to claim 1, wherein R² is selected from the group consisting of $C_{2-7}$-alkyl, $C_{2-7}$-alkenyl and halogen-$C_{1-7}$-alkyl.
5. The compound according to claim 1, wherein R² is selected from the group consisting of ethyl, propyl, isopropyl, allyl, 2-fluoroethyl, butyl and isobutyl.
6. The compound according to claim 1, wherein R³ is selected from the group consisting of hydrogen, $C_{1-7}$-alkyl, hydroxy, $C_{1-7}$-alkoxy, halogen, halogen-$C_{1-7}$-alkoxy, —C(O)OR⁶, wherein R⁶ is $C_{1-7}$-alkyl, amino and pyrrolyl.
7. The compound according to claim 1, wherein R³ is selected from the group consisting of hydrogen, $C_{1-7}$-alkoxy and halogen.
8. The compound according to claim 1, wherein R³ is halogen.
9. The compound according to claim 1, wherein R⁴ is selected from the group consisting of hydrogen, hydroxy, $C_{1-7}$-alkoxy and $C_{1-7}$-alkoxy-$C_{1-7}$-alkoxy.
10. The compound according to claim 1, wherein R⁵ is hydrogen.
11. The compound according to claim 1, wherein G is

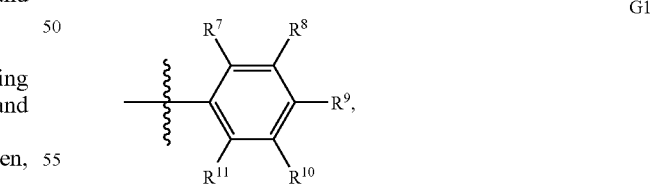

and wherein
R⁷ and R¹¹ are hydrogen;
R⁸ and R¹⁰ independently from each other are hydrogen or —NH—C(O)—R²⁵, wherein R²⁵ is $C_{1-7}$-alkyl; and
R⁹ is selected from the group consisting of hydrogen, $C_{1-7}$-alkyl, halogen, halogen-$C_{1-7}$-alkyl, cyano, —C(O)OR²⁶, wherein R²⁶ is hydrogen or $C_{1-7}$-alkyl, —(CH₂)$_m$—S(O)₂—NH—R²⁷, wherein m is 0 or 1 and R²⁷ is selected from $C_{1-7}$-alkyl, unsubstituted heteroaryl and heteroaryl substituted by $C_{1-7}$-alkyl; and —NH—S(O)₂—R²⁸, wherein R²⁸ is $C_{1-7}$-alkyl; or
R⁸ and R⁹ are bonded to each other to form a ring together with the carbon atoms they are attached to and R⁸ and R⁹ together are —CH₂—S(O)₂—CH₂—.

12. The compound according to claim 1, wherein
R⁷, R⁸, R¹⁰ and R¹¹ are hydrogen; and
R⁹ is selected from the group consisting of $C_{1-7}$-alkyl, halogen, halogen-$C_{1-7}$-alkyl, cyano, —C(O)OR²⁶, wherein R²⁶ is hydrogen or $C_{1-7}$-alkyl, —(CH₂)$_m$—S(O)₂—NH—R²⁷, wherein m is 0 or 1 and R²⁷ is selected from $C_{1-7}$-alkyl, unsubstituted heteroaryl and heteroaryl substituted by $C_{1-7}$-alkyl; and
—NH—S(O)₂—R²⁸, wherein R²⁸ is $C_{1-7}$-alkyl.

13. The compound according to claim 1, wherein G is

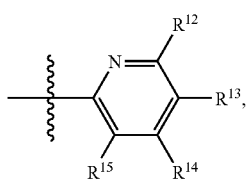

and wherein
R¹² is selected from the group consisting of hydrogen, $C_{1-7}$-alkyl, halogen and amino;
R¹³ is selected from the group consisting of hydrogen, $C_{1-7}$-alkyl, halogen, halogen-$C_{1-7}$-alkyl, cyano, nitro, phenyl, tetrazolyl, benzoimidazolyl, —COOR²⁹, wherein R²⁹ is hydrogen or $C_{1-7}$-alkyl, hydroxy-$C_{1-7}$-alkoxy, cyano-$C_{1-7}$-alkoxy, —CONHR³⁰, wherein R³⁰ is selected from the group consisting of hydrogen, $C_{1-7}$-alkyl, $C_{3-7}$-cycloalkyl, hydroxy-$C_{1-7}$-alkyl, $C_{1-7}$-alkoxy-$C_{1-7}$-alkyl, halogen-$C_{1-7}$-alkyl, carboxy-$C_{1-7}$-alkyl, —(CH₂)$_n$—NH—C(O)—R³¹, wherein n is 1 or 2 and R³¹ is $C_{1-7}$-alkyl, —S(O)₂—R³³, wherein R³³ is $C_{1-7}$-alkyl, —O—S(O)₂—R³⁴, wherein R³⁴ is $C_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and $C_{1-7}$-alkanoyl;
R¹⁴ is selected from the group consisting of hydrogen, $C_{1-7}$-alkyl, $C_{1-7}$-alkoxy, $C_{1-7}$-alkoxy-$C_{1-7}$-alkyl, cyano, carbamoyl, —COOR³⁵, wherein R³⁵ is hydrogen or $C_{1-7}$-alkyl, halogen and halogen-$C_{1-7}$-alkyl; and
R¹⁵ is selected from the group consisting of hydrogen, cyano, halogen and halogen-$C_{1-7}$-alkyl.

14. The compound according to claim 1, wherein
R¹², R¹⁴ and R¹⁵ are hydrogen; and
R¹³ is selected from the group consisting of $C_{1-7}$-alkyl, halogen, halogen-$C_{1-7}$-alkyl, cyano, nitro, phenyl, tetrazolyl, benzoimidazolyl, —COOR²⁹, wherein R²⁹ is hydrogen or $C_{1-7}$-alkyl, —CONHR³⁰, wherein R³⁰ is selected from the group consisting of hydrogen, $C_{1-7}$-alkyl, $C_{3-7}$-cycloalkyl, hydroxy-$C_{1-7}$-alkyl, $C_{1-7}$-alkoxy-$C_{1-7}$-alkyl, halogen-$C_{1-7}$-alkyl, carboxy-$C_{1-7}$-alkyl, —(CH₂)$_n$—NH—C(O)—R³¹, wherein n is 1 or 2 and R³¹ is $C_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and $C_{1-7}$-alkanoyl.

15. The compound according to claim 1, wherein G is

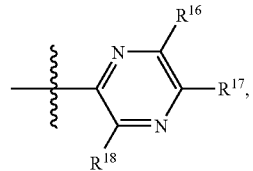

and wherein
R¹⁶ and R¹⁸ are hydrogen; and
R¹⁷ is carbamoyl or —COOR³², wherein R³² is hydrogen or $C_{1-7}$-alkyl.

16. The compound according to claim 1, wherein G is

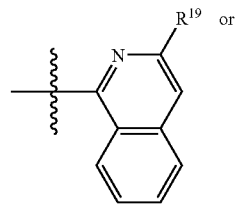

17. The compound according to claim 1, wherein G is

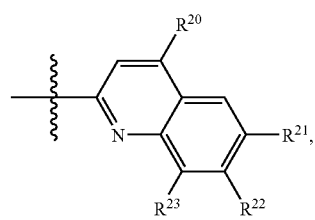

and wherein
R¹⁹ is hydrogen or halogen;
R²⁰ is selected from the group consisting of hydrogen, $C_{1-7}$-alkyl, $C_{1-7}$-alkoxy, $C_{1-7}$-alkoxy-$C_{1-7}$-alkyl and halogen; and
R²¹, R²² and R²³ independently from each other are hydrogen or halogen.

17. The compound according to claim 1, wherein G is

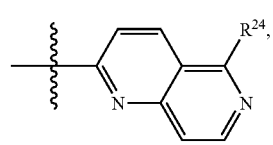

and wherein R²⁴ is hydrogen or $C_{1-7}$-alkyl.

18. The compound according to claim 1, having the formula

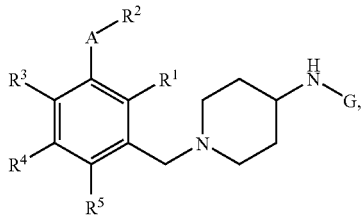

Ia wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, halogen-$C_{1-7}$-alkoxy, —C(O)OR$^6$, wherein $R^6$ is $C_{1-7}$-alkyl, amino and pyrrolyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—C(CH$_3$)$_2$—CH═CH—;

$R^5$ is selected from the group consisting of hydrogen, halogen and $C_{1-7}$-alkyl;

G is selected from the groups

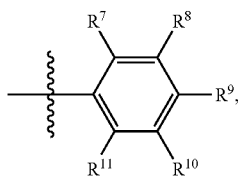

G1

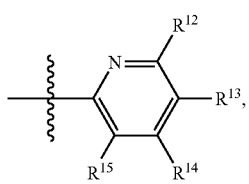

G2

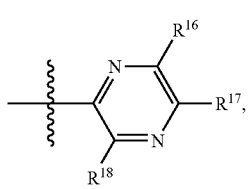

G3

-continued

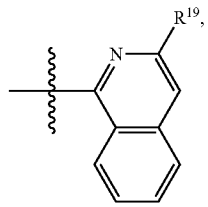

G4

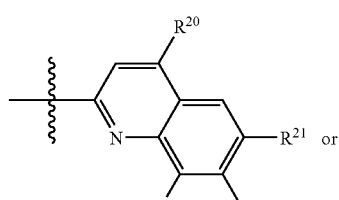

G5

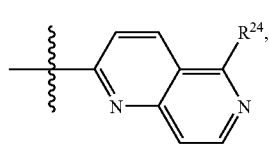

G6 wherein $R^7$ and $R^{11}$ are hydrogen;

$R^8$ and $R^{10}$ independently from each other are hydrogen or —NH—C(O)—$R^{25}$, wherein $R^{25}$ is $C_{1-7}$-alkyl;

$R^9$ is selected from the group consisting of hydrogen, $C_{1-7}$-alkyl, halogen, halogen-$C_{1-7}$-alkyl, cyano, —C(O)OR$^{26}$, wherein $R^{26}$ is hydrogen or $C_{1-7}$-alkyl, —(CH$_2$)$_m$—S(O)$_2$—NH—$R^{27}$, wherein m is 0 or 1 and $R^{27}$ is selected from $C_{1-7}$-alkyl, unsubstituted heteroaryl and heteroaryl substituted by $C_{1-7}$-alkyl; and —NH—S(O)$_2$—$R^{28}$, wherein $R^{28}$ is $C_{1-7}$-alkyl; or or $R^8$ and $R^9$ are bonded to each other to form a ring together with the carbon atoms they are attached to and $R^8$ and $R^9$ together are —CH$_2$—S(O)$_2$—CH$_2$—;

$R^{12}$ is selected from the group consisting of hydrogen, $C_{1-7}$-alkyl, halogen and amino;

$R^{13}$ is selected from the group consisting of hydrogen, $C_{1-7}$-alkyl, halogen, halogen-$C_{1-7}$-alkyl, cyano, nitro, phenyl, tetrazolyl, benzoimidazolyl, —COOR$^{29}$, wherein $R^{29}$ is hydrogen or $C_{1-7}$-alkyl, —CONHR$^{30}$, wherein $R^{30}$ is selected from the group consisting of hydrogen, $C_{1-7}$-alkyl, $C_{3-7}$-cycloalkyl, hydroxy-$C_{1-7}$-alkyl, $C_{1-7}$-alkoxy-$C_{1-7}$-alkyl, halogen-$C_{1-7}$-alkyl, carboxy-$C_{1-7}$-alkyl, —(CH$_2$)$_n$—NH—C(O)—$R^{31}$, wherein n is 1 or 2 and $R^{31}$ is $C_{1-7}$-alkyl, and —CO-heterocyclyl, wherein heterocyclyl is a ring selected from pyrrolidinyl, piperidinyl, piperazinyl and morpholinyl, said ring being unsubstituted or substituted by a group selected from hydroxy, carboxy, carbamoyl and $C_{1-7}$-alkanoyl;

$R^{14}$ is selected from the group consisting of hydrogen, $C_{1-7}$-alkyl, $C_{1-7}$-alkoxy, $C_{1-7}$-alkoxy-$C_{1-7}$-alkyl, cyano, carbamoyl, halogen and halogen-$C_{1-7}$-alkyl;

$R^{15}$ is selected from the group consisting of hydrogen, cyano, halogen and halogen-$C_{1-7}$-alkyl;

$R^{16}$ and $R^{18}$ are hydrogen;

$R^{17}$ is carbamoyl or —COOR$^{32}$, wherein $R^{32}$ is hydrogen or $C_{1-7}$-alkyl;

$R^{19}$ is hydrogen or halogen;

$R^{20}$ is selected from the group consisting of hydrogen, $C_{1-7}$-alkyl, $C_{1-7}$-alkoxy, $C_{1-7}$-alkoxy-$C_{1-7}$-alkyl and halogen;

R²¹, R²² and R²³ independently from each other are hydrogen or halogen;
R²⁴ is hydrogen or $C_{1-7}$-alkyl;
and pharmaceutically acceptable salts thereof.

19. The compound according to claim 1, selected from the group consisting of
4-[1-(3-ethoxy-4-methoxy-benzyl)-piperidin-4-ylamino]-benzonitrile,
4-[1-(4-chloro-3-ethoxy-benzyl)-piperidin-4-ylamino]-benzonitrile,
N-{3-[1-(4-chloro-3-ethoxy-benzyl)-piperidin-4-ylamino]-phenyl}-acetamide,
N-{3-[1-(3,5-diethoxy-4-fluoro-benzyl)-piperidin-4-ylamino]-phenyl}-acetamide,
[1-(3-ethoxy-4-methoxy-benzyl)-piperidin-4-yl]-(4-ethyl-phenyl)-amine,
C-{4-[1-(3-ethoxy-4-methoxy-benzyl)-piperidin-4-ylamino]-phenyl}-N-methyl-methanesulfonamide,
(2,2-dioxo-2,3-dihydro-1H-226-benzo[c]thiophen-5-yl)-[1-(3-ethoxy-4-methoxy-benzyl)-piperidin-4-yl]-amine,
4-[1-(3-ethoxy-4-methoxy-benzyl)-piperidin-4-ylamino]-benzoic acid,
4-[1-(3-ethoxy-4-methoxy-benzyl)-piperidin-4-ylamino]-N-(5-methyl-isoxazol-3-yl)-benzenesulfonamide,
N-{4-[1-(3-ethoxy-4-methoxy-benzyl)-piperidin-4-ylamino]-phenyl}-methanesulfonamide,
[5-(1H-benzoimidazol-2-yl)-pyridin-2-yl]-[1-(3-ethoxy-4-methoxy-benzyl)-piperidin-4-yl]-amine,
(7-chloro-4-methoxymethyl-quinolin-2-yl)-[1-(3-ethoxy-4-methoxy-benzyl)-piperidin-4-yl]-amine,
[1-(3-ethoxy-4-methoxy-benzyl)-piperidin-4-yl]-(6-fluoro-quinolin-2-yl)-amine,
6-[1-(3-ethoxy-4-methoxy-benzyl)-piperidin-4-ylamino]-nicotinonitrile,
[1-(3-ethoxy-4-methoxy-benzyl)-piperidin-4-yl]-(5-trifluoromethyl-pyridin-2-yl)-amine,
(6-chloro-pyridin-2-yl)-[1-(3-ethoxy-4-methoxy-benzyl)-piperidin-4-yl]-amine,
6-[1-(3-ethoxy-4-methoxy-benzyl)-piperidin-4-ylamino]-nicotinic acid ethyl ester,
6-[1-(3-ethoxy-4-methoxy-benzyl)-piperidin-4-ylamino]-nicotinic acid methyl ester,
[1-(3-ethoxy-4-methoxy-benzyl)-piperidin-4-yl]-(5-nitro-pyridin-2-yl)-amine,
(5-bromo-pyridin-2-yl)-[1-(3-ethoxy-4-methoxy-benzyl)-piperidin-4-yl]-amine,
[1-(3-ethoxy-4-methoxy-benzyl)-piperidin-4-yl]-(6-methyl-5-nitro-pyridin-2-yl)-amine,
N⁶-[1-(3-ethoxy-4-methoxy-benzyl)-piperidin-4-yl]-3-nitro-pyridine-2,6-diamine,
2-chloro-6-[1-(3-ethoxy-4-methoxy-benzyl)-piperidin-4-ylamino]-isonicotinic acid methyl ester,
2-[1-(3-ethoxy-4-methoxy-benzyl)-piperidin-4-ylamino]-6-methyl-5-phenyl-nicotinonitrile,
2-chloro-6-[1-(3-ethoxy-4-methoxy-benzyl)-piperidin-4-ylamino]-5-fluoro-nicotinonitrile,
[1-(3-ethoxy-4-methoxy-benzyl)-piperidin-4-yl]-quinolin-2-yl-amine,
[1-(3-ethoxy-4-methoxy-benzyl)-piperidin-4-yl]-(5-methyl-[1,6]naphthyridin-2-yl)-amine,
{2-chloro-6-[1-(4-chloro-3-ethoxy-benzyl)-piperidin-4-ylamino]-pyridin-4-yl}-methanol,
6-[1-(4-chloro-3-ethoxy-benzyl)-piperidin-4-ylamino]-nicotinic acid methyl ester,
[1-(4-chloro-3-ethoxy-benzyl)-piperidin-4-yl]-(5-trifluoromethyl-pyridin-2-yl)-amine,
[1-(4-chloro-3-ethoxy-benzyl)-piperidin-4-yl]-(3-trifluoromethyl-pyridin-2-yl)-amine,
[1-(4-chloro-3-ethoxy-benzyl)-piperidin-4-yl]-(6-methyl-5-nitro-pyridin-2-yl)-amine,
N⁶-[1-(4-chloro-3-ethoxy-benzyl)-piperidin-4-yl]-3-nitro-pyridine-2,6-diamine,
[1-(4-chloro-3-ethoxy-benzyl)-piperidin-4-yl]-(6-chloro-4-methoxymethyl-pyridin-2-yl)-amine,
2-[1-(4-chloro-3-ethoxy-benzyl)-piperidin-4-ylamino]-6-methyl-nicotinonitrile,
[1-(4-chloro-3-ethoxy-benzyl)-piperidin-4-yl]-(6-fluoro-quinolin-2-yl)-amine,
[1-(4-chloro-3-ethoxy-benzyl)-piperidin-4-yl]-(5-methyl-[1,6]naphthyridin-2-yl)-amine,
6-[1-(3-ethoxy-4-methyl-benzyl)-piperidin-4-ylamino]-nicotinonitrile,
6-[1-(3-ethoxy-4-fluoro-benzyl)-piperidin-4-ylamino]-nicotinonitrile,
6-[1-(4-chloro-3-ethoxy-benzyl)-piperidin-4-ylamino]-nicotinonitrile,
6-[1-(3-ethoxy-4-hydroxy-benzyl)-piperidin-4-ylamino]-nicotinonitrile,
6-[1-(3,5-diethoxy-benzyl)-piperidin-4-ylamino]-nicotinonitrile,
6-[1-(3,5-diisopropoxy-benzyl)-piperidin-4-ylamino]-nicotinonitrile,
6-[1-(3,5-diethoxy-4-fluoro-benzyl)-piperidin-4-ylamino]-nicotinonitrile,
6-[1-(4-chloro-3,5-diethoxy-benzyl)-piperidin-4-ylamino]-nicotinonitrile,
6-[1-(4-bromo-3,5-diethoxy-benzyl)-piperidin-4-ylamino]-nicotinonitrile,
6-[1-(4-amino-3,5-diethoxy-benzyl)-piperidin-4-ylamino]-nicotinonitrile,
6-[1-(3,5-diethoxy-4-pyrrol-1-yl-benzyl)-piperidin-4-ylamino]-nicotinonitrile,
6-[1-(3-ethoxy-4-methyl-benzyl)-piperidin-4-ylamino]-nicotinamide,
6-[1-(3-ethoxy-4-fluoro-benzyl)-piperidin-4-ylamino]-nicotinamide,
6-[1-(4-chloro-3-ethoxy-benzyl)-piperidin-4-ylamino]-nicotinamide,
6-[1-(3-ethoxy-4-hydroxy-benzyl)-piperidin-4-ylamino]-nicotinamide,
6-[1-(3-ethoxy-4-methoxy-benzyl)-piperidin-4-ylamino]-nicotinamide,
6-[1-(4-methoxy-3-propoxy-benzyl)-piperidin-4-ylamino]-nicotinamide,
6-[1-(3-isobutoxy-4-methoxy-benzyl)-piperidin-4-ylamino]-nicotinamide,
6-[1-(3,5-diethoxy-benzyl)-piperidin-4-ylamino]-nicotinamide,
6-[1-(3,5-diisopropoxy-benzyl)-piperidin-4-ylamino]-nicotinamide,
6-[1-(3,5-diethoxy-4-fluoro-benzyl)-piperidin-4-ylamino]-nicotinamide,
6-[1-(4-chloro-3,5-diethoxy-benzyl)-piperidin-4-ylamino]-nicotinamide,
6-[1-(4-amino-3,5-diethoxy-benzyl)-piperidin-4-ylamino]-nicotinamide,
6-[1-(3,5-diethoxy-4-pyrrol-1-yl-benzyl)-piperidin-4-ylamino]-nicotinamide,
6-[1-(3-ethoxy-4-methyl-benzyl)-piperidin-4-ylamino]-nicotinic acid,
6-[1-(3-ethoxy-4-fluoro-benzyl)-piperidin-4-ylamino]-nicotinic acid, 6-[1-(4-chloro-3-ethoxy-benzyl)-piperidin-4-ylamino]-nicotinic acid,
6-[1-(3-ethoxy-4-hydroxy-benzyl)-piperidin-4-ylamino]-nicotinic acid,
6-[1-(3-ethoxy-4-methoxy-benzyl)-piperidin-4-ylamino]-nicotinic acid,
6-[1-(3,5-diethoxy-benzyl)-piperidin-4-ylamino]-nicotinic acid,
6-[1-(3,5-diisopropoxy-benzyl)-piperidin-4-ylamino]-nicotinic acid,
6-[1-(3,5-diethoxy-4-fluoro-benzyl)-piperidin-4-ylamino]-nicotinic acid,
6-[1-(4-chloro-3,5-diethoxy-benzyl)-piperidin-4-ylamino]-nicotinic acid,
[1-(4-chloro-3-ethoxy-benzyl)-piperidin-4-yl]-[5-(1H-tetrazol-5-yl)-pyridin-2-yl]-amine,
[1-(3-ethoxy-4-methoxy-benzyl)-piperidin-4-yl]-[5-(1H-tetrazol-5-yl)-pyridin-2-yl]-amine,
[1-(3,5-diisopropoxy-benzyl)-piperidin-4-yl]-[5-(1H-tetrazol-5-yl)-pyridin-2-yl]-amine,
[1-(3,5-diethoxy-4-fluoro-benzyl)-piperidin-4-yl]-[5-(1H-tetrazol-5-yl)-pyridin-2-yl]-amine,
[1-(4-bromo-3,5-diethoxy-benzyl)-piperidin-4-yl]-[5-(1H-tetrazol-5-yl)-pyridin-2-yl]-amine,
[1-(3-ethoxy-4-methyl-benzyl)-piperidin-4-yl]-(5-trifluoromethyl-pyridin-2-yl)-amine,
[1-(4-chloro-3-ethoxy-benzyl)-piperidin-4-yl]-(5-trifluoromethyl-pyridin-2-yl)-amine,
[1-(3-ethoxy-4-methoxy-benzyl)-piperidin-4-yl]-(5-trifluoromethyl-pyridin-2-yl)-amine,
[1-(4-methoxy-3-propoxy-benzyl)-piperidin-4-yl]-(5-trifluoromethyl-pyridin-2-yl)-amine,
[1-(3,5-diethoxy-benzyl)-piperidin-4-yl]-(5-trifluoromethyl-pyridin-2-yl)-amine,
[1-(3,5-diethoxy-4-fluoro-benzyl)-piperidin-4-yl]-(5-trifluoromethyl-pyridin-2-yl)-amine,
[1-(3,5-diethoxy-4-iodo-benzyl)-piperidin-4-yl]-(5-trifluoromethyl-pyridin-2-yl)-amine,
[1-(3-ethoxy-4-iodo-5-methoxymethoxy-benzyl)-piperidin-4-yl]-(5-trifluoromethyl-pyridin-2-yl)-amine,
[1-(3,5-diethoxy-4-pyrrol-1-yl-benzyl)-piperidin-4-yl]-(5-trifluoromethyl-pyridin-2-yl)-amine,
6-[1-(4-chloro-3-ethoxy-benzyl)-piperidin-4-ylamino]-4-trifluoromethyl-nicotinic acid methyl ester,
6-[1-(3-ethoxy-4-hydroxy-benzyl)-piperidin-4-ylamino]-4-trifluoromethyl-nicotinic acid methyl ester,
6-[1-(3-ethoxy-4-methoxy-benzyl)-piperidin-4-ylamino]-4-trifluoromethyl-nicotinic acid methyl ester,
6-[1-(4-methoxy-3-propoxy-benzyl)-piperidin-4-ylamino]-4-trifluoromethyl-nicotinic acid methyl ester,
6-[1-(3-isobutoxy-4-methoxy-benzyl)-piperidin-4-ylamino]-4-trifluoromethyl-nicotinic acid methyl ester,
[1-(3-ethoxy-4-methyl-benzyl)-piperidin-4-yl]-quinolin-2-yl-amine,
[1-(3-ethoxy-4-fluoro-benzyl)-piperidin-4-yl]-quinolin-2-yl-amine,
[1-(4-chloro-3-ethoxy-benzyl)-piperidin-4-yl]-quinolin-2-yl-amine,
[1-(3-ethoxy-4-methoxy-benzyl)-piperidin-4-yl]-quinolin-2-yl-amine,
{1-[3-ethoxy-4-(1-ethyl-propoxy)-benzyl]-piperidin-4-yl}-quinolin-2-yl-amine,
[1-(4-methoxy-3-propoxy-benzyl)-piperidin-4-yl]-quinolin-2-yl-amine,
[1-(3-allyloxy-4-methoxy-benzyl)-piperidin-4-yl]-quinolin-2-yl-amine,
[1-(3-butoxy-4-methoxy-benzyl)-piperidin-4-yl]-quinolin-2-yl-amine,
[1-(3-isobutoxy-4-methoxy-benzyl)-piperidin-4-yl]-quinolin-2-yl-amine,
[1-(8-ethoxy-2,2-dimethyl-2H-chromen-6-ylmethyl)-piperidin-4-yl]-quinolin-2-yl-amine,
[1-(3,5-diethoxy-benzyl)-piperidin-4-yl]-quinolin-2-yl-amine,
3-isopropoxy-5-[4-(quinolin-2-ylamino)-piperidin-1-ylmethyl]-phenol,
[1-(3,5-diisopropoxy-benzyl)-piperidin-4-yl]-quinolin-2-yl-amine,
[1-(3,5-diethoxy-4-fluoro-benzyl)-piperidin-4-yl]-quinolin-2-yl-amine,
[1-(4-chloro-3,5-diethoxy-benzyl)-piperidin-4-yl]-quinolin-2-yl-amine,
[1-(4-bromo-3,5-diethoxy-benzyl)-piperidin-4-yl]-quinolin-2-yl-amine,
[1-(4-amino-3,5-diethoxy-benzyl)-piperidin-4-yl]-quinolin-2-yl-amine,
[1-(3,5-diethoxy-4-pyrrol-1-yl-benzyl)-piperidin-4-yl]-quinolin-2-yl-amine,
[1-(3-ethoxy-4-methyl-benzyl)-piperidin-4-yl]-(4-methyl-quinolin-2-yl)-amine,
[1-(3-ethoxy-4-fluoro-benzyl)-piperidin-4-yl]-(4-methyl-quinolin-2-yl)-amine,
[1-(4-chloro-3-ethoxy-benzyl)-piperidin-4-yl]-(4-methyl-quinolin-2-yl)-amine,
[1-(3-ethoxy-4-methoxy-benzyl)-piperidin-4-yl]-(4-methyl-quinolin-2-yl)-amine,
3-isopropoxy-5-[4-(4-methyl-quinolin-2-ylamino)-piperidin-1-ylmethyl]-phenol,
[1-(3,5-diisopropoxy-benzyl)-piperidin-4-yl]-(4-methyl-quinolin-2-yl)-amine,
[1-(3,5-diethoxy-4-fluoro-benzyl)-piperidin-4-yl]-(4-methyl-quinolin-2-yl)-amine,
[1-(4-chloro-3,5-diethoxy-benzyl)-piperidin-4-yl]-(4-methyl-quinolin-2-yl)-amine,
[1-(4-bromo-3,5-diethoxy-benzyl)-piperidin-4-yl]-(4-methyl-quinolin-2-yl)-amine,
[1-(4-amino-3,5-diethoxy-benzyl)-piperidin-4-yl]-(4-methyl-quinolin-2-yl)-amine,
[1-(3,5-diethoxy-4-pyrrol-1-yl-benzyl)-piperidin-4-yl]-(4-methyl-quinolin-2-yl)-amine,
(4-chloro-quinolin-2-yl)-[1-(3-ethoxy-4-methyl-benzyl)-piperidin-4-yl]-amine,
[1-(4-chloro-3-ethoxy-benzyl)-piperidin-4-yl]-(4-chloro-quinolin-2-yl)-amine,
[1-(4-chloro-3,5-diethoxy-benzyl)-piperidin-4-yl]-(4-chloro-quinolin-2-yl)-amine,
[1-(4-amino-3,5-diethoxy-benzyl)-piperidin-4-yl]-(4-chloro-quinolin-2-yl)-amine,
(8-chloro-quinolin-2-yl)-[1-(3-ethoxy-4-methyl-benzyl)-piperidin-4-yl]-amine,
[1-(4-chloro-3-ethoxy-benzyl)-piperidin-4-yl]-(8-chloro-quinolin-2-yl)-amine,
4-[4-(8-chloro-quinolin-2-ylamino)-piperidin-1-ylmethyl]-2-ethoxy-phenol,
(8-chloro-quinolin-2-yl)-[1-(3-ethoxy-4-methoxy-benzyl)-piperidin-4-yl]-amine,
(8-chloro-quinolin-2-yl)-{1-[3-ethoxy-4-(1-ethyl-propoxy)-benzyl]-piperidin-4-yl}-amine,
(8-chloro-quinolin-2-yl)-[1-(4-methoxy-3-propoxy-benzyl)-piperidin-4-yl]-amine,
[1-(3-allyloxy-4-methoxy-benzyl)-piperidin-4-yl]-(8-chloro-quinolin-2-yl)-amine,

[1-(3-butoxy-4-methoxy-benzyl)-piperidin-4-yl]-(8-chloro-quinolin-2-yl)-amine,
(8-chloro-quinolin-2-yl)-[1-(3-isobutoxy-4-methoxy-benzyl)-piperidin-4-yl]-amine,
(8-chloro-quinolin-2-yl)-[1-(8-ethoxy-2,2-dimethyl-2H-chromen-6-ylmethyl)-piperidin-4-yl]-amine,
(8-chloro-quinolin-2-yl)-[1-(3,5-diethoxy-benzyl)-piperidin-4-yl]-amine,
4-[4-(8-chloro-quinolin-2-ylamino)-piperidin-1-ylmethyl]-2,6-diethoxy-benzoic acid ethyl ester,
(8-chloro-quinolin-2-yl)-[1-(3,5-diethoxy-4-fluoro-benzyl)-piperidin-4-yl]-amine,
[1-(4-bromo-3,5-diethoxy-benzyl)-piperidin-4-yl]-(8-chloro-quinolin-2-yl)-amine,
(8-chloro-quinolin-2-yl)-[1-(3,5-diethoxy-4-pyrrol-1-yl-benzyl)-piperidin-4-yl]-amine,
[1-(3-ethoxy-4-methyl-benzyl)-piperidin-4-yl]-isoquinolin-1-yl-amine,
[1-(3-ethoxy-4-fluoro-benzyl)-piperidin-4-yl]-isoquinolin-1-yl-amine,
[1-(4-chloro-3-ethoxy-benzyl)-piperidin-4-yl]-isoquinolin-1-yl-amine,
[1-(3-ethoxy-4-methoxy-benzyl)-piperidin-4-yl]-isoquinolin-1-yl-amine,
isoquinolin-1-yl-[1-(4-methoxy-3-propoxy-benzyl)-piperidin-4-yl]-amine,
[1-(3-allyloxy-4-methoxy-benzyl)-piperidin-4-yl]-isoquinolin-1-yl-amine,
[1-(3-butoxy-4-methoxy-benzyl)-piperidin-4-yl]-isoquinolin-1-yl-amine,
[1-(3-isobutoxy-4-methoxy-benzyl)-piperidin-4-yl]-isoquinolin-1-yl-amine,
[1-(8-ethoxy-2,2-dimethyl-2H-chromen-6-ylmethyl)-piperidin-4-yl]-isoquinolin-1-yl-amine,
[1-(3,5-diethoxy-benzyl)-piperidin-4-yl]-isoquinolin-1-yl-amine,
3-isopropoxy-5-[4-(isoquinolin-1-ylamino)-piperidin-1-ylmethyl]-phenol,
[1-(3,5-diisopropoxy-benzyl)-piperidin-4-yl]-isoquinolin-1-yl-amine,
[1-(3,5-diethoxy-4-fluoro-benzyl)-piperidin-4-yl]-isoquinolin-1-yl-amine,
[1-(4-chloro-3,5-diethoxy-benzyl)-piperidin-4-yl]-isoquinolin-1-yl-amine,
[1-(4-bromo-3,5-diethoxy-benzyl)-piperidin-4-yl]-isoquinolin-1-yl-amine,
[1-(3,5-diethoxy-4-pyrrol-1-yl-benzyl)-piperidin-4-yl]-isoquinolin-1-yl-amine,
(3-chloro-isoquinolin-1-yl)-[1-(3-ethoxy-4-methyl-benzyl)-piperidin-4-yl]-amine,
(3-chloro-isoquinolin-1-yl)-[1-(3-ethoxy-4-fluoro-benzyl)-piperidin-4-yl]-amine,
[1-(4-chloro-3-ethoxy-benzyl)-piperidin-4-yl]-(3-chloro-isoquinolin-1-yl)-amine,
4-[4-(3-chloro-isoquinolin-1-ylamino)-piperidin-1-ylmethyl]-2-ethoxy-phenol,
(3-chloro-isoquinolin-1-yl)-[1-(3-ethoxy-4-methoxy-benzyl)-piperidin-4-yl]-amine,
(3-chloro-isoquinolin-1-yl)-[1-(4-difluoromethoxy-3-ethoxy-benzyl)-piperidin-4-yl]-amine,
(3-chloro-isoquinolin-1-yl)-[1-(3-ethoxy-4-isopropoxy-benzyl)-piperidin-4-yl]-amine,
(3-chloro-isoquinolin-1-yl)-[1-(3-ethoxy-4-isobutoxy-benzyl)-piperidin-4-yl]-amine,
(3-chloro-isoquinolin-1-yl)-[1-(4-methoxy-3-propoxy-benzyl)-piperidin-4-yl]-amine,
[1-(3-allyloxy-4-methoxy-benzyl)-piperidin-4-yl]-(3-chloro-isoquinolin-1-yl)-amine,
[1-(3-butoxy-4-methoxy-benzyl)-piperidin-4-yl]-(3-chloro-isoquinolin-1-yl)-amine,
(3-chloro-isoquinolin-1-yl)-[1-(3-isobutoxy-4-methoxy-benzyl)-piperidin-4-yl]-amine,
(3-chloro-isoquinolin-1-yl)-[1-(8-ethoxy-2,2-dimethyl-2H-chromen-6-ylmethyl)-piperidin-4-yl]-amine,
(3-chloro-isoquinolin-1-yl)-[1-(3,5-diethoxy-benzyl)-piperidin-4-yl]-amine,
(3-chloro-isoquinolin-1-yl)-[1-(3,5-diethoxy-4-fluoro-benzyl)-piperidin-4-yl]-amine,
[1-(4-chloro-3,5-diethoxy-benzyl)-piperidin-4-yl]-(3-chloro-isoquinolin-1-yl)-amine,
[1-(4-bromo-3,5-diethoxy-benzyl)-piperidin-4-yl]-(3-chloro-isoquinolin-1-yl)-amine,
[1-(4-amino-3,5-diethoxy-benzyl)-piperidin-4-yl]-(3-chloro-isoquinolin-1-yl)-amine,
5-[1-(3-ethoxy-4-methyl-benzyl)-piperidin-4-ylamino]-pyrazine-2-carboxylic acid methyl ester,
5-[1-(3-ethoxy-4-fluoro-benzyl)-piperidin-4-ylamino]-pyrazine-2-carboxylic acid methyl ester,
5-[1-(4-chloro-3-ethoxy-benzyl)-piperidin-4-ylamino]-pyrazine-2-carboxylic acid methyl ester,
5-[1-(3-ethoxy-4-hydroxy-benzyl)-piperidin-4-ylamino]-pyrazine-2-carboxylic acid methyl ester,
5-[1-(3-ethoxy-4-methoxy-benzyl)-piperidin-4-ylamino]-pyrazine-2-carboxylic acid methyl ester,
5-[1-(3-ethoxy-4-isopropoxy-benzyl)-piperidin-4-ylamino]-pyrazine-2-carboxylic acid methyl ester,
5-[1-(4-methoxy-3-propoxy-benzyl)-piperidin-4-ylamino]-pyrazine-2-carboxylic acid methyl ester,
5-{1-[3-(2-fluoro-ethoxy)-4-methoxy-benzyl]-piperidin-4-ylamino}-pyrazine-2-carboxylic acid methyl ester,
5-[1-(3-isobutoxy-4-methoxy-benzyl)-piperidin-4-ylamino]-pyrazine-2-carboxylic acid methyl ester,
5-[1-(8-ethoxy-2,2-dimethyl-2H-chromen-6-ylmethyl)-piperidin-4-ylamino]-pyrazine-2-carboxylic acid methyl ester,
5-[1-(3,5-diethoxy-benzyl)-piperidin-4-ylamino]-pyrazine-2-carboxylic acid methyl ester,
5-[1-(3,5-diisopropoxy-benzyl)-piperidin-4-ylamino]-pyrazine-2-carboxylic acid methyl ester,
5-[1-(3,5-diethoxy-4-fluoro-benzyl)-piperidin-4-ylamino]-pyrazine-2-carboxylic acid methyl ester,
5-[1-(4-chloro-3,5-diethoxy-benzyl)-piperidin-4-ylamino]-pyrazine-2-carboxylic acid methyl ester,
5-[1-(4-bromo-3,5-diethoxy-benzyl)-piperidin-4-ylamino]-pyrazine-2-carboxylic acid methyl ester,
5-[1-(4-amino-3,5-diethoxy-benzyl)-piperidin-4-ylamino]-pyrazine-2-carboxylic acid methyl ester,
5-[1-(3,5-diethoxy-4-pyrrol-1-yl-benzyl)-piperidin-4-ylamino]-pyrazine-2-carboxylic acid methyl ester,
2-[1-(3-ethoxy-4-methyl-benzyl)-piperidin-4-ylamino]-isonicotinonitrile,
2-[1-(3-ethoxy-4-methyl-benzyl)-piperidin-4-ylamino]-isonicotinamide,
2-[1-(4-chloro-3-ethoxy-benzyl)-piperidin-4-ylamino]-isonicotinonitrile,
2-[1-(4-chloro-3-ethoxy-benzyl)-piperidin-4-ylamino]-isonicotinamide,
2-[1-(3,5-diisopropoxy-benzyl)-piperidin-4-ylamino]-isonicotinonitrile,
2-[1-(3,5-diisopropoxy-benzyl)-piperidin-4-ylamino]-isonicotinamide,
2-[1-(3,5-diethoxy-4-fluoro-benzyl)-piperidin-4-ylamino]-isonicotinonitrile, 2-[1-(3,5-diethoxy-4-fluoro-benzyl)-piperidin-4-ylamino]-isonicotinamide,
6-[1-(4-methoxy-3-propoxy-benzyl)-piperidin-4-ylamino]-4-trifluoromethyl-nicotinamide,
6-[1-(3-isobutoxy-4-methoxy-benzyl)-piperidin-4-ylamino]-4-trifluoromethyl-nicotinamide,
6-[1-(4-chloro-3-ethoxy-benzyl)-piperidin-4-ylamino]-4-trifluoromethyl-nicotinamide,
6-[1-(3,5-diethoxy-4-fluoro-benzyl)-piperidin-4-ylamino]-4-trifluoromethyl-nicotinamide,
6-[1-(3-ethoxy-4-hydroxy-benzyl)-piperidin-4-ylamino]-4-trifluoromethyl-nicotinic acid,
6-[1-(3-ethoxy-4-methoxy-benzyl)-piperidin-4-ylamino]-4-trifluoromethyl-nicotinic acid,
6-[1-(4-methoxy-3-propoxy-benzyl)-piperidin-4-ylamino]-4-trifluoromethyl-nicotinic acid,
6-[1-(3-isobutoxy-4-methoxy-benzyl)-piperidin-4-ylamino]-4-trifluoromethyl-nicotinic acid,
5-[1-(4-chloro-3-ethoxy-benzyl)-piperidin-4-ylamino]-pyrazine-2-carboxylic acid amide,
6-[1-(4-chloro-3,5-diethoxy-benzyl)-piperidin-4-ylamino]-N-(2-hydroxy-ethyl)-nicotinamide,
6-[1-(4-chloro-3,5-diethoxy-benzyl)-piperidin-4-ylamino]-N-cyclobutyl-nicotinamide,
({6-[1-(4-chloro-3,5-diethoxy-benzyl)-piperidin-4-ylamino]-pyridine-3-carbonyl}-amino)-acetic acid,
6-[1-(4-chloro-3,5-diethoxy-benzyl)-piperidin-4-ylamino]-N-(2-methoxy-ethyl)-nicotinamide,
{6-[1-(4-chloro-3,5-diethoxy-benzyl)-piperidin-4-ylamino]-pyridin-3-yl}-morpholin-4-yl-methanone,
{6-[1-(4-chloro-3,5-diethoxy-benzyl)-piperidin-4-ylamino]-pyridin-3-yl}-((R)-3-hydroxy-pyrrolidin-1-yl)-methanone,
6-[1-(4-chloro-3,5-diethoxy-benzyl)-piperidin-4-ylamino]-N-(2-hydroxy-1-hydroxymethyl-ethyl)-nicotinamide,
6-[1-(4-chloro-3,5-diethoxy-benzyl)-piperidin-4-ylamino]-N-(2,2,2-trifluoro-ethyl)-nicotinamide,
N-(2-acetylamino-ethyl)-6-[1-(4-chloro-3,5-diethoxy-benzyl)-piperidin-4-ylamino]-nicotinamide,
1-{6-[1-(4-chloro-3,5-diethoxy-benzyl)-piperidin-4-ylamino]-pyridine-3-carbonyl}-piperidine-4-carboxylic acid amide,
1-(4-{6-[1-(4-chloro-3,5-diethoxy-benzyl)-piperidin-4-ylamino]-pyridine-3-carbonyl}-piperazin-1-yl)-ethanone,
1-{6-[1-(4-chloro-3,5-diethoxy-benzyl)-piperidin-4-ylamino]-pyridine-3-carbonyl}-piperidine-4-carboxylic acid,
and pharmaceutically acceptable salts thereof.

20. The compound according to claim 1, selected from the group consisting of:
(3-chloro-isoquinolin-1-yl)-[1-(2,6-diethoxy-4'-fluoro-biphenyl-4-ylmethyl)-piperidin-4-yl]-amine,
5-[1-(2,6-diethoxy-4'-fluoro-biphenyl-4-ylmethyl)-piperidin-4-ylamino]-pyrazine-2-carboxylic acid methyl ester,
[1-(3,5-diethoxy-4-fluoro-benzyl)-piperidin-4-yl]-(5-methanesulfonyl-pyridin-2-yl)-amine,
[1-(4-chloro-3,5-diethoxy-benzyl)-piperidin-4-yl]-(5-methanesulfonyl-pyridin-2-yl)-amine,
[1-(2,6-diethoxy-4'-fluoro-biphenyl-4-ylmethyl)-piperidin-4-yl]-(5-methanesulfonyl-pyridin-2-yl)-amine,
2-chloro-6-[1-(3,5-diethoxy-4-fluoro-benzyl)-piperidin-4-ylamino]-isonicotinic acid methyl ester,
2-chloro-6-[1-(4-chloro-3,5-diethoxy-benzyl)-piperidin-4-ylamino]-isonicotinic acid methyl ester,
2-chloro-6-[1-(2,6-diethoxy-4'-fluoro-biphenyl-4-ylmethyl)-piperidin-4-ylamino]-isonicotinic acid methyl ester,
{6-[1-(2,6-diethoxy-4'-fluoro-biphenyl-4-ylmethyl)-piperidin-4-ylamino]-pyridin-3-yloxy}-acetonitrile,
3-{6-[1-(4-chloro-3,5-diethoxy-benzyl)-piperidin-4-ylamino]-pyridin-3-yloxy}-propane-1,2-diol,
3-{6-[1-(2,6-diethoxy-4'-fluoro-biphenyl-4-ylmethyl)-piperidin-4-ylamino]-pyridin-3-yloxy}-propane-1,2-diol,
3-{6-[1-(2,6-diethoxy-4'-fluoro-biphenyl-4-ylmethyl)-piperidin-4-ylamino]-pyridin-3-yloxy}-propan-1-ol,
3-{6-[1-(4-chloro-3,5-diethoxy-benzyl)-piperidin-4-ylamino]-pyridin-3-yloxy}-propan-1-ol,
methanesulfonic acid 6-[1-(2,6-diethoxy-4'-fluoro-biphenyl-4-ylmethyl)-piperidin-4-ylamino]-pyridin-3-yl ester,
2-chloro-6-[1-(4-chloro-3,5-diethoxy-benzyl)-piperidin-4-ylamino]-isonicotinic acid,
2-chloro-6-[1-(2,6-diethoxy-4'-fluoro-biphenyl-4-ylmethyl)-piperidin-4-ylamino]-isonicotinic acid,
and pharmaceutically acceptable salts thereof.

21. The compound according to claim 1, selected from the group consisting of:
4-[1-(4-chloro-3-ethoxy-benzyl)-piperidin-4-ylamino]-benzonitrile,
6-[1-(4-chloro-3-ethoxy-benzyl)-piperidin-4-ylamino]-nicotinamide,
6-[1-(4-chloro-3,5-diethoxy-benzyl)-piperidin-4-ylamino]-nicotinamide,
6-[1-(4-chloro-3-ethoxy-benzyl)-piperidin-4-ylamino]-nicotinic acid,
6-[1-(4-chloro-3,5-diethoxy-benzyl)-piperidin-4-ylamino]-nicotinic acid,
[1-(3,5-diisopropoxy-benzyl)-piperidin-4-yl]-[5-(1H-tetrazol-5-yl)-pyridin-2-yl]-amine,
[1-(4-chloro-3-ethoxy-benzyl)-piperidin-4-yl]-quinolin-2-yl-amine,
[1-(4-chloro-3,5-diethoxy-benzyl)-piperidin-4-yl]-(4-methyl-quinolin-2-yl)-amine,
[1-(4-chloro-3,5-diethoxy-benzyl)-piperidin-4-yl]-isoquinolin-1-yl-amine,
({6-[1-(4-chloro-3,5-diethoxy-benzyl)-piperidin-4-ylamino]-pyridine-3-carbonyl}-amino)-acetic acid,
{6-[1-(4-chloro-3,5-diethoxy-benzyl)-piperidin-4-ylamino]-pyridin-3-yl}-morpholin-4-yl-methanone,
1-{6-[1-(4-chloro-3,5-diethoxy-benzyl)-piperidin-4-ylamino]-pyridine-3-carbonyl}-piperidine-4-carboxylic acid,
and pharmaceutically acceptable salts thereof.

22. A pharmaceutical composition, comprising a therapeutically effective amount of a compound according to claim 1 as well as a pharmaceutically acceptable carrier and/or adjuvant.

* * * * *

UNITED STATES PATENT AND TRADEMARK OFFICE
CERTIFICATE OF CORRECTION

PATENT NO. : 8,026,255 B2  
APPLICATION NO. : 12/776748  
DATED : September 27, 2011  
INVENTOR(S) : Alfred Binggeli et al.

Page 1 of 1

It is certified that error appears in the above-identified patent and that said Letters Patent is hereby corrected as shown below:

On the Title Page  
Item (73) Assignee: please delete "Hoffman-La Roche Inc.." and insert --Hoffmann-La Roche Inc.--

In Column 127, Claim 19, Line 19, please delete "(2,2-dioxo-2,3-dihydro-1H-226-benzo[c] thiophen-5-yl)-[1-(3-ethoxy-4-methoxy-benzyl)-"

and insert --(2,2-dioxo-2,3-dihydro-1H-2$\lambda$6-benzo[c] thiophen-5-yl)-[1-(3-ethoxy-4-methoxy-benzyl)- --

Signed and Sealed this  
Tenth Day of April, 2012

David J. Kappos  
*Director of the United States Patent and Trademark Office*